(12) United States Patent
Wang et al.

(10) Patent No.: US 11,286,531 B2
(45) Date of Patent: Mar. 29, 2022

(54) ASSAYING OVARIAN CYST FLUID

(71) Applicant: The Johns Hopkins University, Baltimore, MD (US)

(72) Inventors: Yuxuan Wang, Baltimore, MD (US); Bert Vogelstein, Baltimore, MD (US); Kenneth W. Kinzler, Baltimore, MD (US); Luis Diaz, Ellicot City, MD (US); Nickolas Papadopoulos, Towson, MD (US); Karin Sundfeldt, Gothenburg (SE); Bjorg Kristjansdottir, Gothenburg (SE)

(73) Assignee: The Johns Hopkins University, Baltimore, MD (US)

( * ) Notice: Subject to any disclaimer, the term of this patent is extended or adjusted under 35 U.S.C. 154(b) by 219 days.

(21) Appl. No.: 15/749,887

(22) PCT Filed: Aug. 11, 2016

(86) PCT No.: PCT/US2016/046453
§ 371 (c)(1),
(2) Date: Feb. 2, 2018

(87) PCT Pub. No.: WO2017/027653
PCT Pub. Date: Feb. 16, 2017

(65) Prior Publication Data
US 2018/0258490 A1 Sep. 13, 2018

Related U.S. Application Data

(60) Provisional application No. 62/203,573, filed on Aug. 11, 2015.

(51) Int. Cl.
*C12Q 1/6886* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

U.S. PATENT DOCUMENTS 5,750,341 A 5/1998 Macevicz
6,090,935 A 7/2000 Breivik et al.
(Continued)

FOREIGN PATENT DOCUMENTS

CN 1360059 7/2002
CN 102241772 11/2011
(Continued)

OTHER PUBLICATIONS

Khalid, A. et al. Gastrointestinal Endoscopy 69(6):1095. (Year: 2009).*

(Continued)

*Primary Examiner* — Diana B Johannsen
(74) *Attorney, Agent, or Firm* — Fish & Richardson P.C.

(57) ABSTRACT

A diagnostic test for ovarian cysts is based on the detection of mutations characteristic of the most common neoplasms giving rise to these lesions. With this test, tumor-specific mutations were detected in the cyst fluids of 19 of 24 (79%) borderline tumors and 28 of 31 (90%) malignant ovarian cancers. In contrast, we detected no mutations in the cyst fluids from 10 non-neoplastic cysts and 12 benign tumors. When categorized by the need for exploratory surgery (i.e., presence of a borderline tumor or malignant cancer), the sensitivity of this test was 85% and the specificity was 100%. These tests could inform the diagnosis of ovarian (Continued)

cysts and improve the clinical management of the large number of women with these lesions.

23 Claims, 27 Drawing Sheets

Specification includes a Sequence Listing.

(56) References Cited

U.S. PATENT DOCUMENTS

| | | |
|---|---|---|
| 6,156,504 A | 12/2000 | Gocke et al. |
| 6,248,521 B1 | 6/2001 | Van Ness et al. |
| 6,306,597 B1 | 10/2001 | Macevicz |
| 6,361,940 B1 | 3/2002 | Van Ness et al. |
| 6,514,736 B1 | 2/2003 | Erlich et al. |
| 6,576,420 B1 | 6/2003 | Carson et al. |
| 6,686,157 B2 | 2/2004 | Ward et al. |
| 6,746,845 B2 | 6/2004 | Kinzler et al. |
| 6,815,212 B2 | 11/2004 | Ness et al. |
| 6,890,764 B2 | 5/2005 | Chee et al. |
| 6,942,968 B1 | 9/2005 | Dickinson et al. |
| 6,977,153 B2 | 12/2005 | Kumar et al. |
| 7,056,660 B1 | 6/2006 | Diehl et al. |
| 7,060,431 B2 | 6/2006 | Chee et al. |
| 7,115,400 B1 | 10/2006 | Adessi et al. |
| 7,211,390 B2 | 5/2007 | Rothberg et al. |
| 7,232,656 B2 | 6/2007 | Balsubramanian et al. |
| 7,264,929 B2 | 9/2007 | Rothberg et al. |
| 7,323,305 B2 | 1/2008 | Leamon et al. |
| 7,323,310 B2 | 1/2008 | Peters et al. |
| 7,499,806 B2 | 3/2009 | Kermani et al. |
| 7,682,790 B2 | 3/2010 | Hollander et al. |
| 7,683,035 B1 | 3/2010 | Erbacher et al. |
| 7,700,286 B2 | 4/2010 | Stroun et al. |
| 7,702,468 B2 | 4/2010 | Chinitz et al. |
| 7,704,687 B2 | 4/2010 | Wang et al. |
| 7,745,125 B2 | 6/2010 | Gelfand et al. |
| 7,754,429 B2 | 7/2010 | Rigatti et al. |
| 7,776,531 B1 | 8/2010 | Black et al. |
| 7,811,759 B2 | 10/2010 | Han |
| 7,899,626 B2 | 3/2011 | Kruglyak et al. |
| 7,901,897 B2 | 3/2011 | Stuelpnagel et al. |
| 7,948,015 B2 | 5/2011 | Rothberg et al. |
| 7,957,913 B2 | 6/2011 | Chintz et al. |
| 7,977,108 B2 | 7/2011 | Newhouse et al. |
| 8,021,888 B2 | 9/2011 | Mohammed et al. |
| 8,026,053 B2 | 9/2011 | Samuels et al. |
| 8,043,834 B2 | 10/2011 | Abarzua et al. |
| 8,076,074 B2 | 12/2011 | Mohammed |
| 8,093,063 B2 | 1/2012 | Albitar |
| 8,150,626 B2 | 4/2012 | Fan et al. |
| 8,190,373 B2 | 5/2012 | Huang et al. |
| 8,288,103 B2 | 10/2012 | Oliphant et al. |
| 8,343,718 B2 | 1/2013 | Van Der Werf et al. |
| 8,372,637 B2 | 2/2013 | Hollander |
| 8,481,292 B2 | 7/2013 | Casbon et al. |
| 8,492,089 B2 | 7/2013 | Owen et al. |
| 8,658,572 B2 | 2/2014 | Albert et al. |
| 8,728,732 B2 | 5/2014 | Guerrero Preston et al. |
| 8,741,630 B2 | 6/2014 | Dickinson et al. |
| 8,765,419 B2 | 7/2014 | Hirschbein et al. |
| 8,822,158 B2 | 9/2014 | Froehlich et al. |
| 8,865,410 B2 | 10/2014 | Shendure et al. |
| 8,871,687 B2 | 10/2014 | Strom |
| 8,877,436 B2 | 11/2014 | Eder et al. |
| 8,911,942 B2 | 12/2014 | Mohammed et al. |
| 8,962,250 B2 | 2/2015 | Stanley |
| 9,012,149 B2 | 4/2015 | Kim et al. |
| 9,029,103 B2 | 5/2015 | Rigatti et al. |
| 9,045,796 B2 | 6/2015 | Gunderson et al. |
| 9,051,606 B2 | 6/2015 | Liu et al. |
| 9,074,206 B2 | 7/2015 | Wu et al. |
| 9,085,798 B2 | 7/2015 | Chee et al. |
| 9,115,410 B2 | 8/2015 | Nazarenko et al. |
| 9,163,283 B2 | 10/2015 | Chee et al. |
| 9,222,134 B2 | 12/2015 | Mann |
| 9,228,234 B2 | 1/2016 | Rabinowitz et al. |
| 9,233,125 B2 | 1/2016 | Davila et al. |
| 9,238,832 B2 | 1/2016 | Will et al. |
| 9,279,146 B2 | 3/2016 | Gupta et al. |
| 9,340,830 B2 | 5/2016 | Lipson et al. |
| 9,382,581 B2 | 7/2016 | Froehner et al. |
| 9,389,234 B2 | 7/2016 | Von Hoff et al. |
| 9,399,794 B2 | 7/2016 | Liu |
| 9,404,156 B2 | 8/2016 | Hicks et al. |
| 9,410,206 B2 | 8/2016 | Hoon et al. |
| 9,410,956 B1 | 8/2016 | Cheng |
| 9,422,593 B2 | 8/2016 | Rothmann et al. |
| 9,424,392 B2 | 8/2016 | Rabinowitz et al. |
| 9,441,267 B2 | 9/2016 | Gunderson et al. |
| 9,453,258 B2 | 9/2016 | Kain et al. |
| 9,476,095 B2 | 10/2016 | Vogelstein et al. |
| 9,487,823 B2 | 11/2016 | Lasken et al. |
| 9,546,399 B2 | 1/2017 | Amorese et al. |
| 9,546,404 B2 | 1/2017 | Sanders et al. |
| 9,556,491 B2 | 1/2017 | Hoon |
| 9,567,640 B2 | 2/2017 | Hoon |
| 9,574,234 B2 | 2/2017 | Straus et al. |
| 9,587,273 B2 | 3/2017 | Stuelpnagel et al. |
| 9,593,366 B2 | 3/2017 | Nazarenko et al. |
| 9,598,731 B2 | 3/2017 | Talasaz |
| 9,670,530 B2 | 6/2017 | Kostem et al. |
| 9,689,047 B2 | 6/2017 | O'Neil et al. |
| 9,702,004 B2 | 7/2017 | Van Eijk et al. |
| 9,708,655 B2 | 7/2017 | Mandell et al. |
| 9,745,632 B2 | 8/2017 | Parr et al. |
| 9,760,530 B2 | 9/2017 | Harsha et al. |
| 9,783,847 B2 | 10/2017 | Chee |
| 9,783,854 B2 | 10/2017 | Sanders et al. |
| 9,792,403 B2 | 10/2017 | Sun et al. |
| 9,797,000 B2 | 10/2017 | Lowe et al. |
| 9,816,139 B2 | 11/2017 | Breen |
| 9,828,672 B2 | 11/2017 | Varadarajan et al. |
| 9,834,822 B2 | 12/2017 | Talasaz et al. |
| 9,873,908 B2 | 1/2018 | Gupta et al. |
| 9,879,312 B2 | 1/2018 | Steemers et al. |
| 9,902,992 B2 | 2/2018 | Talasaz et al. |
| 9,914,973 B2 | 3/2018 | Cheng |
| 9,920,366 B2 | 3/2018 | Eltoukhy et al. |
| 9,944,924 B2 | 4/2018 | Rigatti et al. |
| 9,957,570 B2 | 5/2018 | Mori et al. |
| 9,965,585 B2 | 5/2018 | Lo et al. |
| 9,992,598 B2 | 6/2018 | Reiche |
| 10,011,826 B2 | 7/2018 | Hollander et al. |
| 10,011,870 B2 | 7/2018 | Zimmermann et al. |
| 10,017,759 B2 | 7/2018 | Kaper et al. |
| 10,023,904 B2 | 7/2018 | Villahermosa Jaen et al. |
| 10,023,917 B2 | 7/2018 | Buettner et al. |
| 10,041,127 B2 | 8/2018 | Talasaz |
| 10,102,337 B2 | 10/2018 | Scolnick et al. |
| 10,113,199 B2 | 10/2018 | Morin et al. |
| 10,227,652 B2 | 3/2019 | Rabinowitz et al. |
| 10,240,202 B2 | 3/2019 | Rabinowitz et al. |
| 10,266,893 B2 | 4/2019 | Rabinowitz et al. |
| 10,388,403 B2 | 8/2019 | Rava et al. |
| 10,422,006 B2 | 9/2019 | Samuels et al. |
| 10,457,995 B2 | 10/2019 | Talasaz |
| 10,494,678 B2 | 12/2019 | Talasaz |
| 10,501,793 B2 | 12/2019 | Chee et al. |
| 10,501,810 B2 | 12/2019 | Talasaz |
| 10,522,242 B2 | 12/2019 | Rabinowitz et al. |
| 10,526,658 B2 | 1/2020 | Babiraz et al. |
| 10,538,759 B2 | 1/2020 | Stuelpnagel et al. |
| 10,538,814 B2 | 1/2020 | Babiarz et al. |
| 10,557,172 B2 | 2/2020 | Babiarz et al. |
| 10,577,601 B2 | 3/2020 | Shendure et al. |
| 10,590,482 B2 | 3/2020 | Ryan et al. |
| 10,597,653 B2 | 3/2020 | Sabot et al. |
| 10,619,214 B2 | 4/2020 | Lo et al. |
| 10,704,085 B2 | 7/2020 | Talasaz et al. |
| 10,704,086 B2 | 7/2020 | Talasaz et al. |
| 10,704,105 B2 | 7/2020 | Samuels et al. |
| 10,704,108 B2 | 7/2020 | Vogelstein et al. |
| 10,731,220 B2 | 8/2020 | Babiraz et al. |

(56) References Cited

U.S. PATENT DOCUMENTS

| | | |
|---|---|---|
| 10,732,220 B2 | 8/2020 | Tamura et al. |
| 10,783,364 B2 | 9/2020 | Gao |
| 10,787,713 B2 | 9/2020 | Samuels et al. |
| 10,801,063 B2 | 10/2020 | Eltoukhy et al. |
| 10,822,663 B2 | 11/2020 | Talasaz |
| 10,894,987 B2 | 1/2021 | Vogelstein et al. |
| 2002/0160404 A1 | 10/2002 | Dietmaier et al. |
| 2005/0136405 A1 | 6/2005 | Linder et al. |
| 2005/0153313 A1 | 7/2005 | Endege et al. |
| 2005/0244847 A1 | 11/2005 | Domanico et al. |
| 2006/0127918 A1 | 6/2006 | Mohammed et al. |
| 2006/0263789 A1 | 11/2006 | Kincaid |
| 2006/0292576 A1 | 12/2006 | Albitar et al. |
| 2007/0020640 A1 | 1/2007 | McCloskey |
| 2007/0269805 A1 | 11/2007 | Hogers |
| 2008/0160580 A1 | 7/2008 | Adessi et al. |
| 2008/0286795 A1 | 11/2008 | Kawashima et al. |
| 2009/0088328 A1 | 4/2009 | Mohammed et al. |
| 2009/0105081 A1 | 4/2009 | Rodesch et al. |
| 2009/0215062 A1 | 8/2009 | Lee |
| 2009/0233802 A1 | 9/2009 | Bignell |
| 2009/0298187 A1 | 12/2009 | Nazarenko et al. |
| 2010/0041048 A1 | 2/2010 | Diehl et al. |
| 2010/0127186 A1 | 4/2010 | Bykanov et al. |
| 2010/0113758 A1 | 5/2010 | Wilmer et al. |
| 2010/0129874 A1 | 5/2010 | Mitra et al. |
| 2010/0248991 A1 | 9/2010 | Roesler et al. |
| 2010/0273219 A1 | 10/2010 | May et al. |
| 2011/0152111 A1 | 6/2011 | Fan et al. |
| 2011/0217309 A1 | 9/2011 | Buck et al. |
| 2011/0319415 A1 | 12/2011 | Thomas et al. |
| 2012/0010091 A1 | 1/2012 | Linnarson |
| 2012/0156753 A1 | 6/2012 | Jendrisak et al. |
| 2012/0225428 A1 | 9/2012 | Beck et al. |
| 2013/0059741 A1 | 3/2013 | Weiner |
| 2013/0266938 A1 | 10/2013 | Will |
| 2014/0011199 A1 | 1/2014 | Speiser et al. |
| 2014/0038837 A1 | 2/2014 | Fung et al. |
| 2014/0050788 A1 | 2/2014 | Daniel et al. |
| 2014/0066317 A1 | 3/2014 | Talasaz |
| 2014/0128270 A1 | 5/2014 | Nakao |
| 2014/0271635 A1 | 9/2014 | Brogdon et al. |
| 2014/0336996 A1 | 11/2014 | Sun et al. |
| 2014/0364323 A1 | 12/2014 | Fan et al. |
| 2015/0011416 A1 | 1/2015 | Lei et al. |
| 2015/0024948 A1 | 1/2015 | Dugas et al. |
| 2015/0051085 A1 | 2/2015 | Vogelstein et al. |
| 2015/0087535 A1 | 3/2015 | Patel |
| 2015/0093756 A1 | 4/2015 | Wolff et al. |
| 2015/0176071 A1 | 6/2015 | Fisher et al. |
| 2015/0197787 A1 | 7/2015 | Welder et al. |
| 2015/0225775 A1 | 8/2015 | Satya |
| 2015/0252415 A1 | 9/2015 | Vogelstein et al. |
| 2015/0275267 A1 | 10/2015 | O'Neil et al. |
| 2015/0307947 A1 | 10/2015 | Basu et al. |
| 2015/0324519 A1 | 11/2015 | Liu |
| 2015/0360193 A1 | 12/2015 | Fan et al. |
| 2016/0017320 A1 | 1/2016 | Wang et al. |
| 2016/0026758 A1 | 1/2016 | Jabara et al. |
| 2016/0048564 A1 | 2/2016 | Bassett, Jr. et al. |
| 2016/0092630 A1 | 3/2016 | Chen et al. |
| 2016/0194404 A1 | 7/2016 | June et al. |
| 2016/0251704 A1 | 9/2016 | Talasaz et al. |
| 2016/0273049 A1 | 9/2016 | Velculescu et al. |
| 2016/0281154 A1 | 9/2016 | So et al. |
| 2016/0319345 A1 | 11/2016 | Gnerre et al. |
| 2016/0374330 A1 | 12/2016 | Grolz |
| 2017/0009287 A1 | 1/2017 | Brastaad et al. |
| 2017/0039328 A1 | 2/2017 | Kathleen et al. |
| 2017/0058332 A1 | 3/2017 | Kermani et al. |
| 2017/0061072 A1 | 3/2017 | Kermani et al. |
| 2017/0101676 A1 | 4/2017 | Teng et al. |
| 2017/0137876 A1 | 5/2017 | Rigatti et al. |
| 2017/0141793 A1 | 5/2017 | Straus et al. |
| 2017/0165289 A1 | 6/2017 | Minomi et al. |
| 2017/0175197 A1 | 6/2017 | Gatalica et al. |
| 2017/0183742 A1 | 6/2017 | Thierry et al. |
| 2017/0240972 A1 | 8/2017 | Mokhtari et al. |
| 2017/0240973 A1 | 8/2017 | Eltoukhy et al. |
| 2017/0260590 A1 | 9/2017 | Eltoukhy et al. |
| 2017/0314081 A1 | 11/2017 | Gutinet et al. |
| 2017/0316149 A1 | 11/2017 | Maston |
| 2017/0356030 A1 | 12/2017 | Boyanov et al. |
| 2017/0356053 A1 | 12/2017 | Otto et al. |
| 2018/0002738 A1 | 1/2018 | Wang et al. |
| 2018/0002749 A1 | 1/2018 | Larson et al. |
| 2018/0016640 A1 | 1/2018 | Xu et al. |
| 2018/0023119 A1 | 1/2018 | Adey et al. |
| 2018/0037950 A1 | 2/2018 | Gunderson et al. |
| 2018/0051329 A1 | 2/2018 | Elzinga |
| 2018/0087105 A1 | 3/2018 | Larson et al. |
| 2018/0095969 A1 | 4/2018 | Jung et al. |
| 2018/0100859 A1 | 4/2018 | Cardone et al. |
| 2018/0119216 A1 | 5/2018 | Jamshidi et al. |
| 2018/0120291 A1 | 5/2018 | Eltoukhy et al. |
| 2018/0135044 A1 | 5/2018 | Sausen et al. |
| 2018/0135103 A1 | 5/2018 | Furlan et al. |
| 2018/0141020 A1 | 5/2018 | Gunderson et al. |
| 2018/0142304 A1 | 5/2018 | Sanders et al. |
| 2018/0148716 A1 | 5/2018 | Heitz et al. |
| 2018/0155705 A1 | 6/2018 | Wolf et al. |
| 2018/0155774 A1 | 6/2018 | Gunderson et al. |
| 2018/0163201 A1 | 6/2018 | Larson |
| 2018/0171337 A1 | 6/2018 | O'Neil et al. |
| 2018/0195131 A1 | 7/2018 | Mortimer |
| 2018/0201974 A1 | 7/2018 | Fraser |
| 2018/0201992 A1 | 7/2018 | Wu et al. |
| 2018/0203974 A1 | 7/2018 | Venn |
| 2018/0208999 A1 | 7/2018 | Lo et al. |
| 2019/0206510 A1 | 7/2019 | Jiang et al. |
| 2019/0256924 A1 | 8/2019 | Vogelstein et al. |
| 2019/0287654 A1 | 9/2019 | Curtis et al. |
| 2019/0376137 A1 | 12/2019 | Vogelstein et al. |
| 2020/0013482 A1 | 1/2020 | Sikora |
| 2020/0131568 A1 | 4/2020 | Talasz et al. |
| 2020/0157636 A1 | 5/2020 | Velculescu et al. |
| 2020/0377956 A1 | 12/2020 | Vogelstein et al. |

FOREIGN PATENT DOCUMENTS

| | | |
|---|---|---|
| EP | 1910560 | 12/2010 |
| EP | 3443119 | 2/2019 |
| EP | 3177740 | 1/2021 |
| WO | WO 2001/023618 | 4/2001 |
| WO | WO 2002/012897 | 2/2002 |
| WO | WO 2002/016649 | 2/2002 |
| WO | WO 2002/059355 | 8/2002 |
| WO | WO 2002/099982 | 12/2002 |
| WO | WO 2008030186 | 3/2008 |
| WO | 2008118877 | 10/2008 |
| WO | WO 2009/152928 | 12/2009 |
| WO | WO 2010/028098 | 3/2010 |
| WO | WO 2010/126614 | 11/2010 |
| WO | WO 2010/127186 | 11/2010 |
| WO | WO 2010/141955 | 12/2010 |
| WO | WO 2012/038839 | 3/2012 |
| WO | WO 2012/092336 | 7/2012 |
| WO | WO 2012/142213 | 10/2012 |
| WO | WO 2013/113816 | 8/2013 |
| WO | WO 2013/148496 | 10/2013 |
| WO | WO 2014183078 | 11/2014 |
| WO | WO 2015/198074 | 12/2015 |
| WO | WO 2016/130704 | 8/2016 |
| WO | WO 2016/135300 | 9/2016 |
| WO | WO 2016/140974 | 9/2016 |
| WO | WO 2016/141169 | 9/2016 |
| WO | WO 2016/170147 | 10/2016 |
| WO | WO 2016134136 | 11/2016 |
| WO | WO 2016/193490 | 12/2016 |
| WO | WO 2017/019456 | 2/2017 |
| WO | WO 2017/032808 | 3/2017 |
| WO | WO 2017/053915 | 3/2017 |
| WO | WO 2017/085321 | 5/2017 |
| WO | WO 2017/123316 | 7/2017 |

(56) References Cited

FOREIGN PATENT DOCUMENTS

| WO | WO 2017/127741 | 7/2017 |
|---|---|---|
| WO | WO 2017/132276 | 8/2017 |
| WO | WO 2017/132438 | 8/2017 |
| WO | WO 2017136603 | 8/2017 |
| WO | WO 2017/151524 | 9/2017 |
| WO | WO 2017/181134 | 10/2017 |
| WO | WO 2017/181146 | 10/2017 |
| WO | WO 2017/197027 | 11/2017 |
| WO | WO 2017/201315 | 11/2017 |
| WO | WO 2017/205686 | 11/2017 |
| WO | WO 2017/218512 | 12/2017 |
| WO | WO 2018/009723 | 1/2018 |
| WO | WO 2018/013598 | 1/2018 |
| WO | WO 2018/057770 | 3/2018 |
| WO | WO 2018/064629 | 4/2018 |
| WO | WO 2018/068014 | 4/2018 |
| WO | WO 2018064229 | 4/2018 |
| WO | WO 2018/077847 | 5/2018 |
| WO | WO 2018/081130 | 5/2018 |
| WO | WO 2018/085862 | 5/2018 |
| WO | WO 2018/093780 | 5/2018 |
| WO | WO 2018/111872 | 6/2018 |
| WO | WO 2018/119399 | 6/2018 |
| WO | WO 2018/119452 | 6/2018 |
| WO | WO 2018119438 | 6/2018 |
| WO | WO 2018/125892 | 7/2018 |
| WO | WO 2018/136416 | 7/2018 |
| WO | WO 2018/137826 | 8/2018 |
| WO | WO 2018093744 | 8/2018 |
| WO | WO 2018177847 | 10/2018 |
| WO | WO 2018/218113 | 11/2018 |
| WO | WO 2018204657 | 11/2018 |
| WO | WO 2020021119 | 1/2020 |

OTHER PUBLICATIONS

Troiano, R.N. et al. AJR 171:1601-1605. (Year: 1998).*
Urick, M.E. et al. Cancer Research 71 (12):4061. (Year: 2011).*
Gaspari, L. et al. Prenatal Diagnosis 32:859. (Year: 2012).*
Resaei-Matehkolaei, A. et al. Iranian J. Publ. Health 41(3):82-94. (Year: 2012).*
Dokianakis et al., "Ras gene activation in malignant cells of human ovarian carcinoma peritoneal fluids," Clin & Exp. Metastasis, 1999,17(4):293-297.
McConechy et al., "Use of mutation profiles to refine the classification of endometrial carcinomas," J. Path, 2012, 228:20-30 and supplementary table, pp. 1-11.
Sharma et al., "Screening for gynaecological cancers," EJSO, 2006, 32(8):818-824.
"Consensus sequence" (online) Oct. 4, 2011 <https://en.wikipedia.org/w/index.php?title=Consensus_sequence&oldid=423354064>.
"Polymerase chain reaction" (online) 2011, <https://web.archive.org/web/20110203140027/https:en.wikipedia.org/wiki/Polymerase>.
Abbosh et al., "Phylogenetic ctDNA analysis depicts early-stage lung cancer evolution", Nature 545: 446-451, 2017.
Abdel-Rahman, "Denosumab versus zoledronic acid to prevent aromatase inhibitors-associated fractures in postmenopausal early breast cancer; a mixed treatment meta-analysis.", Expert Rev Anticancer Ther 16(8): 885-91, 2016.
Agus et al., "Targeting ligand-activated ErbB2 signaling inhibits breast and prostate tumor growth", Cancer Cell 2: 127-137, 2002.
Albert et al., "Direct selection of human genomic loci by microarray hybridization", Nat. Methods 4: 903-905, 2007.
Albertini et al., "In vivo somatic mutations in humans: measurement and analysis.", Annu Rev Genet 24: 305-326, 1990.
AlHilli et al., "Incidence and factors associated with synchronous ovarian and endometrial cancer: a population-based case-control study.", Gynecologic oncology 125: 109-113, 2012.
Allegra et al., "American Society of Clinical Oncology provisional clinical opinion: testing for KRAS gene mutations in patients with metastatic colorectal carcinoma to predict response to anti-epidermal growth factor receptor monoclonal antibody therapy.", J. Clin. Oncol. 27: 2091-2096, 2009.
Allen et al., "Multi-institutional Validation Study of the American Joint Commission on Cancer (8th Edition) Changes for T and N Staging in Patients With Pancreatic Adenocarcinoma.", Ann Surg 265(1): 185-191, 2017.
Allory et al., "Telomerase Reverse Transcriptase Promoter Mutations in Bladder Cancer: High Frequency Across Stages, Detection in Urine, and Lack of Association with Outcome", Eur Urol 65: 360-366, 2014.
Alvarez et al., "Widespread Hypomethylation Occurs Early and Synergizes with Gene Amplification during Esophageal Carcinogenesis", PLOS Genetics, vol. 7, issue 3, e1001356, 1-14 pages, 2011.
Alvarez-Chaver et al., "Proteomics for discovery of candidate colorectal cancer biomarkers", World J. Gastroenterol. 20(14): 3804-3824, 2014.
Andre et al., "Improved overall survival with oxaliplatin, fluorouracil, and leucovorin as adjuvant treatment in stage II or III colon cancer in the MOSAIC trial.", J Clin Oncol 27(19): 3109-3116, 2009.
Anglesio et al., "Cancer-Associated Mutations in Endometriosis without Cancer", N Engl J Med 376: 1835-1848, 2017.
Ansari et al.,"Relationship between tumour size and outcome in pancreatic ductal adenocarcinoma", Br J Surg 104(5): 600-607, 2017.
Antoni et al., "Bladder Cancer Incidence and Mortality: A Global Overview and Recent Trends.", Eur Urol, 71(1), 96-108, 2017.
Araten et al., A quantitative measurement of the human somatic mutation rate., Cancer Res 65: 8111-8117, 2005.
Arnold et al., "Global burden of cancer attributable to high body-mass index in 2012: a population-based study.", The Lancet. Oncology 16, 36-46, 2015.
Audeh et al., "Oral poly(ADP-ribose) polymerase inhibitor olaparib in patients with BRCA1 or BRCA2 mutations and recurrent ovarian cancer: a proof-of-concept trial.", Lancet 376: 245-251, 2010.
Awada et al., "An open-label, dose-escalation study to evaluate the safety and pharmacokinetics of CEP-9722 (a PARP-1 and PARP-2 inhibitor) in combination with gemcitabine and cisplatin in patients with advanced solid tumors", Anticancer Drugs 27(4): 342-8, 2016.
Baard et al., Diagnostic dilemmas in patients with upper tract urothelial carcinoma., Nat Rev Urol, 14(3), 181-191, 2017.
Baehner, "The analytical validation of the Oncotype DX Recurrence Score assay", Ecancermedicalscience 10: 675, 2016.
Bahuva et al., "Morphologic abnormalities are poorly predictive of visceral pain in chronic pancreatitis.", Pancreas 42(1): 6-10, 2013.
Bainbridge et al., "Whole exome capture in solution with 3 Gbp of data" Genome Biology, 11(6): R62, 2010.
Bang et al., "Trastuzumab in combination with chemotherapy versus chemotherapy alone for treatment of HER2-positive advanced gastric or gastro-oesophageal junction cancer (ToGA): a phase 3, open-label, randomised controlled trial", Lancet 376: 687-697, 2010.
Bansal et al., "Low- and high-grade bladder cancer appraisal via serum-based proteomics approach,", Clin Chim Acta 436: 97-103, 2014.
Bardelli et al., "Liquid Biopsies, What We Do Not Know (Yet)", Cell Press, 31, 172-179, 2017.
Baretton et al., "Inerphase Cytogenetic Analysis of Prostatic Carcinomas by Use of Nonisotopic in Situ Hybridization", Cancer Research 54, 4472-4480, 1994.
Barkan et al., "The Paris System for Reporting Urinary Cytology: The Quest to Develop a Standardized Terminology,", Adv AnatPathol 23:193-201, 2016.
Barnes, "The fidelity of Taq polymerase catalyzing PCR is improved by an N-terminal deletion", Gene 112:29-35, 1992.
Barroso-Sousa et al., "Clinical Development of the CDK4/6 Inhibitors Ribociclib and Abemaciclib in Breast Cancer", Breast Care 11(3): 167-173, 2016.
Baselga et al., "Pertuzumab plus Trastuzumab plus Docetaxel for Metastatic Breast Cancer", N Engl J Med 366: 109-119, 2012.
Beddowes et al., "Predicting treatment resistance and relapse through circulating DNA.", Breast 34(Suppl 1): S31-S35, 2017.

(56) References Cited

OTHER PUBLICATIONS

Bell et al., "A simple way to treat PCR products prior to sequencing using ExoSAP-IT" BioTechniques, 2008.
Benson et al., "Colon Cancer, Version 1.2017", NCCN, vol. 15, No. 3, 370-398, 2017.
Beroukhim et al., "Assessing the significance of chromosomal aberrations in cancer: Methodology and application to glioma", Proceedings of the National Academy of Sciences, 104: 20007-20012, 2007.
Bertone et al., "Design optimization methods for genomic DNA tiling arrays", Genome Res 16(2): 271-281, 2006.
Bettegowda et al., "Detection of Circulating Tumor DNA in Early- and Late-Stage Human Malignancies", Science translational medicine 6(224): 224ra224, 2014.
Biankin et al., "Pancreatic cancer genomes reveal aberrations in axon guidance pathway genes.", Nature 491(7424): 399-405, 2012.
Bielas et al., "Quantification of random genomic mutations.", Nat. Methods, 2: 285-290, 2005.
Binladen et al., "The Use of Coded PCR Primers Enables High-Throughput Sequencing of Multiple Homolog Amplification Products by 454 Parallel Sequencing" PLoS One, 9 pages, Feb. 14, 2007.
Boyd et al., "Measurement and clinical monitoring of human lymphocyte clonality by massively parallel VDJ pyrosequencing.", Science Translat. Med., vol. 1, 12ra23, Supplementary material, pp. 1-30, 2009.
Bozic et al., "Evolutionary dynamics of cancer in response to targeted combination therapy", Elife 2: e00747, 2013.
Brahmer et al., "Safety and activity of anti-PD-L1 antibody in patients with advanced cancer.", N Engl J Med, 366(26): 2455-65, 2012.
Burris et al., "Phase I trial of novel kinesin spindle protein (KSP) inhibitor SB-715992 IV days 1, 8, 15 q 28 days", J. Clin. Oncol. 22: 128, 2004.
Calvez-Kelm et al., "KRAS mutations in blood circulating cell-free DNA: a pancreatic cancer casecontrol", Oncotarget, vol. 7, No. 48, 2016.
Camidge et al., "A phase I safety, tolerability, and pharmacokinetic study of enzastaurin combined with capecitabine in patients with advanced solid tumors", Anticancer Drugs 19: 77-84, 2008.
Campbell et al., "No difference in stem cell somatic mutation between the background mucosa of right- and left-sided sporadic colorectal carcinomas.", J Pathol 186: 31-35, 1998.
Cancer Genome Atlas Research Network, "Comprehensive molecular characterization of urothelial bladder carcinoma.", Nature 507: 315-322, 2014.
Cancer Genome Atlas Research, "Integrated genomic characterization of endometrial carcinoma.", Nature 497: 67-73, 2013.
Capello et al., "Sequential Validation of Blood-Based Protein Biomarker Candidates for Early-Stage Pancreatic Cancer.", J Natl Cancer Inst 109(4), 2017.
Casbon et al., "A method for counting PCR template molecules with application to next-generation sequencing," Nucleic Acids Research, 1-8, 2011.
Chai et al., Field effect in cancer—an update. Ann Clin Lab Sci 39: 331-337, 2009.
Chan et al., "Size Distributions of Maternal and Fetal DNA in Maternal Plasma", Clinical chemistry 50: 88-92, 2004.
Chan, "Consolidated guidelines on the use of antiretroviral drugs for treating and preventing HIV infection Recommendations for a public health approach", Second Edition, Book, 2016.
Chang et al., "CARs: Synthetic Immunoreceptors for Cancer Therapy and Beyond", Trends Mol Med 23(5): 430-450, 2017.
Chari et al., "Probability of pancreatic cancer following diabetes: a population based study". Gastroenterology 129(2): 504-511, 2005.
Chen et al., "Aristolochic acid-associated urothelial cancer in Taiwan", Proc Natl Acad Sci US A, 109(21): 8241-8246, 2012.
Chen et al., "CAR T-cell intrinsic PD-1 checkpoint blockade: A two-in-one approach for solid tumor immunotherapy", Oncoimmunology 6(2): e1273302, 2016.
Chen, "Immune checkpoint inhibitors for nonsmall cell lung cancer treatment", J. Chin Med Assoc 80(1): 7-14, 2017.
Cheng et al., "TERT Promoter Mutations Occur Frequently in Urothelial Papilloma and Papillary Urothelial Neoplasm of Low Malignant Potential.", Eur Urol 71 :497-498, 2017.
Chetverina et al., "Molecular colony diagnostics: detection and quantitation of viral nucleic acids by in-gel PCR.", Biotechniques 33: 150-152, 154, 156, 2002.
Cheung et al., "High frequency of PIK3R1 and PIK3R2 mutations in endometrial cancer elucidates a novel mechanism for regulation of PTEN protein stability.", Cancer Discov 1, 170-185, 2011.
Chiu et al., "Noninvasive prenatal diagnosis of fetal chromosomal aneuploidy by massively parallel genomic sequencing of DNA in maternal plasma", Proc Natl Acad Sci US A 105: 20458-20463, 2008.
Chu et al., J. Clin. Oncol. 22:14S, abstr 2078, 2004.
Chung et al., "A whole-genome mouse BAC microarray with 1-Mb resolution for analysis of DNA copy number changes by array comparative genomic hybridization.", Genome Res. 14(1): 188-196, 2004.
Clarke-Pearson, "Clinical Practice, Screening for ovarian cancer.", N Engl J Med., 361(2): 170-177, 2009.
Cohen et al., "Combined biomarker-based liquid biopsy for the earlier detection of pancreatic cancers". Proceedings of the National Academy of Sciences of the United States of America, vol. 114, No. 38, pp. 10202-102075, Sep. 2017.
Cohen et al., "Combined circulating tumor DNA and protein biomarker-based liquid biopsy for the earlier detection of pancreatic cancers", PNAS, vol. 114, No. 38, 10202-10207, 2017.
Cohen et al., "Detection and localization of surgically resectable cancers with a multi-analyte blood test", Science, 359(6378): 926-930, 2018.
Cohen et al., "Detection and localization of surgically resectable cancers with a multi-analyte liquid biopsy", Science, 82 pages, 2017.
Cole et al., "Working paper No. 3 Somatic mutant frequency, mutation rates and mutational spectra in the human population in vivo", MutatRes 304: 33-105, 1994.
Coombs et al., "Therapy-Related Clonal Hematopoiesis in Patients with Non-hematologic Cancers Is Common and Associated with Adverse Clinical Outcomes", Cell Stem Cell 21(3): 374-382, 2017.
Corona et al., "CDK4/6 inhibitors in HER2-positive breast cancer", Cri Rev Oncol Hematol 112: 208-214, 2017.
Cortes et al., "Support-Vector Networks", Machine learning 20: 273-297, 1995.
Costello et al., "Discovery and characterization of artifactual mutations in deep coverage targeted capture sequencing data due to oxidative DNA damage during sample preparation.", Nucleic acids research 41: e67, 2013.
Cowan et al., "Detection of TERT promoter mutations in primary adenocarcinoma of the urinary bladder.", Hum Pathol., 53: 8-13, 2016.
Craig et al., "Identification of genetic variants using bar-coded multiplexed sequencing.", Nat Methods 5: 887-893, 2008.
Cree et al., "The evidence base for circulating tumour DNA blood-based biomarkers for the early detection of cancer: a systematic mapping review", BMC Cancer, 17: 697, 1-17, 2017.
D'Souza et al., "Tumor characterization by ultrasound-release of multiple protein and microRNA biomarkers, preclinical and clinical evidence", PLOS ONE, 1-17 pages, 2018.
Dalma-Weiszhausz et al., "The affymetrix GeneChip platform: an overview.", Methods Enzymol. 410: 3-28, 2006.
Darragh et al., "Tumor Detection by Imaging Proteolytic Activity", Cancer Res 70: 1505-12, 2010.
Davis et al., "Diagnosis, evaluation and follow-up of asymptomatic microhematuria (AMH) in adults: AUA guideline.", J Urol 188: 2473-2481, 2012.
Dawson et al., "Analysis of Circulating Tumor DNA to Monitor Metastatic Breast Cancer", N Engl J Med 368(13): 1199-1209, 2013.
De Boer et al., "An in vitro assay for frameshift mutations: hotspots for deletions of 1 bp by Klenow-fragment polymerase share a consensus DNA sequence.", Genetics 118: 181-191, 1988.

(56) References Cited

OTHER PUBLICATIONS

De Vos et al., "Novel PMS2 Pseudogenes Can Conceal Recessive Mutations Causing a Distinctive Childhood Cancer Syndrome", American journal of human genetic, 74: 954-964, 2004.
Demeur et al., "Whole-genome Sequencing of an Aggressive BRAF Wild-type Papillary Thyroid Cancer Identified EML4-ALK Translocation as a Therapeutic Target", World J Surg., 38: 1296-305, 2014.
Derisi et al., "Use of a cDNA microarray to analyse gene expression patterns in human cancer.", Nat. Genet. 14: 457-460, 1996.
Di Renzo et al., "Expression of the MetfHepatocyte Growth Factor Receptor in Human Pancreatic Cancer", Cancer Res 55(5): 1129-1138, 1995.
Di Renzo et al., "Overexpression and amplification of the met/HGF receptor gene during the progression of colorectal cancer,", Clin Cancer Res 1(2): 147-154, 1995.
Diehl et al., "Analysis of mutations in DNA isolated from plasma and stool of colorectal cancer patients." Gastroenterology 135: 489-498, 2008.
Diehl et al., "Detection and quantification of mutations in the plasma of patients with colorectal tumors", Proceedings of the National Academy of Sciences of the United States of America, 102: 16368-16373, 2005.
Dimashkieh et al., "Evaluation of UroVysion and Cytology for Bladder Cancer Detection", Cancer Cytopathol 121: 591-597, 2013.
Dizon et al., "A Phase II Evaluation of Belinostat and Carboplatin in the Treatment of Recurrent or Persistent Platinum-Resistant Ovarian, Fallopian Tube, or Primary Peritoneal Carcinoma: A Gynecologic Oncology Group Study", Gynecol. Oncol. 125(2): 367-371, 2012.
Dizon et al., "Phase II Activity of Belinostat (PXD-101), Carboplatin, and Paclitaxel in Women With Previously Treated Ovarian Cancer", Int J. Gynecol. Cancer 23(3): 533-539, 2012.
Dohm et al., "Substantial biases in ultrashort read data sets from high-throughput DNA sequencing.", Nucleic Acids Res 36:e105, 2008.
Dong et al., "Combining markers with and without the limit of detection.", Stat Med 33(8): 1307-1320, 2014.
Douville et al., "Detection of aneuploidy in patients with cancer through amplification of long interspersed nucleotide elements (LINEs)", PNAS, vol. 115, No. 8, 1871-1876, 2018.
Dressman et al., Transforming single DNA molecules into fluorescent magnetic particles for detection and enumeration of genetic variations. Proc Natl Acad Sci US A 100(15): 8817-8822, 2003.
Drevis et al., "Phase I Clinical Study of AZD2171, an Oral Vascular Endothelial Growth Factor Signaling Inhibitor, in Patients With Advanced Solid Tumors", 25: 3045-2054, 2007.
Druley et al., "Quantification of rare allelic variants from pooled genomic DNA.", Nat Methods 6: 263-265, 2009.
D'Souza et al., "Tumor characterization by ultrasound-release of multiple protein and microRNA biomarkers, preclinical and clinical evidence", PLos One, 13: e0194268, 2018.
Durbin et al., "A map of human genome variation from population-scale sequencing.", Nature 467:1061-1073, 2010.
Dy et al., "Long-Term Survivors of Metastatic Colorectal Cancer Treated with Systemic Chemotherapy Alone: A North Central Cancer Treatment Group Review of 3811 Patients, N0144", Clin Colorectal Cancer 8(2): 88-93, 2009.
Eastman et al., "Maternal viral genotypic zidovudine resistance and infrequent failure of zidovudine therapy to prevent perinatal transmission of human immunodeficiency virus type 1 in pediatric AIDS Clinical Trials Group Protocol 076.", J Infect Dis 177:557-564, 1998.
Easton et al., "Breast and Ovarian Cancer Incidence in BRCA I-Mutation Carriers", Am. J. Hum. Genet. 56: 265-271, 1995.
Eckert et al., "High fidelity DNA synthesis by the Thermus aquaticus DNA polymerase.", Nucleic Acids Res 18: 3739-3744, 1990.
Egawa et al., "Clinicopathological aspects of small pancreatic cancer. Pancreas", 28(3): 235-240, 2004.

Ehab et al., "Profile of palbociclib in the treatment of metastatic breast cancer", Breast Cancer 8: 83-91, 2016.
Eid et al., "Real-time DNA sequencing from single polymerase molecules", Science 323: 133-138, 2009.
Eliassen et al., "Urinary Estrogens and Estrogen Metabolites and Subsequent Risk of Breast Cancer among Premenopausal Women", Cancer Research, vol. 72, issue 3, 696-706, 2012.
Ellinger et al., "Epigenetic biomarkers in the blood of patients with urological malignancies", Expert Rev Mal Diagn 15: 505-516, 2015.
Ellis et al., "Immune Checkpoint Inhibitors for Patients With Advanced None Small-Cell Lung Cancer: A Systematic Review", Clin Lung Cancer pii: S1525-7304(17)30043-8, 2017.
El-Tanani et al., "The regulation and role of osteopontin in malignant transformation and cancer.", Cytokine Growth Factor Rev 17(6): 463-474, 2006.
Elzek et al., "Proteomics of ovarian cancer: functional insights and clinical applications", Cancer Metastasis Rev., 34(1): 83-96, 2015.
Erickson et al., "Detection of somatic TP53 mutations in tampons of patients with highgrade serous ovarian cancer,", Obstetrics and gynecology 124, 881-885, 2014.
Erlich et al., "Alta-Cyclic: a self-optimizing base caller for next-generation sequencing.", Nat Methods 5: 679-682, 2008.
Ethier et al., "Bone Modifier Use as Adjuvant Therapy for Early Breast Cancer", Curr Oncol Rep 19(3): 15, 2017.
Extended European Search Report in Application No. 18193794.7, dated Dec. 19, 2018.
Extended European Search Report issued in related European Application No. 12772013.4, dated Sep. 17, 2014.
Extended European Search Report issued in related European Application No. 17154750.8, dated Aug. 17, 2017.
Faias et al., "Clinical Impact of KRAS and GNAS Analysis Added to CEA and Cytology in Pancreatic Cystic Fluid Obtained by EUS-FNA", Digestive Diseases and Sciences, vol. 63, No. 9, pp. 2351-2361, 2018.
Falchook et al., "Methylation and histone deacetylase inhibition in combination with platinum treatment in patients with advanced malignancies", Investig. New Drugs 31(5): 1192-1200, 2013.
Falzoi et al., "Multiplex genotyping of CYP3A4, CYP3A5, CYP2C9 and CYP2C19 SNPs using MALDI-TOF mass spectrometry", Pharmacogenomics 11: 559-571, 2010.
Fan et al., "Noninvasive diagnosis of fetal aneuploidy by shotgun sequencing DNA from maternal blood.", Proc Natl Acad Sci US A 105: 16266-16271, 2008.
Finn et al., "Palbociclib and Letrozole in Advanced Breast Cancer", N Eng J Med 375: 1925-1936, 2016.
Fishman et al., "The role of ultrasound evaluation in the detection of early-stage epithelial ovarian cancer.", Am J Obstet Gynecol 192, 1214-1221; discussion 1221-1212, 2005.
Fong et al., "Inhibition of poly(ADP-ribose) polymerase in tumors from BRCA mutation carriers", N Engl J Med 361: 123-134, 2009.
Forbes et al., "COSMIC: somatic cancer genetics at high-resolution", Nucleic Acids Res 45: D777-D783, 2017.
Forshew et al., "Noninvasive identification and monitoring of cancer mutations by targeted deep sequencing of plasma DNA", Sci Transl Med; 4: 136ra68, 2012.
Fradet et al., "Performance characteristics of a new monoclonal antibody test forbladder cancer: ImmunoCyt trade mark,", Can J Urol 4: 400-405, 1997 Abstract.
Friedman et al., "Regularization Paths for Generalized Linear Models via Coordinate Descent", Journal of Statistical Software 33 :74862, 22 pages, 2010.
Frokjaer et al., "Fibrosis, atrophy, and ductal pathology in chronic pancreatitis are associated with pancreatic function but independent of symptoms.", Pancreas 42(7): 1182-1187, 2013.
Fu et al., "Phase 1b-2a study to reverse platinum resistance through use of a hypomethylating agent, azacitidine, in patients with platinum-resistant or platinum-refractory epithelial ovarian cancer.", Cancer 117(8): 1661-1669, 2011.
Fujiwara et al., "Evaluation of Matrix Metalloproteinase-2 (MMP-2) Activity with Film in situ Zymography for Improved Cytological Diagnosis of Breast Tumors", Breast cancer 13: 272-8, 2006.

(56) References Cited

OTHER PUBLICATIONS

Fukagawa et al., "MicroRNA-135a-3p as a promising biomarker and nucleic acid therapeutic agent for ovarian cancer", Cancer Science, 108, 886-896, 2017.
Fullwood et al., "Next-generation DNA sequencing of paired-end tags (PET) for transcriptome and genome analyses" Genome Research, 19: 521-532, 2009.
Gam, "Breast cancer and protein biomarkers", World J. Exp. Med. 2(5): 86-91, 2012.
Gangi et al., "Metabolomic profile in pancreatic cancer patients: a consensusbased approach to identify highly discriminating metabolites", Oncotarget, vol. 7, No. 5, 2016.
Gasi et al., "Overexpression of Full-Length ETV1 Transcripts in Clinical Prostate Cancer Due to Gene Translocation", PLOS ONE, vol. 6, issue 1, e16332, 7 pages, 2011.
Geldenhuys et al., "Sensitivity and specificity of the Pap smear for glandular lesions of the cervix and endometrium,", Acta cytologica 51, 4 7-50, 2007.
Gelmon et al., "Olaparib in patients with recurrent high-grade serous or poorly differentiated ovarian carcinoma or triple-negative breast cancer: a phase 2, multicentre, open-label, non-randomised study", Lancet Oncol. 12: 852-61, 2011.
GenBank Accession No. NM000077, "*Homo sapiens* cyclin dependent kinase inhibitor 2A (CDKN2A), transcript variant 1, mRNA", dated Oct. 21, 2018, 7 pages.
GenBank Accession No. NM000142, "*Homo sapiens* fibroblast growth factor receptor 3 (FGFR3), transcript variant 1, mRNA", dated Dec. 23, 2018, 8 pages.
GenBank Accession No. NM000245, "*Homo sapiens* MET proto-oncogene, receptor tyrosine kinase (MET), transcript variant 2, mRNA", dated Jan. 13, 2019, 7 pages.
GenBank Accession No. NM000551, "*Homo sapiens* von Hippel-Lindau tumor suppressor (VHL), transcript variant 1, mRNA", dated Dec. 23, 2018, 7 pages.
GenBank Accession No. NMOO1005862, "*Homo sapiens* erb-b2 receptor tyrosine kinase 2 (ERBB2), transcript variant 2, mRNA", dated Jan. 13, 2019, 8 pages.
GenBank Accession No. NMOO 1127500, "*Homo sapiens* MET proto-oncogene, receptor tyrosine kinase (MET), transcript variant 1, mRNA",dated Jan. 13, 2019, 7 pages.
GenBank Accession No. NM001130442, "*Homo sapiens* HRas proto-oncogene, GTPase (HRAS), transcript variant 3, mRNA", dated Dec. 23, 2018, 5 pages.
GenBank Accession No. NM001163213, "*Homo sapiens* fibroblast growth factor receptor 3 (FGFR3), transcript variant 3, mRNA", dated Dec. 23, 2018, 7 pages.
GenBank Accession No. NM001195132, "*Homo sapiens* cyclin dependent kinase inhibitor 2A (CDKN2A), transcript variant 5, mRNA", dated Oct. 21, 2018, 7 pages.
GenBank Accession No. NMOO 1289936, "*Homo sapiens* erb-b2 receptor tyrosine kinase 2 (ERBB2), transcript variant 3, mRNA", dated Jan. 13, 2019, 8 pages.
GenBank Accession No. NMOO 1289937, "*Homo sapiens* erb-b2 receptor tyrosine kinase 2 (ERBB2), transcript variant 4, mRNA", dated Jan. 13, 2019, 8 pages.
GenBank Accession No. NM001289938, "*Homo sapiens* erb-b2 receptor tyrosine kinase 2 (ERBB2), transcript variant 5, mRNA", dated Jan. 13, 2019, 6 pages.
GenBank Accession No. NM001318054, "*Homo sapiens* HRas proto-oncogene, GTPase (HRAS), transcript variant 4, mRNA", dated Dec. 23, 2018, 5 pages.
GenBank Accession No. NM001324401, "*Homo sapiens* MET proto-oncogene, receptor tyrosine kinase (MET), transcript variant 3, mRNA", dated Jan. 13, 2019, 5 pages.
GenBank Accession No. NM001324402, "*Homo sapiens* MET proto-oncogene, receptor tyrosine kinase (MET), transcript variant 4, mRNA", dated Jan. 13, 2019, 6 pages.
GenBank Accession No. NM001354723, "*Homo sapiens* von Hippel-Lindau tumor suppressor (VHL), transcript variant 3, mRNA", dated Dec. 23, 2018, 4 pages.
GenBank Accession No. NM001354809, "*Homo sapiens* fibroblast growth factor receptor 3 (FGFR3), transcript variant 4, mRNA", dated Dec. 23, 2018, 6 pages.
GenBank Accession No. NM001354810, "*Homo sapiens* fibroblast growth factor receptor 3 (FGFR3), transcript variant 5, mRNA", dated Dec. 23, 2018, 6 pages.
GenBank Accession No. NM003482, "*Homo sapiens* lysine methyltransferase 2D (KMT2D), mRNA", dated Jan. 13, 2019, 21 pages.
GenBank Accession No. NM004448, "*Homo sapiens* erb-b2 receptor tyrosine kinase 2 (ERBB2), transcript variant 1, mRNA", dated Jan. 13, 2019, 10 pages.
GenBank Accession No. NM004985, "*Homo sapiens* KRAS proto-oncogene, GTPase (KRAS), transcript variant b, mRNA", dated Jan. 13, 2019, 7 pages.
GenBank Accession No. NM005343, "*Homo sapiens* HRas proto-oncogene, GTPase (HRAS), transcript variant 1, mRNA", dated Dec. 29, 2018, 5 pages.
GenBank Accession No. NM022965, "*Homo sapiens* fibroblast growth factor receptor 3 (FGFR3), transcript variant 2, mRNA", dated Dec. 23, 2018, 6 pages.
GenBank Accession No. NM033360, "*Homo sapiens* KRAS proto-oncogene, GTPase (KRAS), transcript variant a, mRNA", dated Jan. 13, 2019, 8 pages.
GenBank Accession No. NM058195, "*Homo sapiens* cyclin dependent kinase inhibitor 2A (CDKN2A), transcript variant 4, mRNA", dated Aug. 4, 2018, 6 pages.
GenBank Accession No. NM058196, "*Homo sapiens* cyclin-dependent kinase inhibitor 2A (melanoma, p16, inhibits CDK4) (CDKN2A), transcript variant 2, mRNA", dated Dec. 21, 2003, 19 pages.
GenBank Accession No. NM176795, "*Homo sapiens* HRas proto-oncogene, GTPase (HRAS), transcript variant 2, mRNA", dated Dec. 23, 2018, 5 pages.
GenBank Accession No. NM198156, "*Homo sapiens* von Hippel-Lindau tumor suppressor (VHL), transcript variant 2, mRNA", dated Dec. 23, 2018, 7 pages.
GenBank Release Note v. 220, p. 1 (Jun. 2017).
Geng et al., "Function and clinical significance of circRNAs in solid tumors", Journal of Hematology and Oncology, 11; 98, 20 pages, 2018.
Genovese et al., "Clonal hematopoiesis and blood-cancer risk inferred from blood DNA sequence.", N Engl J Med 371(26): 2477-2487, 2014.
Gerlinger et al., "Intratumor heterogeneity and branched evolution revealed by multiregion sequencing,", N Engl J Med 366, 883-892, 2012.
Ghosh et al., "Quantifying the sensitivities of EGF receptor (EGFR) tyrosine kinase inhibitors in drug resistant non-small cell lung cancer (NSCLC) cells using hydrogel-based peptide array.", Biosensors & Bioelectronics 26: 424-31, 2010.
Giacona et al.,"Cell-free DNA in human blood plasma: length measurements in patients with pancreatic cancer and healthy controls.", Pancreas 17: 89-97, 1998.
Gilbert et al., "Assessment of symptomatic women for early diagnosis of ovarian cancer: results from the prospective DOvE pilot project.", The Lancet. Oncology 13, 285-291, 2012.
Giligan et al., "American Society of Clinical Oncology Clinical Practice Guideline on uses of serum tumor markers in adult males with germ cell tumors.", J. Clin, Oncol. 28: 3388-3404, 2010.
Giraldez et al., "Droplet Digital PCR for Absolute Quantification of Extracellular MicroRNAs in Plasma and Serum: Quantification of the Cancer Biomarker hsa-miR-141.", Methods Mol. Biol., 1768: 459-74, 2018.
Gomez et al., "Efficacy and safety of lapatinib as first-line therapy for ErbB2-amplified locally advanced or metastatic breast cancer.", J Clin Oncol 26: 2999-30005, 2008.
Gong et al., "Efficacy and safety of everolimus in Chinese metastatic HR positive, HER2 negative breast cancer patients: a real-world retrospective study", Oncotarget, 8(35): 59810-59822, 2017.
Gonzalez-Pons "Colorectal Cancer Biomarkers: Where Are We Now?", Biomed. Res. Int. 2015: 149014, 2015.

(56) References Cited

OTHER PUBLICATIONS

Goodison et al., "A multi-analyte assay for the non-invasive detection of bladder cancer.", PLoS One, 7: e47469, 2012.
Gopalakrishna et al., "Anticipatory Positive Urine Tests for Bladder Cancer.", Ann Surg Oncol., 24: 1747-1753, 2017.
Gore et al., "Somatic coding mutations in human induced pluripotent stem cells.", Nature 471: 63-67, 2011.
Grist et al., "In vivo human somatic mutation: frequency and spectmm with age.", Mutat Res 266: 189-196, 1992.
Grollman et al., "Aristolochic acid nephropathy: Harbinger of a global iatrogenic disease.", Environ Mal Mutagen, 54(1): 1-7, 2013.
Gruenberger et al., "Bevacizumab, Capecitabine, and Oxaliplatin as Neoadjuvant Therapy for Patients With Potentially Curable Metastatic Colorectal Cancer", J. Clin Oncol. 26: 1830-1835, 2008.
Guetschow et al., "Detection of prolactin inducible protein mRNA, a biomarker for breast cancer metastasis, using a molecular beacon-based assay.", Anal. Bioanaly. Chem., 404: 399-406, 2012.
Hajdinjak, "UroVysion FISH test for detecting urothelial cancers: meta-analysis of diagnostic accuracy and comparison with urinary cytology testing,", Urol Oncol 26: 646-651, 2008.
Halama et al., "Nesting of colon and ovarian cancer cells in the endothelial niche is associated with alterations in glycan and lipid metabolism", Scientific Reports, 7:39999, 10 pages, 2017.
Hall et al., "Linkage of Early-Onset Familial Breast Cancer to Chromosome 17q21", Science 250: 1684-1689, 1990.
Hamanishi et al., "Safety and Antitumor Activity of Anti-PD-1 Antibody, Nivolumab, in Patients With Platinum-Resistant Ovarian Cancer.", J. Clin. Oncol. 33(34): 4015-4022, 2015.
Hamilton et al., "The Molecular Basis of Turcot's Syndrome", The New England Journal of Medicine 332: 839-847, 1995.
Hamilton et al., "Uterine papillary serous and clear cell carcinomas predict for poorer survival compared to grade 3 endometrioid corpus cancers", British journal of cancer 94: 642-646, 2006.
Hare et al., "mTOR function and therapeutic targeting in breast cancer", Am J Cancer Res 7(3): 383-404, 2017.
Harris et al., "American Society of Clinical Oncology 2007 Update of Recommendations for the Use of Tumor Markers in Breast Cancer", J. Clin. Oncol. 25: 5287-5312, 2007.
He et al., "Heteroplasmic mitochondrial DNA mutations in normal and tumour cells.", Nature 464: 610-614, 2010.
Hecht et al., "A randomized, double-blind, placebo-controlled, phase III study inpatients (Pts) with metastatic adenocarcinoma of the colon or rectum receiving fifirst-line chemotherapy with oxaliplatin/5-flfluorouracil/leucovorin and PTK787/ZK 222584 or placebo (CONFIRM-1)", ASCO Annual Meeting Proceedings J. Clin. Oncol. 23: 16S, abstr. LBA3, 2005.
Hellmann et al., "Nivolumab plus ipilimumab as first-line treatment for advanced non-small-cell lung cancer (CheckMate 012): results of an open-label, phase 1, multicohort study", Lancet Oncol. 18(1): 31-41, 2017.
Henrique et al., "DNA hypomethylation in plasma as a cancer biomarker: when less is more?", Expert Rev. Mol. Diagn., 14: 419-22, 2014.
Henry et al., "Cancer biomarkers", Mol. Oncol. 6: 140-146, 2012.
Herbst et al., "Lung cancer,", N Engl J Med, 359(13): 1367-1380, 2008.
Herman et al., "Filter-based hybridization capture of subgenomes enables resequencing and copy-number detection.", Nat Methods 6: 507-510, 2009.
Hiatt et al., "Parallel, tag-directed assembly of locallt dreived short sequence reads.", Nat Methods, (7) 119-122, 2010.
Hiatt et al., "Single molecule molecular inversion probes for targeted, high-accuracy detection of low-frequency variation.", Genome research 23, 843-854, 2013.
Hoang et al., "Mutational Signature of Aristolochic Acid Exposure as Revealed by Whole-Exome Sequencing", 2013 Science translational medicine 5: 197ral02, 2013.
Hodges et al., "High definition profiling of mammalian DNA methylation by array capture and single molecule bisulfite sequencing," Genome Research, 19: 1593-1605, 2009.

Hogenbirk et al., "Defining chromosomal translocation risks in cancer", PNAS, E3649-E3656, 2016.
Hoque et al., "High-throughput molecular analysis of urine sediment for the detection of bladder cancer by high-density single-nucleotide polymorphism array.", Cancer Res 63: 5723-5726, 2003.
Horn et al., "TERT promoter mutations in familial and sporadic melanoma." Science 339: 959-961, 2013.
Hosein et al., "Evaluating the repair of DNA derived from formalin-fixed paraffin-embedded tissues prior to genomic profiling by SNP-CGH analysis", Lab. Invest., 93, 701-710, 2013.
Hosgood et al., "Mitochondrial DNA copy number and lung cancer risk in a prospective cohort study", Carcinogen., 31: 847-9, 2010.
Hsieh et al., "Prescription profile of potentially aristolochic acid containing Chinese herbal products: an analysis of National Health Insurance data in Taiwan between 1997 and 2003", Chin Med, 3: 13, 6 pages, 2008.
Huang et al., "Comparison of Central HER2 Testing With Quantitative Total HER2 Expression and HER2 Homodimer Measurements Using a Novel Proximity-Based Assay", Am. J. Clin. Pathol. 134: 303-11, 2010.
Huang et al., "Highly recurrent TERT promoter mutations in human melanoma.", Science 339: 957-959, 2013.
Huang et al., "T-cell invigoration to tumour burden ratio associated with antiPD-1 response.", Nature 545(7652): 60-65, 2017.
Hughes et al., "Expression profiling using microarrays fabricated by an ink-jet oligonucleotide synthesizer.", Nat. Biotechnol, 19(4): 342-347, 2001.
Hui et al., "Pembrolizumab as first-line therapy for patients with PD-L1-positive advanced nonsmall cell lung cancer: a phase 1 trial", Ann Oncol 28(4): 874-881, 2017.
Hun et al., "Systems approach to characterize the metabolism of liver cancer stem cells expressing CD133", Sci. Rep. 7: 45557, 2017.
Hurst et al., "Comprehensive mutation analysis of the TERT promoter in bladder cancer and detection of mutations in voided urine.", Eur Urol 65: 367-369, 2014.
Hurwitz et al., "Bevacizumab plus Irinotecan, Fluorouracil, and Leucovorin for Metastatic Colorectal Cancer", N. Engl. J. Med. 350: 2335-2342, 2004.
Ikematsu et al., "Serum midkine levels are increased inpatients with various types of carcinomas", Br J Cancer 83(6): 701-706, 2000.
Ingvarsson et al., "Detection of pancreatic cancer using antibody microarray-based serum protein profiling,", Proteomics 8: 2211-9, 2008.
Innis et al., "Protocols for functional genomics" PCR application, (1999).
International Search Report and Written Opinion in International Application No. PCT/US2012/033207, dated Nov. 28, 2012.
International Search Report and Written Opinion in International Application No. PCT/US2018/045669, dated Nov. 28, 2018, 15 pages.
Irizarry et al., "Summaries of Affymetrix GeneChip probe level data", Nucleic Acids Res 31, 4 :e15, 2003.
Isakoff et al., "P3-16-05: A Phase II Trial Expansion Cohort of the PARP Inhibitor Veliparib (ABT888) and Temozolomide in BRCA1/2 Associated Metastatic Breast Cancer.", Cancer Res 71: P3-16-05, 2011.
Ishikawa et al., "Minute carcinoma of the pancreas measuring 1 cm or less in diameter—collective review of Japanese case reports.", Hepatogastroenterology 46(25): 8-15, 1999.
Jabara et al., "Accurate sampling and deep sequencing of the HIV-1 protease gene using a Primer ID.", Proceedings of the National Academy of Sciences of the United States of America 108, 20166-20171, 2011.
Jacobs et al., Sensitivity of transvaginal ultrasound screening for endometrial cancer in postmenopausal women: a case-control study within the UKCTOCS cohort. The Lancet. Oncology 12, 38-48, 2011.
Jahr et al., "DNA Fragments in the Blood Plasma of Cancer Patients: Quantitations and Evidence for Their Origin from Apoptotic andNecrotic Cells", Cancer Research 61: 1659-1665, 2001.
Jaiswal et al., "Age-related clonal hematopoiesis associated with adverse outcomes.", N Engl J Med 371(26): 2488-2498, 2014.

(56) References Cited

OTHER PUBLICATIONS

Jasmine et al., "A Genome-Wide Study of Cytogenetic Changes in Colorectal Cancer Using SNP Microarrays: Opportunities for Future Personalized Treatment", PLoS One 7(2): e31968, 18 pages, 2012.
Jelakovic et al., "Aristolactam-DNA adducts are a biomarker of environmental exposure to aristolochic acid", Kidney Int. 81(6): 559-67, 2012.
Jiao et al., "DAXX/ATRX, MEN1, and mTOR Pathway Genes Are Frequently Altered in Pancreatic Neuroendocrine Tumors", Science 331: 1199-1203, 2011.
Jones et al., "Core signaling pathways in human pancreatic cancers revealed by global genomic analyses.", Science 321(5897): 1801-1806, 2008.
Jones et al., "The epigenomics of cancer,", Cell 128: 683-692, 2007.
Ju et al., "Origins and functional consequences of somatic mitochondrial DNA mutations in human cancer", eLife 3, 28 pages, 2014.
Jung et al., "Intron retention is a widespread mechanism of tumor-suppressor inactivation.", Nat Genet 47, 1242-1248, 2015.
Kalinich et al., "An RNA-based signature enables high specificity detection of circulating tumor cells in hepatocellular carcinoma.", Proc Natl Acad Sci USA, 114(5): 1123-1128, 2017.
Kandoth et al., "Integrated genomic characterization of endometrial carcinoma.", Nature 497, 67-73, 2013.
Kandoth et al., "Mutational landscape and significance across 12 major cancer types", Nature 502: 333-339, 2013.
Karow, "Hopkins Team Develops method to Improve Rare Mutation Detection for Early Cancer Dx," Genomeweb, 3 pages, Jun. 1, 2011.
Karst et al., "Modeling high-grade serous ovarian carcinogenesis from the fallopian tube", Proc. Natl Acad Sci USA 108, 7547-7552, 2011.
Kaufamn et al., "Olaparib monotherapy in patients with advanced cancer and a germline BRCA1/2 mutation.", J Clin. Oncol. 33: 244-250, 2015.
Kawauchi et al., "9p21 index as estimated by dual-color fluorescence in situ hybridization is useful to predict urothelial carcinoma recurrence in bladder washing cytology.", Hum Pathol 40: 1783-1789, 2009.
Kennedy et al., "Detecting ultralow-frequency mutations by Duplex Sequencing.", Nature protocols 9, 2586-2606, 2014.
Kennedy et al., "Somatic mutations in aging, cancer and neurodegeneration", MechAgeing Dev 133: 118-126, 2012.
Keohavong et al., "Fidelity of DNA polymerases in DNA amplification.", Proc Natl Acad Sci US A 86: 9253-9257, 1989.
Kesmodel et al., "Gastrointestinal Cancers SymposiumSymposium: Multidisciplinary Approaches to the Prevention, Diagnosis, and Therapy of GI Cancers", abstr 234, 4 pages, 2007.
Keys et al., "Primer ID Informs Next-Generation Sequencing Platforms and Reveals Preexisting Drug Resistance Mutations in the HIV-1 Reverse Transcriptase Coding Domain.", AIDS Res Hum Retroviruses 31, 658-668, 2015.
Khadra et al., "A prospective analysis of 1,930 patients with hematuria to evaluate current diagnostic practice.", J Urol 163: 524-527, 2000.
Kidd et al., "Developing a SNP panel for forensic identification of individuals", Forensic science international 164: 20-32, 2006.
Killela et al., "TERT promoter mutations occur frequently in gliomas and a subset of tumors derived from cells with low rates of self-renewal.", Proc Natl Acad Sci USA 110:6021-6026, 2013.
Kim et al., "Clinical usefulness of carbohydrate antigen 19-9 as a screening test for pancreatic cancer in an asymptomatic population,", J Gastroenterol Hepatol 19(2): 182-186, 2004.
Kim et al., "Oligonucleotide microarray analysis of distinct gene expression patterns in colorectal cancer tissues harboring BRAF and K-ras mutations.", Carcinogenesis 27(3): 392-404, 2006.
Kinde et al., "Detection and quantification of rare mutations with massively parallel sequencing", Proceedings of the National Academy of Sciences of the United States of America 108, 9530-9535, 2011.
Kinde et al., "FAST-SeqS: a simple and efficient method for the detection of aneuploidy by massively parallel sequencing,", PloS ONE 7:e41162, 2012.
Kinde et al., "TERT promoter mutations occur early in urothelial neoplasia and are biomarkers of early disease and disease recurrence in urine.", Cancer Res 73 :7162-7167, 2013.
Kivioja et al., "Counting absolute Nos. of molecules using unique molecular identifiers," Nature Methods, vol. 9, No. 1, pp. 72-74, 2012.
Kobayashi et al., "A randomized study of screening for ovarian cancer: a multi center study in Japan,", Int J Gynecol Cancer 18, 414-420, 2008.
Konecny et al., "Activity of the Dual Kinase Inhibitor Lapatinib (GW572016) against HER-2-Overexpressing and Trastuzumab-Treated Breast Cancer Cells", Cancer Res 66: 1630-1639, 2006.
Koopmann et al., "Evaluation of Osteopontin as Biomarker for Pancreatic Adenocarcinoma", Cancer Epidemiol Biomarkers Prev 13(3): 487-491, 2004.
Korpanty et al., "Biomarkers that currently affect clinical practice in lung cancer: EGFR, ALK, MET, ROS-1, and KRAS", Front Oncol. 4: 204, 2014.
Kosuri et al., "Scalable gene synthesis by selective amplification of DNA pools from high-fidelity microchips.", Nat Biotechnol 28: 1295-1299, 2010.
Kou et al., "Benefits and Challenges with Applying Unique Molecular Identifiers in Next Generation Sequencing to Detect Low Frequency Mutations", PLOS ONE., vol. 11, No. 1, p. e0146638, 2016.
Kozarewa et al., "Amplification-free Illumina sequencing-library preparation facilitates improved mapping and assembly of (G+C)-biased genomes", Nature Methods, vol. 6, No. 4, pp. 291-295, 2009.
Kozarewa et al., "Amplification-free library preparation for paired-end illumina sequencing", chapter 18, pp. 257-266, 2011.
Kraystberg et al.,"Single-molecuke PCR: an artifact-free PCR approach for the analysis of somatic mutations" Expert Rev. Mol. Diagn. 5(5), 809-815, 2005.
Kraystberg et al.,"Single molecule PCR in mtDNA mutational analysis: genuine mutations vs. damage bypass-derived arttifacts" NIH Public Access Methods, 46(4): 269-273, 2008.
Krimmel et al., "Ultra-deep sequencing detects ovarian cancer cells in peritoneal fluid and reveals somatic TP53 mutations in noncancerous tissues.", Proc Natl Acad Sci USA 113, 6005-6010, 2016.
Kruger et al., "Numerical aberrations of chromosome 17 and the 9p2 1 locus are independent predictors of tumor recurrence in noninvasive transitional cell carcinoma of the urinary bladder.", Int J Oncol 23 :41-48, 2003.
Kumar et al., "Application of microarray in breast cancer: An overview ", J. Pharm. Bioallied Sci. 4(1): 21-26, 2012.
Kumar et al., "Association of mitochondrial copy number variation and T16189C polymorphism with colorectal cancer in North Indian population,", Tumour Biol, 39: 1010428317740296, 2017.
Kumar et al., "Cell-free mitochondrial DNA copy number variation in head and neck squamous cell carcinoma: A study of non-invasive biomarker from Northeast India.", Tumour Biol., 39: 1010428317736643, 2017.
Kumar et al., "Deep sequencing of multiple regions of glial tumors reveals spatial heterogeneity for mutations in clinically relevant genes.", Genome biology 15, 530, 2014.
Kumar et al., "Serum and Plasma Metabolomic Biomarkers for Lung Cancer", Bioinformation, 13(6); 202-208, 2017.
Kunkel, "The mutational specificity of DNA polymerase-beta during in vitro DNA synthesis.", J Biol Chem 260: 5787-5796, 1985.
Kuppusamy et al., "Proteins are potent biomarkers to detect colon cancer progression", Saudi Journal of Biological Sciences, 24, 1212-1221, 2017.
Kurman et al., "The Dualistic Model of Ovarian Carcinogenesis: Revisited, Revised, and Expanded.", Am J Pathol 186, 733-747, 2016.
Laddha et al., "Mutational Landscape of the Essential Autophagy Gene BECN1 in Human Cancers", Molecular cancer research 12: 485-490, 2014.
Laere et al., "cDNA Microarray Analysis of Inflammatory Breast Cancer Signatures", Methods Mol. Biol. 512: 71-98, 2009.

(56) References Cited

OTHER PUBLICATIONS

Lai et al., "Population-Based Case-Control Study of Chinese Herbal Products Containing Aristolochic Acid and Urinary Tract Cancer Risk", J Natl Cancer Inst, 102(3): 179-186, 2010.

Lalkhen et al., "Clinical tests: sensitivity and specificity", Continuing Education in Anaesthesia, Critical Care & Pain, vol. 8, No. 6, 221-223, 2008.

Langmead et al., "Fast gapped-read alignment with Bowtie 2", Nature Methods 9: 357-359, 2012.

Lee et al., "Quantification of kinase activity in cell lysates via photopatterned macroporous poly(ethylene glycol) hydrogel arrays in microfluidic channels", Biomed. Microdevices 14: 247-57, 2012.

Lennon et al., "Diagnostic and Therapeutic Response Markers.", Pancreatic Cancer, (Springer New York, New York, NY), pp. 675-701, 2010.

Lennon et al., "The Early Detection of Pancreatic Cancer: What Will It Take to Diagnose and Treat Curable Pancreatic Neoplasia?", Cancer Res 74(13): 3381-3389, 2014.

Levey et al., "Definition and classification of chronic kidney disease: a position statement from Kidney Disease: Improving Global Outcomes (KDIGO).", Kidney Int. 67(6): 2089-100, 2005.

Levey et al., "Using Standardized Serum Creatinine Values in the Modification of Diet in Renal Disease Study Equation for Estimating Glomerular Filtration Rate", Ann Intern Med. 145(4): 247-54, 2006.

Levina et al., "Biological significance of prolactin in gynecologic cancers.",Cancer Res 69(12): 5226-5233, 2009.

Li et al., "DNA Methylation in Peripheral Blood: A Potential Biomarker for Cancer Molecular Epidemiology", J. Epidemoil, 22(5): 384-394, 2012.

Li et al., "Replacing PCR with COLD-PCR enriches variant DNA sequences and redefines the sensitivity of genetic testing", Nat Med 14: 579-584, 2008.

Li et al., "Significant Predictive Factors for Prognosis of Primary Upper Urinary Tract Cancer after Radical Nephroureterectomy in Taiwanese Patients", Eur Ural. 54(5): 1127-1134, 2008.

Li et al., "Toward better understanding of artifacts in variant calling from high-coverage samples.", Bioinformatics 30: 2843-2851, 2014.

Liaw et al., "Classification and Regression by random Forest", R news 2: 18-22, 2001.

Lin et al., "A molecular inversion probe assay for detecting alternative splicing", BMC Genomics 11: 712, 2010.

Lin et al., "Benefits and harms of prostate-specific antigen screening for prostate cancer: an evidence update for the U.S. Preventive Services Task Force.", Ann. Intern. Med. 149: 192-199, 2008.

Lin et al., "Increase sensitivity in detecting superficial, low grade bladder cancer by combination analysis of hypermethylation of E-cadherin, p16, p14, RASSF1A genes in urine.", Ural Oncol 28: 597-602, 2010.

Linnarsson et al., "Recent advances in DNA sequencing methods—general principles of sample preparation", Experimental cell research., 316, 1339-1343, 2010.

Liotta et al., "The promise of proteomics.", Clin Adv Hematol Oncol 1(8): 460-462, 2003.

Lisca et al., "Prognostic significance of loss of heterozygosity at loci on chromosome 17p13.3-ter in sporadic breast cancer is evidence for a putative tumour suppressor gene", British Journal of Cancer, 80 (5/6) 821-826, 1999.

Liu et al., "Detection of extremely rare alleles by bidirectional pyrophosphorolysis-activated polymerization allele-specific amplification (Bi-PAP-A): measurement of mutation load in mammalian tissues.", Biotechniques 36: 156-166, 2004.

Liu et al., "Digital quantification of gene methylation in stool DNA by emulsion-PCR coupled with hydrogel immobilized bead-array.", Biosens Bioelectron 92: 596-601, 2017.

Livrahi et al., "PARP inhibitors in the management of breast cancer: current data and future prospects.", BMC Medicine 13: 188, 2015.

Locker et al., "ASCO 2006 Update of Recommendations for the Use of Tumor Markers in Gastrointestinal Cancer ", J. Clin. Oncol. 24: 5313-5327, 2006.

Lodato et al., "Somatic mutation in single human neurons tracks developmental and transcriptional history.", Science 350, 94-98, 2015.

Lodes et al., "Detection of Cancer with Serum miRNAs on an Oligonucleotide Microarray", PLoS One 4(7): e6229, 2009.

Lotan et al., "Sensitivity and Specificity of Commonly Available Bladder Tumor Markers Versus Cytology: Results of a Comprehensive Literature Review and Meta-Analyses", Urology 61: 109-18, 2003.

Lou et al., "Biomarkers for Hepatocellular Carcinoma", Biomark Cancer, 9: 1-9, 2017.

Louseberg et al., "Safety, Efficacy, and Patient Acceptability of Everolimus in the Treatment of Breast Cancer.", Breast Cancer 10: 239-252, 2017.

Lowe et al., "Multiplex Sensing of Protease and Kinase Enzyme Activity via Orthogonal Coupling of Quantum Dot-Peptide Conjugates", ACS nano, 6: 851-7, 2012.

Luria et al., "Mutations of Bacteria from Virus Sensitivity to Virus Resistance.", Genetics 28: 491-511, 1943.

Mackay et al., "cDNA microarray analysis of genes associated with ERBB2 (HER2/neu) overexpression in human mammary luminal epithelial cells", Oncogene 22: 2680-2688, 2003.

Mackay et al., "Phase II trial of the histone deacetylase inhibitor belinostat in women with platinum resistant epithelial ovarian cancer and micropapillary (LMP) ovarian tumours.", Eur. J. Cancer 46(9): 1573-1579, 2010.

Madabhushi et al., "DNA damage and its links to neurodegeneration.", Neuron 83, 266-282, 2014.

Makohon-Moore et al., "Limited heterogeneity of known driver gene mutations among the metastases of individual patients with pancreatic cancer", Nat Genet., 49(3): 358-366, 2017.

Mao et al., "The Application of Single Nucleotide Polymorphism Microarrays in Cancer Research", Curr. Genomics 8(4): 219-228, 2007.

Mao, "Recent advances in the molecular diagnosis of lung cancer.", Oncogene 21: 45, 6960-6969, 2002.

Maragh et al., "Evaluation of two mitochondrial DNA biomarkers for prostate cancer detection.", Cancer Biomark., 15: 763-73, 2015.

Matei et al., "Epigenetic Resensitization to Platinum in Ovarian Cancer", Cancer Res. 72(9): 2197-2205, 2012.

Matzas et al., "High-fidelity gene synthesis by retrieval of sequence-verified DNA identified using high-throughput pyrosequencing.", Nat Biotechnol 28: 1291-1294, 2010.

McCloskey et al., "Encoding PCR products with batch-stamps and barcodes", Biochem Genet 45: 761-767, 2007.

McMahon et al., "The HBV drug entecavir—effects on HIV-1 replication and resistance.", N Engl J Med 356: 2614-2621, 2007.

Meldrum et al., "Next-Generation Sequencing for Cancer Diagnostics: a Practical Perspective", Clin. Biochem. Rev. 32(4): 177-195, 2011.

Mendivil et al., "Increased incidence of severe gastrointestinal events with first-line paclitaxel, carboplatin, and vorinostat chemotherapy for advanced-stage epithelial ovarian, primary peritoneal, and fallopian tube cancer,", Int. J. Gynecol. Cancer 23(3): 533-539, 2013.

Menon et al., "Risk Algorithm Using Serial Biomarker Measurements Doubles the Number of Screen-Detected Cancers Compared With a Single-Threshold Rule in the United Kingdom Collaborative Trial of Ovarian Cancer Screening,", J Clin Oncol 33, 2062-2071, 2015.

Mermel et al., "GISTIC2.0 facilitates sensitive and confident localization of the targets of focal somatic copy-number alteration in human cancers", Genome biology 12: R41, 2011.

Metzker et al., "Sequencing technologies—the next generation" Nature reviews, 2010.

Michels et al., "Detection of DNA copy number alterations in cancer by array comparative genomic hybridization,", Genet. Med. 9: 574-584, 2007.

Miller et al., "Phase I trial of alvespimycin (KOS-1022; 17-DMAG) and trastuzumab (T)", J. Clin. Oncol. 25: sl 115, 2007.

Miner et al., "Molecular barcodes detect redundancy and contamination in hairpin-bisulfite PCR.", Nucleic Acids Res 32:e135, 2004.

(56) References Cited

OTHER PUBLICATIONS

Mirus et al., "Cross-Species Antibody Microarray Interrogation Identifies a 3-Protein Panel of Plasma Biomarkers for Early Diagnosis of Pancreas Cancer", Clin. Cancer Res. 21(7): 1764-1771, 2015.
Misek et al., "Protein Biomarkers for the Early Detection of Breast Cancer", International Journal of Proteomics, vol. 2011, article ID 343582, 9 pages, 2011.
Mishriki et al., "Diagnosis of urologic malignancies in patients with asymptomatic dipstick hematuria: prospective study with 13 years' follow-up.", Urology 71: 13-16, 2008.
Mitra et al., "Digital genotyping and haplotyping with polymerase colonies.", Proc Natl Acad Sci USA 100:5926-5931, 2008.
Mizutani et al., "A Novel FRET-Based Biosensor for the Measurement of BCR-ABL Activity and Its Response to Drugs in Living Cells", Clin. Cancer Res. 16: 3964-75, 2010.
Mo et al., "Hyperactivation of Haras oncogene, but not Ink4a/Arf deficiency, triggers bladder tumorigenesis.", J Clin Invest 117: 314-325, 2007.
Moch et al., "The 2016 WHO Classification of Tumours of the Urinary System and Male Genital Organs—Part A: Renal, Penile, and Testicular Tumours", EAU, 70, 93-105, 2016.
Mockler et al., "Applications of DNA tiling arrays for whole-genome analysis", Genomics, 85(1): 1-15, 2005.
Modesitt et al., "A phase II study of vorinostat in the treatment of persistent or recurrent epithelial ovarian or primary peritoneal carcinoma: a Gynecologic Oncology Group study.", 109(2): 182-186, 2008.
Modi et al., "Phase II trial of the Hsp90 inhibitor tanespimycin (Tan) + trastuzumab (T) in patients (pts) with HER2-positive metastatic breast cancer (MBC)", J. Clin Oncol. 26: sl027, 2008.
Moertel et al., "Fluorouracil plus levamisole as effective adjuvant therapy after resection of stage III colon carcinoma: a final report.", Ann Intern Med 122(5): 321-326, 1995.
Monnat et al., "Nucleotide sequence preservation of human mitochondrial DNA", Proc Natl Acad Sci USA 82: 2895-2899, 1985.
Moonen et al., "UroVysion compared with cytology and quantitative cytology in the surveillance of non-muscle-invasive bladder cancer.", Eur Urol 51: 1275-80, 2007.
Moore et al., "The use of multiple novel tumor biomarkers for the detection of ovarian carcinoma in patients with a pelvic mass.", Gynecologic oncology 108, 402-408, 2008.
Moore et al., "Uterine Papillary Serous Carcinoma", Clin Obstet Gynecol 54: 278-291, 2011.
Moyer et al., "Screening for ovarian cancer: U.S. Preventive Services Task Force reaffirmation recommendation statement", Annals of internal medicine 157: 900-904, 2012.
Nair et al., "Genomic Analysis of Uterine Lavage Fluid Detects Early Endometrial Cancers and Reveals a Prevalent Landscape of Driver Mutations in Women without Histopathologic Evidence of Cancer: A Prospective Cross-Sectional Study", PLoS Med 13: e1002206, 2016.
National Toxicology Program, Aristolochic acids. Rep Carcinog, 12, 45-49, 2011.
Nazarian et al., "Melanomas acquire resistance to B-RAF(V600E) inhibition by RTK or N-RAS upregulation.", Nature 468: 973-977, 2010.
Nazli et al., "The diagnostic importance of CEA and CA 19-9 for the early diagnosis of pancreatic carcinoma.", Hepatogastroenterology 47(36): 1750-1752, 2000.
Netto et al., "Emerging Bladder Cancer Biomarkers and Targets of Therapy.", Urol Clin North Am 43: 63-76, 2016.
Netto et al., "Theranostic and prognostic biomarkers: genomic applications in urological malignancies", Pathology 42: 384-394, 2010.
Netto, "Clinical applications ofrecent molecular advances in urologic malignancies: no longer chasing a "mirage"?.", Adv Anat Pathol 20: 175-203, 2013.
Netto, "Molecular biomarkers in urothelial carcinoma of the bladder: are we there yet?.", Nat Rev Urol 9: 41-51, 2011.
Ng et al., "Significance of endometrial cells in the detection of endometrial carcinoma and its precursors.", Acta cytologica 18, 356-361, 1974.
Ngan et al., "Abnormal expression and mutation of p53 in cervical cancer—a study at protein, RNA and DNA levels", Denitourin Med, 73: 54-58, 1997.
Nguyen et al., "High prevalence of TERT promoter mutations in micropapillaiy urothelial carcinoma.", Virchows Arch 469: 427-434, 2016.
Nolen et al., "Protein biomarkers of ovarian cancer: the forest and the trees", Future Oncol., 8(1): 55-71, 2012.
Non-Final Office Action issued in related U.S. Appl. No. 14/111,715, dated Oct. 15, 2015.
Non-Final Office Action issued in related U.S. Appl. No. 15/240,034, dated Dec. 23, 2016.
Non-Final Office Action issued in related U.S. Appl. No. 15/240,034, dated May 4, 2017.
Notice of Opposition in European Application No. 12772013.4, dated Jan. 11, 2018, 7 pages.
Notice of Opposition in European Application No. 12772013.4, dated Jan. 2, 2018, 22 pages.
Notice of Opposition in European Application No. 12772013.4, dated Jan. 9, 2018, 8 pages.
O'Brien et al., "Serum CA19-9 is significantly upregulated up to 2 years before diagnosis with pancreatic cancer: implications for early disease detection,", Clin Cancer Res 21(3): 622-631, 2015.
Odunsi et al., "Epigenetic potentiation of NY-ESO-1 vaccine therapy in human ovarian cancer", Cancer Immunol. Res. 2(1): 37-49, 2014.
Ogiwara et al., "Unbalanced translocation, a major chromosome alteration causing loss of heterozygosity in human lung cancer,", Oncogene, 27: 4788-97, 2008.
Ottesen et al., "Microfluidic digital PCR enables multigene analysis of individual environmental bacteria.", Science 314: 1464-1467, 2006.
Paik et al., "A Multigene Assay to Predict Recurrence of Tamoxifen-Treated, Node-Negative Breast Cancer", N. Engl. J. Med. 351: 2817-2826, 2004.
Parameswaran et al., "A pyrosequencing-tailored nucleotide barcode design unveils opportunities for large-scale sample multiplexing,", Nucleic Acids Res 35: e130, 2007.
Pardall, "The blockade of immune checkpoints in cancer immunotherapy", Nat. Rev Cancer 12: 252-264, 2012.
Park et al., "Large-scale clinical validation of biomarkers for pancreatic cancer using a mass spectrometry-based proteomics approach", Oncotarget, 8(26): 42761-42771, 2017.
Parsons et al., "Mismatch repair deficiency in phenotypically normal human cells", Science 268: 738-740, 1995.
Patel et al., "Endometrial carcinoma detected with SurePath liquid-based cervical cytology: comparison with conventional cytology", Cytopathology, vol. 20, No. 6, pp. 380-387, 2009.
Patz et al., "Panel of semm biomarkers for the diagnosis of lung cancer.", J Clin Oneal 25: 5578-5583, 2007.
Pengelly et al., "A SNP profiling panel for sample tracking in whole-exome sequencing studies", Genome medicine 5: 89, 2013.
Phallen et al., "Direct detection of early-stage cancers using circulating tumor DNA.", Science translational medicine 9, 2017.
Philips et al., "Targeting HER2-positive breast cancer with trastuzumab-DM1, an antibody-cytotoxic drug conjugate.", Cancer Res 68: 9280-9290, 2008.
Piccart-Gebhart et al., "Trastuzumab after adjuvant chemotherapy in HER2-positive breast cancer.", N. Engl. J. Med. 353: 1659-1672, 2005.
Pinkel et al., "Array comparative genomic hybridization and its applications in cancer", Nature Genetics, vol. 37, S11-S17, 2005.
Pinkel et al., "Summaries of Affymetrix GeneChip probe level data", Nat. Genetics 37:S11-S17, 2005.
Pinsky et al., "Prostate Cancer Screening—A Perspective on the Current State of the Evidence", The New England Journal of Medicine, 376; 13, 1285-1289, 2017.

(56) References Cited

OTHER PUBLICATIONS

Powers et al., "Protein analytical assays for diagnosing, monitoring, and choosing treatment for cancer patients.", J. Heathc Eng. 3(4): 503-534, 2015.
Proctor et al., "The promise of telomere length, telomerase activity and its regulation in the translocation-dependent cancer ESFT; clinical challenges and utility", Biochimica et Biophysica Acta, 260-274, 2009.
Quail et al., "A large genome center's improvements to the Illumina sequencing system,", Nat Methods 5:1005-1010, 2008.
Quail et al., "Improved Protocols for the Illumina Genome Analyzer Sequencing System," Current Protocols in Humar Genetics, Supplement 62, pp. 18.2.1-18.2.27, 2009.
Rahib et al., "Projecting Cancer Incidence and Deaths to 2030: The Unexpected Burden of Thyroid, Liver, and Pancreas Cancers in the United States", Cancer research 74, 2913-2921, 2014.
Ralla et al., "Nucleic acid-based biomarkers in body fluids of patients with urologic malignancies", Crit Rev Clin Lab Sci 51: 200-231, 2014.
Randerath et al., "Covalent DNA Damage in Tissues of Cigarette Smokers as Determined by 32P-Postlabeling Assay", Journal of the National Cancer Institute 81: 341-347, 1989.
Resta et al., "Phase I study of enzastaurin (ENZ) and bevacizumab (BV) in patients with advanced cancer", J. Clin. Oncol. 26 (May 20 suppl), abstr 3529, 2008.
Ricciuti et al., "Long-Lasting Response to Nivolumab and Immune-Related Adverse Events in a Nonsquamous Metastatic Non-Small Cell Lung Cancer Patient.", J. Thorne Oncol. 12(5): e51-e55, 2017.
Roach et al., "Analysis of Genetic Inheritance in a Family Quartet by Whole Genome Sequencing", Science 328: 636-639, 2010.
Rodriguez et al., Spectrum of genetic mutations in de novo PUNLMP of the urinary bladder. Virchows Arch, vol. 471, issue 6, pp. 761-767, 2017.
Romond et al., "Trastuzumab plus Adjuvant Chemotherapy for Operable HER2-Positive Breast Cancer", N. Engl. J. Med. 353: 1673-1684, 2005.
Rosen et al., "Safety, pharmacokinetics, and efficacy of AMG 706, an oral multikinase inhibitor, in patients with advanced solid tumors.", J. Clin. Oncol. 25: 2369-76, 2007.
Rosenberg et al., "Adoptive cell transfer as personalized immunotherapy for human cancer", Science 348(6230): 62-68, 2015.
Rougemont et al., "Probabilistic base calling of Solexa sequencing data.", BMC Bioinformatics 9:431, 2008.
Roupret et al., "European Association of Urology Guidelines on Upper Urinary Tract Urothelial Cell Carcinoma: 2015 Update", Eur Ural. 68(5): 868-79, 2015.
Ryan et al., "Pancreatic adenocarcinoma.", N Engl J Med 371(22): 2140-2141, 2014.
Saltz et al., "Phase II Trial of Sunitinib in Patients With Metastatic Colorectal Cancer After Failure of Standard Therapy", J. Clin. Oncol. 25: 4793-4799, 2007.
Sandhu et al., "The poly(ADP-ribose) polymerase inhibitor niraparib (MK4827) in BRCA mutation carriers and patients with sporadic cancer: a phase 1 dose-escalation trial.", Lancet Oncol 14: 882-92, 2013.
Saraswat et al., "Comparative proteomic profiling of the serum differentiates pancreatic cancer from chronic pancreatitis", Cancer Med., vol. 6, issue 7, 1738-1751, 2017.
Sarkis et al., "Association of P53 nuclear overexpression and tumor progression in carcinoma in situ of the bladder,", J Urol 152: 388-392, 1994.
Sarkis et al., "Nuclear overexpression ofp53 protein in transitional cell bladder carcinoma: a marker for disease progression,", J Natl Cancer Inst 85:53-59, 1993.
Sarkis et al., "Prognostic value of p53 nuclear overexpression in patients with invasive bladder cancer treated with neoadjuvant MVAC.", J Clin Oncol 13: 1384-1390, 1995.
Sarojini et al., "Early Detection Biomarkers for Ovarian Cancer", J. Oncol. 2012: 709049, 2012.
Sarosdy et al., "Use of a multitarget fluorescence in situ hybridization assay to diagnose bladder cancer in patients with hematuria.", J Urol 176: 44-47, 2006.
Schmidt et al., "Pre-diagnostic metabolite concentrations and prostate cancer risk in 1077 cases and 1077 matched controls in the European Prospective Investigation into Cancer and Nutrition", BMC Med, 15:122, 14 pages, 2012.
Schmitt et al., "Detection of ultra-rare mutations by next-generation sequencing", PNAS USA 109:14508-14513, 2012.
Schnatz et al., "Clinical significance of atypical glandular cells on cervical cytology.", Obstetrics and gynecology 107, 701-708, 2006.
Schroder et al., "Dual-color Proteomic Profiling of Complex Samples with a Microarray of 810 Cancer-related Antibodies",Mol. Cell. Proteomics 9: 1271-80, 2010.
Schulz et al., "Inhibiting the HSP90 chaperone destabilizes macrophage migration inhibitory factor and thereby inhibits breast tumor progression,", J Exp Med 209(2): 275-89, 2012.
Schwienbacher et al., "Abnormal RNA expression of 11p15 imprinted genes and kidney developmental genes in Wilms' tumor.", Cancer Res., 60: 1521-5, 2000.
Scott et al., "Mutations of the TERT promoter are common in basal cell carcinoma and squamous cell carcinoma.", Mod Pathol 27: 516-523, 2014.
Scott, "Niraparib: First Global Approval", Drugs, 77: 1029-1034, 2017.
Semrad et al., "Integrating Chemotherapy into the Management of Oligometastatic Colorectal Cancer: Evidence-Based Approach Using Clinical Trial Findings.", Ann Surg Oncol 22(Suppl 3): S855-862, 2015.
Serizawa et al., "Integrated genetic and epigenetic analysis of bladder cancer reveals an additive diagnostic value of FGFR3 mutations and hypermethylation events.", Int J Cancer 129(1):78-87, 2010.
Sethi et al., "Evolving Concept of Cancer Stem Cells: Role of Micro-RNAs and their Implications in Tumor Aggressiveness", J. Carcinog. Mutag. S 1-005, 2011.
Shariat et al., "Gender differences in radical nephroureterectomy for upper tract urothelial carcinoma", World J Ural. 29(4): 481-486, 2011.
Sharma et al., "Risk of epithelial ovarian cancer in asymptomatic women with ultrasound-detected ovarian masses: a prospective cohort study within the UK collaborative trial of ovarian cancer screening (UKCTOCS)", Ultrasound Obstet Gynecol 40: 338-344, 2012.
Shen et al., "BMN 673, a novel and highly potent PARP1/2 inhibitor for the treatment of human cancers with DNA repair deficiency.", Clin. Cancer Res. 19(18): 5003-5015, 2013.
Shen et al., "Mitochondrial copy number and risk of breast cancer: A pilot study", Mitochondrion, 10: 62-68, 2010.
Shi et al., "A Novel Proximity Assay for the Detection of Proteins and Protein Complexes: Quantitation of HER1 and HER2 Total Protein Expression and Homodimerization in Formalin-fixed, Paraffin-Embedded Cell Lines and Breast Cancer Tissue", Diagnostic molecular pathology: the American journal of surgical pathology, part B: 18: 11-21, 2009.
Shi et al., "LigAmp for sensitive detection of single-nucleotide differences.", Nat Methods 1: 141-147, 2007.
Shibata, "Mutation and epigenetic molecular clocks in cancer,", Carcinogenesis 32: 123-128, 2011.
Shlien et al., "Combined hereditary and somatic mutations of replication error repair genes result in rapid onset of ultra-hypermutated cancers.", Nature genetics 47: 257-262, 2015.
Sidranksy, "Nucleic acid-based methods for the detection of cancer.", Science 278(5340): 1054-9, 1997.
Sidransky et al., Identification of p53 gene mutations in bladder cancers and urine samples. Science 252: 706-709, 1991.
Siegel et al., "Cancer Statistics, 2017,", CA Cancer J Clin 67: 7-30, 2017.
Siravegna et al., "Integrating liquid biopsies into the management of cancer.", Nat Rev Clin Oncol 14, 531-548, 2017.

(56) References Cited

OTHER PUBLICATIONS

Skacel et al., "Multitarget Fluorescence In Situ Hybridization Assay Detects Transitional Cell Carcinoma in the Majority of Patients with Bladder Cancer and Atypical or Negative Urine Cytology", J Urol 169: 2101-2105, 2003.
Smith et al., "Epigenetic therapy for the treatment of epithelial ovarian cancer: A clinical review", Gynecol. Oncol. Rep. 20: 81-86, 2017.
Somlo et al., "Efficacy of the combination of ABT-888 (veliparib) and carboplatin in patients with BRCA-associated breast cancer.", J. Clin. Oncol. 31: 1024, 2013.
Song et al., "Prognostic factors in women with synchronous endometrial and ovarian cancers.", Int J Gynecol Cancer 24: 520-527, 2014.
Soria et al., "Epidemiology, diagnosis, preoperative evaluation and prognostic assessment of upper-tract urothelial carcinoma (UTUC)", World J Urol, 35(3), 379-387, 2017.
Sorscher, "Pembrolizumab in Non-Small-Cell Lung Cancer,", N Engl J Med 376, 10: 996-7, 2017.
Soung et al., "Exosomes in Cancer Diagnostics", Cancers 9(1):pii:E8, 2017.
Spalding et al., "Retrospective birth dating of cells in humans.", Cell 122, 133-143, 2005.
Springer et al., "A Combination of Molecular Markers and Clinical Features Improve the Classification of Pancreatic Cysts", Gastroenterology 149(6): 1501-1510, 2015.
Springer et al., "Non-invasive detection of urothelial cancer through the analysis of driver gene mutations and aneuploidy", eLIFE, 7: e32143, 27 pages, 2018.
Steensma et al., "Clonal hematopoiesis of indeterminate potential and its distinction from myelodysplastic syndromes.", Blood 126, 9-16, 2015.
Stem et al., "Mutation of the TERT promoter, switch to active chromatin, and monoallelic TERT expression in multiple cancers.", Genes Dev 29: 2219-2224, 2015.
Stratagene Catalog, p. 39, 1988.
Stratton et al., "The cancer genome.", Nature 458: 719-724, 2009.
Stromberg et al., "A high-throughput strategy for protein profiling in cell microarrays using automated image analysis.", Proteomics 7: 2142-50, 2007.
Sun et al., "Elevated expression of the centromere protein-A(CENP-A)-encoding gene as a prognostic and predictive biomarker in human cancers", Int. J. Cancer, 139, 899-907, 2016.
Sun et al., "Nivolumab effectively inhibit platinum-resistant ovarian cancer cells via induction of cell apoptosis and inhibition of ADAM17 expression", Eur Rev Med Pharmacol Sci 21(6): 1198-1205, 2017.
Tabernero et al., "Phase I study of AZD0530, an oral potent inhibitor of Src kinase: First demonstration of inhibition of Src activity in human cancers", J. Clin. Oncol. 25: 18S, abstr 3520, 2007.
Takahashi et al., "Clonal and chronological genetic analysis of multifocal cancers of the bladder and upper urinary tract.", Cancer Res 58: 5835-5841, 1998.
Tanase et al., "Prostate cancer proteomics: Current trends and future perspectives for biomarker discovery", Oncotarget., Mar. 14; 8(11): 18497-18512, 2017.
Tang et al., "A phase I study of vorinostat (VOR) in combination with capecitabine (CAP) in patients (pts) with advanced solid tumors", J. Clin. Oncol 26, May 20 suppl; abstr 4027, 2018.
Tao, "Direct intrauterine sampling: the IUMC Endometrial Sampler.", Diagnostic cytopathology 17, 153-159, 1997.
The 1000 Genomes Project Consortium, "An integrated map of genetic variation from 1,092 human genomes.", Nature 491: 56-65, 2012.
Thomas et al., "Construction of a 2-Mb resolution BAC microarray for CGH analysis of canine tumors", Genome Res. 15(12): 1831-1837, 2005.
Thomas et al., "Evaluation of semm CEA, CYFRA21-1 and CA125 for the early detection of colorectal cancer using longitudinal preclinical samples.", Br J Cancer 113(2): 268-274, 2015.
Thompson et al., "Winnowing DNA for Rare Sequences: Highly Specific Sequence and Methylation Based Enrichment", PLoS ONE, 7:e31597, 2012.
Thorpe et al., "Effects of blood collection conditions on ovarian cancer serum markers.", PLoS One 2(12): e1281, 2007.
Thunnissen, "Sputum examination for early detection of lung cancer.", J Clin Pathol 56: 805-810, 2003.
Thyagarajan et al., "Mitochondrial Copy Number is Associated With Colorectal Cancer Risk", Cancer Epidemiol Biomarkers Prev, 21(9): 1574-1581, 2012.
Tindall et al., "Fidelity of DNA synthesis by the Thermus aquaticus DNA polymerase.", Biochemistry 27: 6008-6013, 1988.
Tomasetti et al., "Cancer etiology. Variation in cancer risk among tissues can be explained by the number of stem cell divisions.", Science 347, 78-81, 2015.
Tomasetti et al., "Half or more of the somatic mutations in cancers of self-renewing tissues originate prior to tumor initiation.", Proceedings of the National Academy of Sciences of the United States of America 110, 1999-2004, 2013.
Tsuchiya et al., "Biomarkers for the early diagnosis of hepatocellular carcinoma", World J Gastroenterol., 21(37): 10573-10583, 2015.
Tsuchiya et al., "Collective review of small carcinomas of the pancreas.", Ann Surg 203(1): 77-81, 1986.
Turner et al., "Palbociclib in Hormone-Receptor-Positive Advanced Breast Cancer", N Engl J Med 373:209-219, 2015.
Tutt et al., "Oral poly(ADP-ribose) polymerase inhibitor olaparib in patients with BRCA1 or BRCA2 mutations and advanced breast cancer: a proof-of-concept trial", Lancet 376: 235-44, 2010.
Uhlen et al., "Tissue-based map of the human proteome.", Science 347(6220): 1260419, 2015.
Vallania et al., High-throughput discovery of rare insertions and deletions in large cohorts. Genome Res 20: 1711-1718, 2010.
Van Beers et al., "Array-CGH and breast cancer", Breast Cancer Res. 8(3): 210, 10 pages, 2006.
Van Dongen et al., "Analysis of immunoglobulin and T cell receptor genes. Part II: Possibilities and limitations in the diagnosis and management of lymphoproliferative diseases and related disorders.", Clin Chim Acta 198: 93-174, 1991.
Vansteenkiste et al., "Prospects and progress of atezolizumab in non-small cell lung cancer", Expert Opin Biol Ther 17(6): 781-789, 2017.
Vijg et al., "Somatic mutations, genome mosaicism, cancer and aging", Current opinion in genetics & development 26: 141-149, 2014.
Vogelstein et al., "Digital PCR.", Proc Natl Acad Sci US A 96: 9236-9241, 1999.
Vogelstein et al., "The Path to Cancer—Three Strikes and You're Out", N Engl J Med 3 73: 1895-1898, 2015.
Waddell et al., "Whole genomes redefine the mutational landscape of pancreatic cancer", Nature 518(7540):495-501, 2015.
Walsh et al., Coexisting ovarian malignancy in young women with endometrial cancer. Obstetrics and gynecology 106, 693-699, 2005.
Wang et al., "Detection of somatic mutations and HPV in the saliva and plasma of patients with head and neck squamous cell carcinomas.", Science translational medicine 7(293): 293ra104, 2015.
Wang et al., "Detection of tumor-derived DNA in cerebrospinal fluid of patients with primary tumors of the brain and spinal cord.", Proc Natl Acad Sci USA 1 12(31): 9704-9709, 2015.
Wang et al., "Diagnostic potential of tumor DNA from ovarian cyst fluid.", Elife 5, 18 pages, 2016.
Wang et al., "Diagnostic significance of urinary long non-coding PCA3 RNA in prostate cancer", Oncotarget, vol. 8, No. 35, 58577-58586, 2017.
Wang et al., "Evaluation of liquid from the Papanicolaou test and other liquid biopsies for the detection of endometrial and ovarian cancers", Sci. Transl. Med., 10, eaap8796, 9 pages, 2018.
Wang et al., "Extracellular interactions and ligand degradation shape the nodal morphogen gradient", Elife 5: 10.7554/eLife.15 175, 19 pages, 2016.
Wang et al., "Molecular inversion probes: a novel microarray technology and its application in cancer research.", Cancer Genet 205(7-8): 341-55, 2012.

(56) References Cited

OTHER PUBLICATIONS

Wang et al., "Molecular mechanisms and clinical applications of miR-22 in regulating malignant progression in human cancer (Review)", International Journal of Oncology, 50: 345-355, 2017.
Wang et al., "PD-L1 and intratumoral immune response in breast cancer", Oncotarget, vol. 8, (No. 31), pp. 51641-51651, 2017.
Wang et al., "TERT promoter mutations are associated with distant metastases in upper tract urothelial carcinomas and serve as urinary biomarkers detected by a sensitive castPCR.", Oncotarget, 5: 12428-12439, 2014.
Wang et al., "The clinical impact of recent advances in LC-MS for cancer biomarker discovery and verification", Expert Rev Proteomics 13: 99-114, 2016.
Wang et al., "The long non-coding RNA CYTOR drives colorectal cancer progression by interacting with NCL and Sam68", Molecular Cancer, 17: 110, 16 pages, 2018.
Wei et al., "A study of the relationships between oligonucleotide properties and hybridization signal intensities from NimbleGen microarray datasets", Nucleic Acids Res 36(9): 2926-2938, 2008.
Wilcox et al., "Chronic pancreatitis pain pattern and severity are independent of abdominal imaging findings.", Clin Gastroenterol Hepatol 13(3):552-560; quiz e528-559, 2015.
Wong et al., "Chronic Pancreatitis Pain Pattern and Severity are Independent of Abdominal Imaging Findings", Clin. Cancer Res. 15: 2552-2558, 2009.
Woodbury et al., "Elevated HGF Levels in Sera from Breast Cancer Patients Detected Using a Protein Microarray ELISA", J. Proteome Res. 1: 233-237, 2002.
Wu et al., "Endometrial brush biopsy (Tao brush). Histologic diagnosis of 200 cases with complementary cytology: an accurate sampling technique for the detection of endometrial abnormalities.", American journal of clinical pathology 114, 412-418, 2000.
Wu, "Urothelial tumorigenesis: a tale of divergent pathways.", Nat Rev Cancer 5: 713-725, 2005.
Xia et al., "Lapatinib Antitumor Activity Is Not Dependent upon Phosphatase and Tensin Homologue Deleted on Chromosome 10 in ErbB2-Overexpressing Breast Cancers", Cancer Res. 67: 1170-1175, 2007.
Xie et al., "Age-related mutations associated with clonal hematopoietic expansion and malignancies.", Nat Med 20(12): 1472-1478, 2014.
Xie et al., "Lnc-PCDH9-13:1 Is a Hypersensitive and Specific Biomarker for Early Hepatocellular Carcinoma", EBioMedicine, 33, 57-67, 2018.
Xu et al., "Recent advances of highly selective CDK4/6 inhibitors in breast cancer", J Hematol. Oncol. 10(1): 97, 2017.
Yachida et al., "Clinical significance of the genetic landscape of pancreatic cancer and implications for identification of potential long-term survivors.", Clin Cancer Res 18: 6339-6347, 2012.
Yafi et al., "Prospective analysis of sensitivity and specificity of urinary cytology and other urinary biomarkers forbladder cancer.", Urol Oncol 33 :66.e25-66.e3 1, 2015.
Yang et al., "Unusually high incidence of upper urinary tract urothelial carcinoma in Taiwan.", Urology, 59( 5), 681-687, 2002.
Yee et al., "Personalized Therapy Tumor Antigen Discovery for Adoptive Cellular Therapy", Cancer J. 23(2): 144-148, 2016.
Young et al., "Clonal haematopoiesis harbouring AML-associated mutations is ubiquitous in healthy adults.", Nat Commun 7, 12484, 2016.
Yousem et al., "Pulmonary Langerhans Cell Histiocytosis. Profiling of Multifocal Tumors Using Next-Generation Sequencing Identifi es Concordant Occurrence of BRAF V600E Mutations", Chest 143: 1679-1684, 2013.
Yu et al., "LncRNA HCP5 promotes the development of cervical cancer by regulating MACC1 via suppression of microRNA-15a.", Eur. Rev. Med. Pharmacol. Sci., 22: 4812-4819, 2018.
Yu et al., "Long non-coding RNA CACNA1G-AS1 promotes cell migration, invasion and epithelial-mesenchymal transition by HNRNPA2B1 in non-small cell lung cancer", Eur. Rev. Med. Pharmacol. Sci., 22: 993-1002, 2018.

Yun et al., "Biomonitoring of aristolactam-DNA adducts in human tissues using ultra-performance liquid chromatography/ion-trap mass spectrometry,", Chem ResToxicol. 2012 25(5): 1119-31, 2012.
Zack et al., "Pan-cancer patterns of somatic copy No. alteration.", Nature genetics 45: 1134-1140, 2013.
Zaino et al., "Simultaneously Detected Endometrial and Ovarian Carcinomas—A Prospective Clinicopathologic Study of 74 Cases: A Gynecologic Oncology Group Study", Gynecologic oncology 83: 355-362, 2001.
Zamay et al., "Current and Prospective Protein Biomarkers of Lung Cancer", Cancers (Basel), 9(11): 155, 2017.
Zhai et al.,"High-grade serous carcinomas arise in the mouse oviduct via defects linked to the human disease.", The Journal of pathology 243, 16-25, 2017.
Zhang et al., "Analysis of the complex interaction of CDR1as-miRNA-protein and detection of its novel role in melanoma", Oncology Letters, 16: 1219-1225, 2018.
Zhang et al., "LncRNA DQ786243 expression as a biomarker for assessing prognosis in patients with gastric cancer.", Eur. Rev. Med. Pharmacol. Sci., 22: 2304-2309, 2018.
Zhang et al., "LncRNA H19 regulates the expression of its target gene HOXA10 in endometrial carcinoma through competing with miR-612.", Eur. Rev. Med. Pharmacol. Sci., 22: 4820-4827, 2018.
Zhang et al., "The cytomorphological features of low-grade urothelial neoplasms vary by specimen type.", Cancer Cytopathol 124: 552-564, 2016.
Zhao et al., "Histologic follow-up results in 662 patients with Pap test findings of atypical glandular cells: results from a large academic womens hospital laboratory employing sensitive screening methods.", Gynecologic oncology 114, 383-389, 2009.
Zhou et al., "Identifying markers for pancreatic cancer by gene expression analysis.", Cancer Epidemiol Biomarkers Prev 7(2): 109-112, 1998.
Zilbermann et al., "Genome-wide analysis of Dna methylation patterns" Development 134, 2007.
Zimmermann et al., "Digital PCR: a powerful new tool for noninvasive prenatal diagnosis?", Prenat Diagn 28: 1087-1093, 2008.
Zou et al., "More valuable than platinum: first-line pembrolizumab in advanced stage non-small-cell lung cancer", Ann Oncol 28(4): 685-687, 2017.
ACOG Committee Opinion: No. 280, Dec. 2002. "The role of the generalist obstetrician-gynecologist in the early detection of ovarian cancer.", Obstet Gynecol 100, 1413-1416, 2002.
ACOG Practice Bulletin. Clinical Management Guidelines for Obstetrician-Gynecologists. No. 60, Mar. 2005, "Pregestational diabetes mellitus.", Obstet Gynecol 105, 675-685,2 005.
Affymetrix Human Genome U133 Plus 2.0 Array, Public on Nov. 7, 2003, Gene Expression Omnibus URL: https://www.ncbi.nlm.nih.gov/geo/query/acc.cgi?acc=GPL570> [Retrieved from the internet Jun. 7, 2018].
American Cancer Society, "Can ovarian cancer be found early?", (Available at http://www.cancer.org/Cancer/OvarianCancer/DetailedGuide/ovariancancer-detection).
Arbyn et al., "European Guidelines for Quality Assurance in Cervical Cancer Screening. Second edition—summary document", Ann Oncol 21, 448-458 2010.
Australian Office Action in Australian Application No. 2017203206, dated Jan. 23, 2018.
Bandiera et al., "Cancer antigen 125, human epididymis 4, kallikrein 6, osteopontin and soluble mesothelin-related peptide immunocomplexed with immunoglobulin Min epithelial ovarian cancer diagnosis.", Clinical chemistry and laboratory medicine: CCLM I FESCC 51, 1815-1824, 2013.
Barollo et al., "Prevalence, tumorigenic role, and biochemical implications of rare BRAF alterations", Thyroid: offical journal of the american thyroid association 24, 809-819, 2014.
Barrow et al., "Cumulative lifetime incidence of extracolonic cancers in Lynch syndrome: a report of 121 families with proven mutations.", Clin. Genet. 75, 141-149, 2009.
Bashashati et al., "Distinct evolutionary trajectories of primary high-grade serous ovarian cancers revealed through spatial mutational profiling.", The Journal of pathology, 231:21-34, 2013.

(56) References Cited

OTHER PUBLICATIONS

Bast et al., "A radioimmunoassay using a monoclonal antibody to monitor the course of epithelial ovarian cancer", The New England journal of medicine 309, 883-887, 1983.
Bell et al., "Integrated genomic analyses of ovarian carcinoma.", Nature 474, 609-615, 2011.
Bertotti et al., "The genomic landscape of response to EGFR blockade in colorectal cancer.", Nature, 526: 263-7, 2015.
Bowtell et al., "Rethinking ovarian cancer II: reducing mortality from high-grade serous ovarian cancer.", Nature reviews Cancer, 15: 668-79, 2015.
Bray et al., "Global estimates of cancer prevalence for 27sites in the adult population in 2008.", Int. J. Cancer, 2012.
Bristow et al., "Survival effect of maximal cytoreductive surgery for advanced ovarian carcinoma during the platinum era: a meta-analysis." J. Clin. Oncol. 20, 1248-1259, 2002.
Buys et al., "Ovarian cancer screening in the Prostate, Lung, Colorectal and Ovarian (PLCO) cancer screening trial: findings from the initial screen of a randomized trial", American journal of obstetrics and gynecology 193, 1630-1639, 2005.
Buys et al., Effect of screening on ovarian cancer mortality: the Prostate, Lung, Colorectal and Ovarian (PLCO) Cancer Screening Randomized Controlled Trial. JAMA 305, 2295-2303, 2011.
Byron et al., "FGFR2 mutations are rare across histologic subtypes of ovarian cancer," Gynecologic Oncology 117, 125-129, 2010.
Canger Genome Atlas Research Network, "Integrated genomic analyses of ovarian carcinoma.", Nature, 474: 609-15, 2011.
Carlson et al., "Screening for ovarian cancer.", Ann. Intern. Afrd. 121, 124-132, 1994.
Cass et al., BRCA-mutation-associated fallopian tube carcinoma: a distinct clinical phenotype? Obstetrics and Gynecology 106: 1327-34, 2005.
Chang et al., "The clinical utility of endoscopic ultrasound-guided fine-needle aspiration in the diagnosis and staging of pancreatic carcinoma.", Gastrointestinal endoscopy 45, 387-393, 1997.
Cheng et al., "Molecular genetic analysis of ovarian serous cystadenomas", Laboratory investigation; a journal of technical methods and pathology 84, 778-784, 2004.
Chinese Office Action dated Mar. 3, 2017 in related Chinese Application No. 201380068411.8.
Christensen et al., "Functional ovarian cysts in premenopausal and gynecologically healthy women", Contraception 66, 153-157, 2002.
Cobb et al., "Adenocarcinoma of Mullerian origin: review of pathogenesis, molecular biology, and emerging treatment paradigms" Gynecologic Oncology Research and Practice, May 12, 2015 (online), vol. 5, pp. 1-16.
Conner et al., "Outcome of unexpected adnexal neoplasia discovered during risk reduction salpingo-oophorectomy in women with germ-line BRCA1 or BRCA2 mutations.", Gynecol Oncol 132: 280-6, 2014.
Cooper et al., "Endometrial sampling techniques in the diagnosis of abnormal uterine bleeding.", Obstet Gynecol Clin North Am 27, 235-244, 2000.
Cruz et al., "Absence of BRAF and NRAS mutations in uveal melanoma", Cancer research 63, 5761-5766, 2003.
Davies et al., "Mutations of the BRAF gene in human cancer", Nature 417, 949-954, 2002.
Demirol et al., "Effect of endometrioma cystectomy on IVF outcome: a prospective randomized study", Reproductive biomedicine online 12, 639-643, 2006.
Desimone et al., "Rate of pathology from atypical glandular cell Pap tests classified by the Bethesda 2001 nomenclature.", Obstet Gynecol 107, 1285-1291, 2006.
Dinkelspiel et al., "Long-term mortality among women with epithelial ovarian cancer.", Gynecologic oncology 138: 421-8, 2015.
Duke et al., "Transvaginal aspiration of ovarian cysts: long-term follow-up", Cardiovascular and interventional radiology 29, 401-405, 2006.

Eberle et al., "Immunoguided laser assisted microdissection techniques for DNA methylation analysis of archival tissue specimens.", The Journal of molecular diagnostics: JMD 12: 394-401, 2010.
Elmasry et al., "Genetic mutations in gynaecological cancers," Reviews in Gynaecological and Preinatal Practice, vol. 6, No. 3-4, pp. 115-125, 2006.
Eloubeidi et al., "Endoscopic ultrasound-guided fine needle aspiration biopsy of patients with suspected pancreatic cancer: diagnostic accuracy and acute and 30-day complications.", The American journal of gastroenterology 98, 2663-2668, 2003.
Ernani et al., "Agilent's SureSelect Target Enrichment System: Brining Cost and Process Efficiency to Next- Generation Sequencing," Agilent Technologies—Product Notes, pp. 1-8, 2009.
European Office Action issued in related European Application No. 13851273.6, dated Apr. 19, 2017.
Extended European Search Report issued in related European Application No. 13851273.6, dated Jun. 1, 2016.
Falconer et al., "Ovarian cancer risk after salpingectomy: a nationwide population-based study.", J. Natl. Cancer Inst., 107,vol. 2, 2015.
Ferlay et al., "Cancer incidence and mortality patterns in Europe: estimates for 40 countries in 2012.", European Journal of cancer 49: 1374-403, 2013.
Forbes et al., "COSMIC: mining complete cancer genomes in the Catalogue of Somatic Mutations in Cancer.", Nucleic Acids Res 39, D945-950, 2011.
Frossard et al., "Performance of endosonography-guided fine needle aspiration and biopsy in the diagnosis of pancreatic cystic lesions", The american journal of gastroenterology 98, 1516-1524, 2003.
Geier et al., "Clinical evaluation of atypical glandular cells of undetermined significance.", Am. J. Obstet. Gynecol. 184, 64-69, 2001.
Grisham et al., "BRAF mutation is associated with early stage disease and improved outcome in patients with low-grade serous ovarian cancer", Cancer 119, 548-554, 2013.
Gunderson et al., "Oncologic and reproductive outcomes with progestin therapy in women with endometrial hyperplasia and grade 1 adenocarcinoma: a systematic review," Gynecol Oncol 125, 477-482, 2012.
Haber et al., "Blood-based analyses of cancer: circulating tumor cells and circulating tumor DNA.", Cancer discoveiy 4: 650-61, 2014.
Hamilton et al., "Uterine papillary serous and clear cell carcinomas predict for poorer survival compared to grade 3 endometrioid corpus cancers.", Br. J. Cancer 94, 642-646, 2006.
Havrilesky et al., "Predictors of clinical outcomes in the laparoscopic management of adnexal masses.", Obstetrics and gynecology 102, 243-251, 2003.
He et al., "IgH gene rearrangements as plasma biomarkers in Non-Hodgkin's lymphoma patients.", Oncotarget 2, 178-185, 2011.
Hellstrom et al., "The HE4 (WFDC2) protein is a biomarker for ovarian carcinoma", Cancer research 63, 3695-3700, 2003.
Hennessy et al., "Ovarian cancer," Lancet, vol. 374, Oct. 17, 2009.
Hilgeret al., "Laparoscopic management of the adnexal mass.", Clinical obstetrics and gynecology 49, 535-548, 2006.
Howlader et al., SEER Cancer Statistics Review, 1975-2009, National Cancer Institute Bethesda, MD, 2012.
Huntsman et al. "MLL2, the second human homolog of the *Drosophila* trithorax gene, maps to 19q13.1 and is amplified in solid tumor cell lines," Oncogene, 18, 7975-7984, 1999.
Ikediobi et al., "Mutation analysis of 24 known cancer genes in the NCI-60 cell line set,", Molecular Cancer Therapeutics, 5(11), 2006.
Insinga et al., "Diagnoses and outcomes in cervical cancer screening: a population-based study.", Am. J. Obstet. Gynecol. 191, 105-113, 2004.
International Preliminary Report on Patentability issued in PCT/US2013/065342, dated May 5, 2015, 7 pages.
International Search Report and Written Opinion for PCT/US2013/065342, dated Apr. 1, 2014.
International Search Report and Written Opinion in International Application No. PCT/US2016/046453, dated Nov. 1, 2016, 11 pages.

(56) References Cited

OTHER PUBLICATIONS

Jacobs et al., "Ovarian cancer screening and mortality in the UK Collaborative Trial of Ovarian Cancer Screening UKCTOCS): a randomised controlled trial.", Lancet 387: 945-956, 2016.
Japanese Office Action issued in related Japanese Application No. 201380068411.8, dated Apr. 19, 2016.
Jones et al., "Comparative lesion sequencing provides insights into tumor evolution.", Proceedings of the National Academy of Sciences of the United States of America 105: 4283-8, 2008.
Jones et al., "Frequent mutations of chromatin remodeling gene ARID1A in ovarian clear cell carcinoma.", Science 330, 228-231, 2010.
Jones et al., "Low-grade serous carcinomas of the ovary contain very few point mutations", The Journal of pathology 226, 413-420, 2012.
Jones et al., "Personalized genomic analyses for cancer mutation discovery and interpretation.", Science translational medicine, 7: 283ra53, 2015.
Kang et al., "Inverse correlation between RASSF1A hypermethylation, KRAS and BRAF mutations in cervical adenocarcinoma," Gynecology Oncology, 105, 662-666, 2007.
Karst et al., "Ovarian cancer pathogenesis: a model in evolution.", Journal of oncology 932371, 13 pages, 2010.
Kauff et al., "Risk-reducing salpingooophorectomy in women with a BRCA1 or BRCA2 mutation.", The New England journal of medicine, 346: 1609-15, 2002.
Kim et al., "Impact of intraoperative rupture of the ovarian capsule on prognosis in patients with early-stage epithelial ovarian cancer: a meta-analysis.", European journal of surgical oncology : the journal of the European Society of Surgical Oncology and the British Association of Surgical Oncology 39, 279-289, 2013.
Kinde et al., 'Evaluation of DNA from the Papanicolaou test to detect ovarian and endometrial cancers' Science Translational Medicine. vol. 5, Issue 167, Article No. 164ra, pp. 1-10, 2013.
Kindelberger et al., "Intraepithelial carcinoma of the fimbria and pelvic serous carcinoma: Evidence for a causal relationship,", The American journal of surgical pathology 31: 161-9, 2007.
Kristjansdottir et al., "Ovarian cyst fluid is a rich proteome resource for detection of new tumor biomarkers", Clinical Proteomics, vol. 9, internal pp. 1-9, 2012.
Kristjansdottir et al., "Potential tumor biomarkers identified in ovarian cyst fluid by quantitative proteomic analysis, iTRAQ,", Clinical proteomics 10, 4, 2013.
Kuhn et al, "Identification of Molecular Pathway Aberrations in Uterine Serous Carcinoma by Genome-wide Analyses," Journal of the National Cancer Institute, vol. 104, No. 19, Aug. 23, 2012, pp. 1503-1513.
Kuhn et al., "TP53 mutations in serous tubal intraepithelial carcinoma and concurrent pelvic high-grade serous carcinoma-evidence supporting the clonal relationship of the two lesions.", The Journal of pathology, 226:421-6, 2012.
Kurman et al., "Molecular pathogenesis and extraovarian origin of epithelial ovarian cancer—Shilling the paradigm," Human Pathology, 42, 918-931, 2011.
Kurman et al., "The origin and pathogenesis of epithelial ovarian cancer: a proposed unifying theoiy", The American journal of surgical pathology 34,433-443, 2010.
Kwon et al., "Prophylactic salpingectomy and delayed pophorectomy as an alternative for BRCA mutation carriers.", Obstetrics and gynecology, 121:14-24, 2013.
Lee et al., "A candidate precursor to serous carcinoma that originates in the distal fallopian tube", The journal of pathology 211, 26-35, 2007.
Levanon et al., "New insights into the pathogenesis of serous ovarian cancer and its clinical impact.", Journal of clinical oncology : official journal of the American Society of Clinical Oncology, 26: 5284-93, 2008.
Levine et al., "Management of asymptomatic pvarian and other adnexal cysts imaged at US: Society of Radiologists in Ultrasound Consensus Conference Statement", Radiology 256, 943-954, 2010.
Lin et al., "Thyroid cancer in the thyroid nodules evaluated by ultrasonography and fine-needle aspiration cytology", Thyroid: official journal of the american thyroid association 15, 708-717, 2005.
Lindor et al., Press, "Recommendations for the care of individuals with an inherited predisposition to Lynch syndrome: a systematic review.", JA,HA 296, 1507-1517, 2006.
Loh et al., "Ovarian response after laparoscopic ovarian cystectomy for endometriotic cysts in 132 monitored cycles", Fertility and sterility 72, 316-321, 1999.
Longacre et al., "Recommendations for the reporting of fallopian tube neoplasms.", Hum Pathol., 38: 1160-3, 2007.
Malpica et al., "Grading ovarian serous carcinoma using a two-tier system," Am. J. Surg. Pathol. 28, 496-504, 2004.
Marques et al., A"typical glandular cells and cervical cancer: systematic review.", Rev Assoc Af ed Bras 57, 234-238, 2011.
Martinez-Onsurbe et al., "Aspiration cytology of 147 adnexal cysts with histologic correlation", Acta. Cytologica 45, 941-947, 2001.
Mayr et al., "KRAS and BRAF mutations in ovarian tumors: a comprehensive study of invasive carcinomas, borderline tumors and extraovarian implants", Gyencologic oncology 103, 883-887, 2006.
Mayrand et al., "Human papillomavirus DNA versus Papanicolaou screening tests for cervical cancer,", N. Engl. J. Med. 357, 1579-1588, 2007.
McAlpine et al., "Opportunistic salpingectomy: uptake, risks, and complications of a regional initiative for ovarian cancer prevention.", American journal of obstetrics and gynecology 210: 471 e1-11, 2014.
Mcdaniel et al., "Next-Generation Sequencing of Tubal Intraepithelial Carcinomas." JAMA oncology 1: 1128-32, 2015.
Medeiros et al., "The tubal fimbria is a preferred site for early adenocarcinoma in women with familial ovarian cancer syndrome.", The American journal, vol. 30, issue 2, pahes 230-236, 2006.
Meden et al., "CA 125 in benign gynecological conditions.", Int J Biol Alarkers 13, 231-237, 1998.
Menon et al., "Ovarian cancer screening-current status, future directions.", Gynecologic oncology 132: 490-5, 2014.
Mitchell et al., "Accuracy and survival benefit of cytological prediction of endometrial carcinoma on routine cervical smears.", Int J Gynecol Pathol 12, 34-40, 1993.
Moran et al., "Cytologic examination of ovarian cyst fluid for the distinction between benign and malignant tumors", Obstetrics and gynecology 82, 444-446, 1993.
Murtaza et al., "Non-invasive analysis of acuired resistance to cancer therapy by sequencing of plasma DNA", Nature 497, 108-112, 2013.
Naucler et al.,"Human papillomavirus and Papanicolaou tests to screen for cervical cancer.", N Engl J 1\fed 357, 1589-1597, 2007.
Newman et al., "An ultrasensitive method for quantitating circulating tumor DNA with board patient coverage", Nature medicine 20, 548-554, 2014.
Ngamruengphong et al., "Preoperative endoscopic ultrasound-guided fine needle aspiration does not impair survival of patients with resected pancreatic cancer,", Gut, 2015, vol. 64, No. 7.
Nik et al., "Origin and pathogenesis of pelvic (ovarian, tubal, and primary peritoneal) serous carcinoma.", Annual review of pathology 9: 27-45, 2014.
Niknafs et al., SubClonal Hierarchy Inference from Somatic Mutations: Automatic Reconstruction of Cancer Evolutionary Trees from Multi-region Next Generation Sequencing. PLoS computational biology, 11: el004416, pp. 1-26, 2015.
Oda et al., "High Frequency of Coexistent Mutations of PIK3CA and PTEN Genes in Endometrial Carcinoma," Cancer Research, vol. 65, No. 23, pp. 10669-10673, 2005.
Parker et al., "Ovarian conservation at the time of hysterectomy and long-term health outcomes in the nurses' health study.", Obstetrics and gynecology, 113: 1027-37, 2009.
Partridge et al., "Results from four rounds of ovarian cancer screening in a randomized trial.", Obstet Gynecol 113, 775-782, 2009.
Patch et al., "Whole-genome characterization of chemoresistant ovarian cancer.", Nature, 521: 489-94, 2015.

(56) References Cited

OTHER PUBLICATIONS

Pavlik et al., "Frequency and diposition of ovarian abnormalities followed with serial transvaginal ultrasonography", Obstetrics and gynecology 122, 210-217, 2013.
Pecorelli, "Revised FIGO staging for carcinoma of the vulva, cervix, and endometrium.", Int J Gynaecol Obstet 105, 103-104, 2009.
Perets et al., "It's Totally Tubular . . . Riding The New Wave of Ovarian Cancer Research.", Cancer research, 76: 10-7, 2016.
Perets et al., "Transformation of the fallopian tube secretory epithelium leads to high-grade serous ovarian cancer in Brca;Tp53;Pten models.", Cancer cell, 24: 751-65, 2013.
Piek et al., "BRCA1/2-related ovarian cancers are of tubal origin: a hypothesis.", Gynecologic oncology, 90: 491, 2003.
Piek et al., "Dysplastic changes in prophylactically removed Fallopian tubes of women predisposed to developing ovarian cancer.", The Journal of pathology, 195: 451-6, 2001.
Qiu et al., "No evidence of clonal somatic genetic alterations in cancer-associated fibroblasts from human breast and ovarian carcinomas.", Nature Genetics, vol. 40, pp. 650-655, 2008.
Rago, et al., "Serial assessment of human tumor burdens in mice by the analysis of circulating DNA.", Cancer Res 67, 9364-9370, 2007.
Rebbeck et al., "Prophylactic oophorectomy in Carriers of BRCA 1 or BRCA2 mutations.", The New England journal of medicine, 346: 1616-22, 2002.
Ries et al., SEER Survival Afonograph: Cancer Survival Among Adults: US Seer Program, 1988-2001, Patient and Tumor Characteristics (NIH Pub. No. 07-6215. National Cancer Institute, Bethesda, MD, 2007).
Roh et al., "High-grade fimbrial-0varian carcinomas are unified by altered p53, PTEN and PAX2 expression,", Modem pathology, 23: 1316-24, 2010.
Rozen et al., "Primer3 on the WWW for general users and for biologist programmers.", Methods Afol Biol 132, 365-386, 2000.
Sams et al.., "Liquid-based Papanicolaou tests in endometrial carcinoma diagnosis. Performance, error root cause analysis, and quality improvement", Am J Clin Pathol 137, 248-254, 2012.
Schmeler et al., "Neoadjuvant chemotherapy for low-grade serous carcinoma of the ovary or peritoneum", Gynecologic oncology 108, 510-514, 2008.
Schorge et al., "ThinPrep detection of cervical and endometrial adenocarcinoma: a retrospective cohort study.", Cancer 96: 338-43, 2002.
Screening for ovarian cancer: recommendation statement. U.S. Preventive Services Task Force. Am Fam Physician 71, 759-762, 2005.
Sharpless et al., "Dysplasia associated with atypical glandular cells on cervical cytology.", Obstet Gynecol 105, 494-500, 2005.
Sherman et al., "Survival amound women with borderline ovarian tumors and ovarian carcinoma: a population-based analysis", Cancer 100, 1045-1052, 2004.
Shih et al., "Risk factors for recurrence of ovarian boderline tumors", Gynecologic oncology 120, 480-484, 2011.
Siegel et al., Cancer statistics, 2015, CA: a cancer journal for clinicians, 65:5-29, 2015.
Singer et al., "Mutations in BRAF and KRAS characterize the development of low-grade ovarian serous carcinoma", Journal of National Cancer Institute, vol. 95, No. 6, pp. 484-486, 2003.
Smith et al.,"Transvaginal ultrasound for identifying endometrial abnormality.", Acta Obstet Gynecol Scand 70, 591-594, 1991.
Suh et al., Major clinical research advances in gynecologic cancer in 2011, Journal of Gynecologic Oncology, vol. 23, No. 1, pp. 53-64, 2012.
Sundfeldt et al., "Specific mutant tumor DNA can be detected in ovarian cystic fluid of an unknown ovarian tumor cyst", In: The American Association for Cancer Research, 2015, abstract #2839.
Tran et al., "Tract embolization with gelatin sponge slurry for prevention of pneumothorax after percutaneous computed tomography-guided lung biopsy.", Cardiovascular and interventional radiology 37, 1546-1553, 2014.

Trant et al., "Cancer of the Uterus: The Vaginal Smear in Its Diagnosis.", Cali. West. Med. 59, 121-122, 1943.
Tsang et al., "KRAS (but not BRAF) mutations in ovarian serous borderline tumour are assocaited with recurrent low-grade serous carcinoma", The Journal of pathology 231, 449-456, 2013.
Tsang et al., "Ultrasound-guided plugged percutaneous biopsy of solid organs in patients with bleeding tendencies.", Hong Kong Medical Journal, 20, 107-112, 2014.
Ueland et al., "Effectiveness of a multivariate index assay in the preoperative assessment of ovarian tumors.", Obstetrics and gynecology 117, 1289-1297, 2011.
Van Nagell et al., "Ovarian cancer screening with annual transvaginal sonography: findings of 25,000 women screened.", Cancer 109, 1887-1896, 2007.
Vogelstein et al., "Cancer genes and the pathways they control,", Nat. Med. 10, 789-799, 2004.
Vogelstein et al., "Cancer genome landscapes", Science 339, 1546-1558, 2013.
Volpe et al., "Techniques, safety and accuracy of sampling of renal tumors by fine needle aspiration and core biopsy", The journal of urology 178, 379-386, 2007.
Wu et al., "Recurrent GNAS mutations define an unexpected pathway for pancreatic cyst development", Sci Transl Afed 3, 92ra66, 2011.
Wu et al., "Whole-exome sequencing of neoplastic cysts of the pancreas reveals recurrent mutations in components of ubiquitin-dependent pathways", PNAS 108, 21188-21193, 2011.
Yachida et al., "Distant metastasis occurs late during the Jenetic evolution of pancreatic cancer,", Nature, 467: 1114-7, 2010.
Yamada et al., "It is possible to diagnose malignancy from fluid in cystic ovarian tumors?", European journal of obstetrics, gynecology, and reproductive biology 171, 96-100, 2013.
Zhang "Study of Use of Liquid-based Cytologic Test in Cervical Cancer and Endometrial Carcinoma Screening," China Master Dissertations Full-text Database, No. 8, pp. 4-28, 2005.
"Nextera XT DNA Sample Preparation Guide," Illumina, Oct. 1, 2012 (Oct. 1, 2012), Part# 15031942, Rev. C, pp. 1-48. Retrieved from the Internet:<http://cmore.soest.hawaii.edu/summercourse/2015/documents/Metagenomics_06-22/nextera_xt_sample_preparation_guide_15031942_c.pdf> on Sep. 19, 2010 (Sep. 19, 2010).
"Alizadeh et al., ""The Lymphochip: A Specialized cDNA Microarray for the Genomic-scale Analysis of Gene Expression in Normal, and Malignant Lymphocytes."" Cold Spring Harbor Symposia on Quantitative Biology, 1999, vol. LXIV:71-78".
Beers et al., "Array-CGH and breast cancer," Breast Cancer Res., 2006, 8(3):210, 10 pages.
Bettegowda et al. "Detection of circulating tumor DNA in early- and late-stage human malignancies," Sci Transl Med, 2014, 6(224): 1-25.
Cancer.gov [online], "NCI Dictionary of Cancer Terms, Definition of Biomarker," available on or before Apr. 5, 2018, [retrieved on Feb. 26, 2020], retrieved from: URL<https://www.cancer.gov/publications/dictionaries/cancer-terms/def/biomarker>, 1 page.
Castelo-Branco et al., "Methylation of the TERT promoter and risk stratification of childhood brain tumours: an integrative genomic and molecular study," Lancet Oncol., 2013, 14(6):534-542.
Color Hereditary Cancer Test, "A pathogenic mutation was identified in tire BRCA1 gene," tm Clinical Grade testing (www.color.com), 2015, 1-12.
"Cunningham et al., ""Cetuximab Monotherapy and Cetuximab plus Irinotecan in Irinotecan-Refractory Metastatic Colorectal Cancer, N. Engl. J. Med., 2004, 351(4):337-345".
Eckert et al., "Genomics of Ovarian Cancer Progression Reveals Diverse Metastatic Trajectories Including Intraepithelial Metastasis to the Fallopian Tube," Cancer Discov., 2016, 6(12): 1342-1331.
Gardner et al., "Evaluation of a 27-gene inherited cancer panel across 630 consecutive patients referred fortesting in a clinical diagnostic laboratory," Hereditary Cancer in Clinical Practice, 2018, 16(1):1-10.
GenBank Accession No. NM_ 006218, "*Homo sapiens* phosphatidylinositol-4,5-bisphosphate 3-kinase catalytic subunit alpha (PIK3CA), mRNA," Feb. 16, 2020, 7 pages.

(56) References Cited

OTHER PUBLICATIONS

GenBank Accession No. NM_ 058197, "*Homo sapiens* cyclin dependent kinase inhibitor 2A (CDKN2A), transcript variant 3, mRNA," Dec. 29, 2019, 5 pages.
GenBank Accession No. NM_000546. "*Homo sapiens* tumor protein p53 (TP53), transcript variant 1, mRNA," Feb. 13, 2020, 11 pages.
GenBank Accession No. NM_001126112, "*Homo sapiens* tumor protein p53 (TP53), transcript variant 2, mRNA," Dec. 28, 2019, 11 pages.
GenBank Accession No. NM_001126113, "*Homo sapiens* tumor protein p53 (TP53), transcript variant 4, mRNA," Dec. 8, 2019, 6 pages.
GenBank Accession No. NM_001126114, "*Homo sapiens* tumor protein p53 (TP53), transcript variant 3, mRNA," Dec. 29, 2019, 9 pages.
GenBank Accession No. NM_001276761, "*Homo sapiens* tumor protein p53 (TP53), transcript variant 2, mRNA," Dec. 23, 2019, 5 pages.
Gudmundsson et al. "Genome-Wide Association and Replication Studies Identify Four Variants Associated with Prostate Cancer Susceptibility," Nat. Genet. 2009 41:1122-6.
Haber et al. "Blood-based analyses of cancer: circulating tumor cells and circulating tumor DNA," Cancer Discov, 2014, 4(6):650-661.
Heitzer et al.. "Current and future perspectives of liquid bipsies in genomics-driven oncology", Nature Reviews Genetics, 2018, 20(2):71-88.
Huber et al., "High-Resolution Liquid Chromatography of DNA Fragments on Non-Porous Poly(Styrene-Divinylbenzene) Particles," Nucleic Acids Res., 1993, 21:1061-6.
International Preliminarv Report on Patentability in PCT Appln. No. PCT/US2018/045669, dated Feb. 11, 2020, 7 pages.
International Search Report and Written Opinion in International Application No. PCT/US2018/030905, dated Oct. 2, 2018, 23 pages.
International Search Report and Written Opinion in International Application No. PCT/US2019/017973, dated May 17, 2019, 7 pages.
International Search Report and Written Opinion in International Application No. PCT/US2020/014172, dated Apr. 30, 2020, 18 pages.
International Search Report and Written Opioni in International Application No. PCT/US2017/061447, dated Feb. 19, 2018, 10 pages.
Jain et al., "Personalized Therapy of Cancer," Textbook of Personalized Medicine, 2015, Chapter 10, pp. 199-381.
June KW, et al. (2007) Clinicopathological aspects of 542 cases of pancreatic cancer: a special emphasis on small pancreatic cancer. J Korean Med Sci 22 Suppl:S79-85.
Kato et al., "A new Packing for Separation of DNA Restriction Fragments by High Performance Liquid Chromatography," J. Biochem, 1984, 95:83-86.
Kinde et al., 'Detection and quantification of rare mutations with massively parallel sequencing', PNAS, 2011, 108(23):9530-9535.
Leary et al. "Detection of chromosomal alterations in the circulation of cancer patients with whole-genome sequencing," Sci Transl Med, 2012, 4(162): 1-21.
Martinez et al., ""Computational optimisation of targeted DNA sequencing for cancer detection,"" Sci. Rep., 2013, 3(3309):sertp03309 1-8.

Newman et al., 'Integrated digital error suppression for improved detection of circulating tumor DNA', Nature Biotechnology; 2016, 34(5):547-555.
Out et al., "Deep Sequencing to Reveal New Variants in Pooled DNA Samples," Hum. Mutat. 2009, 30:1703-1712.
Peng et al., "Targeted Single Primer Enrichment Sequencing with Single End Duplex-UMI," Scientific Reports, 2019, 9:4810, 10 pages.
Peng et al., Reducing amplification artifacts in high multiplex amplicon sequencing by using molecular barcodes, BMC Genomics, 2015, 16(589): 1-12.
"Tabernero et al., ""Dose- and Schedule-Dependent Inhibition of the Mammalian Target of Rapamycin Pathway With Everolimus: A Phase I Tumor Pharmacodynamic Study in Patients With Advanced Solid Tumors,"" J. Clin. Oncol., 2008, 26: 1603-1610".
Turner et al., "Massively parallel exon capture and library-free resequencing across 16 genomes," Nat. Methods, 2009, 6:315-316.
Hannady et al., "Error-correcting barcoded primers for pyrosequencing hundreds of samples in multiplex." Nature Meth., 2007, 5:1-36.
Hannady et al., "Error-correcting barcoded primers for pyrosequencing hundreds of samples in multiplex," Nature Meth., 2007, 5:235-237.
Al-Shannsi et al., "Molecular spectrum of KRAS, NRAS, BRAF, PIK3CA, TP53, and APC somatic gene mutations in Arab patients with colorectal cancer: determination of frequency and distribution pattern," Journal of Gastrointerstinal Oncology, 2016, 7(6):882-902.
Balmain et al., "A model for RAS mutation patterns in cancers: finding the sweet spot.," Nature Reviews, 2018, 18:767-777.
Boland et al., "Clinical next generation sequencing to identify actionable aberrations in a phase I program," Oncotarget, 2015, 6(24):20099-20110.
Douville et al. "Detection of aneuploidy in patients with cancer through amplification of long interspersed nucleotide elements (LINEs)," PNAS, Feb. 2018, 115:8 1871-1876.
Fujii et al., Genomic landscape of upper urinary tract urothelial carcinoma, Eur. Urol., 2017, 16:3:e900.
Giam et al., "Aneuploidy and chromosomal instability in cancer: a jackpot to chaos," Cell Division, May 2015, 10:3.
International Preliminary Report on Patentability in International Appln No. PCT/US2020/014172, dated Jun. 16, 2021, 9 pages.
Izquierdo et al.,"Molecular characterization of upper urinary tract tumors," BJUI, Oct. 2009, 106:868-872.
Kodaz et al., Frequency of RAS Mutations (KRAS, NRAS, HRAS) in Human Solid Cancer, EJMO, 2017, 1(1):1-7.
Marengo et al., "Biomarkers for pancreatic cancer: Recent achievements in proteomics and genomics through classical and multivariate statistical methods," World J. Gastroenterol, 20(37): 13325-13342, Oct. 7, 2014) (Year: 2014).
McConechy et al., "Use of mutation profiles to refine the classification of endometrial carcinomas," J. Path, 2012; 228: 20-30.
Wang et al., "TERT promoter mutations are associated with distant metastases in upper tract urothelial carcinomas and serve as urinary biomarkers detected by a sensitive castPCR." Oncotarget, 2014, 5:23: 12428-12439.
Wang et al., "TERT promoter mutations in renal cell carcinomas and upper tract urothelial carcinomas," 2014, 5:7:1829-1836.
Young et al., Validation of Biomarkers for Early Detection of Pancreatic Cancer: Summary of the Alliance of Pancreatic Cancer Consortia for Biomarkers for Early Detection Workshop., Pancreas, 2018, 47(2):135-141.
Yuan et al., "The genetic difference between Western and Chinese urothelial cell carcinomas: infrequent FGFR3 mutation in Han Chinese patients," Oncotarget, 2016, 7:18:25826-25835.

\* cited by examiner

FIG. 3 (TABLE) 1: PATIENT DEMOGRAPHICS

| ID | CLASSIFICATION | HISTOLOGY | STAGE | HE4 (pmol/L) | CA-125 (U/mL) | AGE AT DIAGNOSIS (YEARS) |
|---|---|---|---|---|---|---|
| OVCYST 001 | NON-NEOPLASTIC | MESOTHELIAL CYST | NA | 62 | 10 | 82 |
| OVCYST 003 | NON-NEOPLASTIC | MESOTHELIAL CYST | NA | 79 | 12 | 81 |
| OVCYST 004 | NON-NEOPLASTIC | MESOTHELIAL CYST; FOLLICULAR CYST | NA | 79 | 12 | 58 |
| OVCYST 005 | NON-NEOPLASTIC | CORPUS LUTEAL CYST | NA | 101 | 13 | 49 |
| OVCYST 006 | NON-NEOPLASTIC | MESOTHELIAL CYST; FOLLICULAR CYST | NA | 45 | 14 | 43 |
| OVCYST 007 | NON-NEOPLASTIC | FOLLICULAR CYST | NA | 44 | 12 | 61 |
| OVCYST 012 | NON-NEOPLASTIC | MUCINOUS CYSTADENOMA AND ENDOMETRIOTIC CYST | NA | 39 | 13 | 46 |
| OVCYST 014 | NON-NEOPLASTIC | MESOTHELIAL CYST | NA | 51 | 19 | 23 |
| OVCYST 016 | NON-NEOPLASTIC | MESOTHELIAL CYST WITH TRANSITIONAL METAPLASIA | NA | 83 | 4 | 69 |
| OVCYST 021 | NON-NEOPLASTIC | MESOTHELIAL CYST | NA | 89 | 7 | 82 |
| OVCYST 002 | BENIGN | SEROUS CYSTADENOMA | NA | 59 | 36 | 16 |
| OVCYST 009 | BENIGN | SEROUS CYSTADENOMA | NA | 178 | 27 | 86 |
| OVCYST 011 | BENIGN | SEROUS CYSTADENOMA | NA | 89 | 16 | 64 |
| OVCYST 008 | BENIGN | SEROUS CYSTADENOFIBROMA | NA | 54 | 4 | 67 |
| OVCYST 013 | BENIGN | SEROUS CYSTADENOMA | NA | 59 | 4 | 70 |
| OVCYST 015 | BENIGN | MUCINOUS CYSTADENOMA | NA | 127 | 52 | 81 |
| OVCYST 017 | BENIGN | SEROUS CYSTADENOFIBROMA | NA | 84 | 25 | 76 |
| OVCYST 018 | BENIGN | SEROUS CYSTADENOMA | NA | 96 | 6 | 50 |
| OVCYST 019 | BENIGN | SEROUS CYSTADENOFIBROMA | NA | 52 | 11 | 51 |

Fig. 3A

FIG. 3 (TABLE 1): PATIENT DEMOGRAPHICS

| | | | | |
|---|---|---|---|---|
| OVCYST 019 | BENIGN | SEROUS CYSTADENOFIBROMA | NA | 52 | 11 | 51 |
| OVCYST 020 | BENIGN | SEROUS CYSTADENOFIBROMA | NA | 62 | 22 | 55 |
| OVCYST 044 | BENIGN | SEROUS CYSTADENOFIBROMA | NA | 59 | 79 | 52 |
| OVCYST 056 | BENIGN | SEROUS CYSTADENOFIBROMA | NA | 277 | 62 | 82 |
| OVCYST 042 | BORDERLINE | ATYPICAL PROLIFERATIVE SEROUS TUMOR | IIIB | 52 | 255 | 40 |
| OVCYST 043 | BORDERLINE | ATYPICAL PROLIFERATIVE SEROUS TUMOR | IIIA | 71 | 47 | 56 |
| OVCYST 045 | BORDERLINE | ATYPICAL PROLIFERATIVE SEROUS TUMOR | IA | 111 | 613 | 42 |
| OVCYST 047 | BORDERLINE | ATYPICAL PROLIFERATIVE SEROUS TUMOR | IA | 76 | 251 | 51 |
| OVCYST 048 | BORDERLINE | ATYPICAL PROLIFERATIVE SEROUS TUMOR | IA | 105 | 39 | 65 |
| OVCYST 049 | BORDERLINE | ATYPICAL PROLIFERATIVE SEROUS TUMOR | IB | 62 | 52 | 46 |
| OVCYST 050 | BORDERLINE | ATYPICAL PROLIFERATIVE SEROUS TUMOR | IC | 55 | 21 | 46 |
| OVCYST 051 | BORDERLINE | ATYPICAL PROLIFERATIVE SEROUS TUMOR | IB | 150 | 189 | 53 |
| OVCYST 053 | BORDERLINE | ATYPICAL PROLIFERATIVE SEROUS TUMOR | IA | 71 | 425 | 35 |
| OVCYST 054 | BORDERLINE | ATYPICAL PROLIFERATIVE SEROUS TUMOR | IIIC | 96 | 98 | 47 |
| OVCYST 055 | BORDERLINE | ATYPICAL PROLIFERATIVE SEROUS TUMOR | IIIC | 88 | 134 | 59 |
| OVCYST 057 | BORDERLINE | ATYPICAL PROLIFERATIVE SEROUS TUMOR | IA | 77 | 185 | 45 |
| OVCYST 058 | BORDERLINE | ATYPICAL PROLIFERATIVE SEROUS TUMOR | IA | 72 | 95 | 28 |
| OVCYST 059 | BORDERLINE | ATYPICAL PROLIFERATIVE SEROUS TUMOR | IIIB | 121 | 28 | 38 |
| OVCYST 060 | BORDERLINE | ATYPICAL PROLIFERATIVE SEROUS TUMOR | IA | 87 | 93 | 47 |
| OVCYST 061 | BORDERLINE | ATYPICAL PROLIFERATIVE SEROUS TUMOR | IA | 109 | 50 | 38 |
| OVCYST 062 | BORDERLINE | ATYPICAL PROLIFERATIVE SEROUS TUMOR | IA | 69 | 76 | 47 |
| OVCYST 063 | BORDERLINE | ATYPICAL PROLIFERATIVE SEROUS TUMOR | IA | 126 | 600 | 78 |
| OVCYST 064 | BORDERLINE | ATYPICAL PROLIFERATIVE SEROUS TUMOR | IIIC | 119 | 653 | 42 |

Fig. 3B

FIG. 3 (TABLE 1): PATIENT DEMOGRAPHICS

| | | | | | | |
|---|---|---|---|---|---|---|
| OVCYST 065 | BORDERLINE | ATYPICAL PROLIFERATIVE SEROUS TUMOR | IC | 84 | 74 | 25 |
| OVCYST 066 | BORDERLINE | ATYPICAL PROLIFERATIVE SEROUS TUMOR | IA | NA | 20 | 59 |
| OVCYST 067 | BORDERLINE | ATYPICAL PROLIFERATIVE ENDOMETRIOID TUMOR | IB | 73 | 44 | 76 |
| OVCYST 069 | BORDERLINE | ATYPICAL PROLIFERATIVE SEROUS TUMOR | IIIA | 123 | 8 | 76 |
| OVCYST 072 | BORDERLINE | ATYPICAL PROLIFERATIVE SEROUS TUMOR | IIIA | 66 | 136 | 50 |
| OVCYST 046 | MALIGNANT (TYPE I) | NON-INVASIVE LOW-GRADE SEROUS CARCINOMA | IB | 53 | 32 | 41 |
| OVCYST 031 | MALIGNANT (TYPE I) | LOW-GRADE SEROUS CARCINOMA | IIIC | 308 | 288 | 55 |
| OVCYST 035 | MALIGNANT (TYPE I) | MIXED EPITHELIAL TUMOR (LOW-GRADE SEROUS AND LOW-GRADE MUCINOUS) | IIIC | 642 | 2315 | 84 |
| OVCYST 036 | MALIGNANT (TYPE I) | ENDOMETRIOID LOW- AND MODERATE-GRADE CARCINOMA | IIIC | 135 | 205 | 63 |
| OVCYST 070 | MALIGNANT (TYPE I) | CLEAR CELL CARCINOMA | IIC | 746 | 726 | 61 |
| OVCYST 071 | MALIGNANT (TYPE I) | LOW-GRADE MUCINOUS CARCINOMA | IA | 52 | 35 | 55 |
| OVCYST 074 | MALIGNANT (TYPE I) | LOW-GRADE ENDOMETRIOID CARCINOMA | IC | 483 | 851 | 81 |
| OVCYST 075 | MALIGNANT (TYPE I) | LOW-GRADE SEROUS CARCINOMA | IIC | 52 | 57 | 52 |
| OVCYST 076 | MALIGNANT (TYPE I) | LOW-GRADE SEROUS CARCINOMA | IIIC | 161 | 146 | 29 |
| OVCYST 077 | MALIGNANT (TYPE I) | LOW-GRADE SEROUS CARCINOMA | IIIC | 286 | 1850 | 75 |
| OVCYST 078 | MALIGNANT (TYPE I) | LOW-GRADE ENDOMETRIOID CARCINOMA | IA | 80 | 22 | 45 |
| OVCYST 079 | MALIGNANT (TYPE I) | LOW-GRADE ENDOMETRIOID CARCINOMA | IC | 784 | 393 | 87 |
| OVCYST 080 | MALIGNANT (TYPE I) | LOW-GRADE SEROUS CARCINOMA | IA | 73 | 30 | 36 |
| OVCYST 022 | MALIGNANT (TYPE II) | HIGH-GRADE SEROUS CARCINOMA | IIIB | 318 | 1953 | 49 |
| OVCYST 023 | MALIGNANT (TYPE II) | HIGH-GRADE SEROUS CARCINOMA | IIIC | 412 | 122 | 85 |
| OVCYST 024 | MALIGNANT (TYPE II) | HIGH-GRADE SEROUS CARCINOMA | IV | 434 | 6548 | 73 |
| OVCYST 025 | MALIGNANT (TYPE II) | HIGH-GRADE SEROUS CARCINOMA | IIIC | 766 | 14880 | 51 |
| OVCYST 026 | MALIGNANT (TYPE II) | HIGH-GRADE SEROUS CARCINOMA | IIIC | 229 | 1068 | 42 |

Fig. 3C

FIG. 3 (TABLE 1): PATIENT DEMOGRAPHICS

| | | | | | |
|---|---|---|---|---|---|
| OVCYST 027 | MALIGNANT (TYPE II) | HIGH-GRADE SEROUS CARCINOMA | IIIC | 590 | 3229 | 63 |
| OVCYST 028 | MALIGNANT (TYPE II) | HIGH-GRADE SEROUS CARCINOMA | IIIC | 335 | 395 | 40 |
| OVCYST 029 | MALIGNANT (TYPE II) | HIGH-GRADE SEROUS CARCINOMA | IIIC | 204 | 685 | 72 |
| OVCYST 032 | MALIGNANT (TYPE II) | HIGH-GRADE SEROUS CARCINOMA | IV | 163 | 136 | 72 |
| OVCYST 033 | MALIGNANT (TYPE II) | HIGH-GRADE SEROUS CARCINOMA | IIIC | 182 | 301 | 54 |
| OVCYST 034 | MALIGNANT (TYPE II) | HIGH-GRADE SEROUS CARCINOMA | IIIC | 1368 | 293 | 69 |
| OVCYST 037 | MALIGNANT (TYPE II) | HIGH-GRADE SEROUS CARCINOMA | IIIC | 326 | 1113 | 67 |
| OVCYST 038 | MALIGNANT (TYPE II) | HIGH-GRADE SEROUS CARCINOMA | IIIC | 1496 | 144 | 65 |
| OVCYST 039 | MALIGNANT (TYPE II) | HIGH-GRADE SEROUS CARCINOMA | IIIC | 347 | 2900 | 57 |
| OVCYST 040 | MALIGNANT (TYPE II) | HIGH-GRADE SEROUS CARCINOMA | IIB | 518 | 103 | 50 |
| OVCYST 041 | MALIGNANT (TYPE II) | HIGH-GRADE SEROUS CARCINOMA | IV | 2604 | 7962 | 63 |
| OVCYST 073 | MALIGNANT (TYPE II) | HIGH-GRADE ENDOMETRIOID CARCINOMA | IA | 245 | 471 | 58 |
| OVCYST 081 | MALIGNANT (TYPE II) | HIGH-GRADE ENDOMETRIOID CARCINOMA | IC | 72 | 8 | 56 |
| *NA = NOT APPLICABLE | | | | | | |

Fig. 3D

FIG. 4 (TABLE 2): MUTATIONS IDENTIFIED IN TUMORS AND CYST FLUIDS

| ID | CYST CLASSIFICATION | CYST DNA (ng) | GENE | TRANSCRIPT | cDNA | PROTEIN | LOCATION | % MUTATION IN TUMOR | % MUTATION IN CYST |
|---|---|---|---|---|---|---|---|---|---|
| OVCYST 001 | NON-NEOPLASTIC | 3 | -- | -- | -- | -- | -- | NO TUMOR AVAILABLE | *-- |
| OVCYST 003 | NON-NEOPLASTIC | 3 | -- | -- | -- | -- | -- | NO TUMOR AVAILABLE | *-- |
| OVCYST 004 | NON-NEOPLASTIC | 24 | -- | -- | -- | -- | -- | NO TUMOR AVAILABLE | -- |
| OVCYST 005 | NON-NEOPLASTIC | 9 | -- | -- | -- | -- | -- | NO TUMOR AVAILABLE | -- |
| OVCYST 006 | NON-NEOPLASTIC | 7 | -- | -- | -- | -- | -- | NO TUMOR AVAILABLE | -- |
| OVCYST 007 | NON-NEOPLASTIC | 140 | -- | -- | -- | -- | -- | NO TUMOR AVAILABLE | -- |
| OVCYST 012 | NON-NEOPLASTIC | 4 | -- | -- | -- | -- | -- | NO TUMOR AVAILABLE | -- |
| OVCYST 014 | NON-NEOPLASTIC | 145 | -- | -- | -- | -- | -- | NO TUMOR AVAILABLE | *-- |
| OVCYST 016 | NON-NEOPLASTIC | 2 | -- | -- | -- | -- | -- | NO TUMOR AVAILABLE | *-- |
| OVCYST 021 | NON-NEOPLASTIC | 1 | -- | -- | -- | -- | -- | NO TUMOR AVAILABLE | -- |
| OVCYST 002 | BENIGN | 117 | -- | -- | -- | -- | -- | NO TUMOR AVAILABLE | -- |
| OVCYST 009 | BENIGN | 63 | -- | -- | -- | -- | -- | NO TUMOR AVAILABLE | -- |
| OVCYST 011 | BENIGN | 17 | -- | -- | -- | -- | -- | NO TUMOR AVAILABLE | -- |
| OVCYST 008 | BENIGN | 62 | -- | -- | -- | -- | -- | NO TUMOR AVAILABLE | -- |

FIG. 4 (TABLE 2): MUTATIONS IDENTIFIED IN TUMORS AND CYST FLUIDS

| | | | | | | | | |
|---|---|---|---|---|---|---|---|---|
| OVCYST 013 | BENIGN | 193 | | | | | NO TUMOR AVAILABLE | --- |
| OVCYST 015 | BENIGN | 95 | --- | | | | NO TUMOR AVAILABLE | --- |
| OVCYST 017 | BENIGN | 98 | --- | | | | NO TUMOR AVAILABLE | --- |
| OVCYST 018 | BENIGN | 20 | --- | | | | NO TUMOR AVAILABLE | --- |
| OVCYST 019 | BENIGN | 28 | --- | | | | NO TUMOR AVAILABLE | --- |
| OVCYST 020 | BENIGN | 185 | --- | | | | NO TUMOR AVAILABLE | --- |
| OVCYST 044 | BENIGN | 124 | --- | | | | NO TUMOR AVAILABLE | --- |
| OVCYST 056 | BENIGN | 26 | --- | | | | NO TUMOR AVAILABLE | --- |
| OVCYST 042 | BORDERLINE | 11321 | BRAF | NM_004333.4 | c.1799T>A | p.V600E | EXON | 48.0% | 0.9% |
| OVCYST 043 | BORDERLINE | 3120 | KRAS | NM_004985.3 | c.183A>C | p.Q61H | EXON | 27.2% | 2.3% |
| OVCYST 045 | BORDERLINE | 24859 | BRAF | NM_004333.4 | c.1799T>A | p.V600E | EXON | 50.0% | 9.0% |
| OVCYST 047 | BORDERLINE | 13586 | BRAF | NM_004333.4 | c.1799T>A | p.V600E | EXON | 43.4% | 8.3% |
| OVCYST 048 | BORDERLINE | 1 | --- | | | | --- | * -- |
| OVCYST 049 | BORDERLINE | 4 | BRAF | NM_004333.4 | c.1799T>A | p.V600E | EXON | 27.6% | 29.4% |
| OVCYST 050 | BORDERLINE | 17928 | BRAF | NM_004333.4 | c.1799T>A | p.V600E | EXON | 17.8% | 0.6% |
| OVCYST 051 | BORDERLINE | 43 | --- | | | | --- | --- |
| OVCYST 053 | BORDERLINE | 7960 | BRAF | NM_004333.4 | c.1799T>A | p.V600E | EXON | 33.2% | 12.6% |
| OVCYST 054 | BORDERLINE | 16986 | KRAS | NM_004985.3 | c.35G>A | p.G12D | EXON | 33.9% | 1.1% |

FIG. 4 (TABLE 2): MUTATIONS IDENTIFIED IN TUMORS AND CYST FLUIDS

| | | | | | | | | |
|---|---|---|---|---|---|---|---|---|
| OVCYST 055 | BORDERLINE | 1751 | KRAS | NM_004985.3 | c.35G>T | p.G12V | EXON | 53.7% | 21.3% |
| OVCYST 057 | BORDERLINE | 14476 | KRAS | NM_004985.3 | c.35G>T | p.G12V | EXON | 46.9% | 1.5% |
| OVCYST 058 | BORDERLINE | 83 | -- | -- | -- | -- | -- | -- | -- |
| OVCYST 059 | BORDERLINE | 956 | BRAF | NM_004333.4 | c.1799T>A | p.V600E | EXON | 45.3% | 2.4% |
| OVCYST 060 | BORDERLINE | 968 | BRAF | NM_004333.4 | c.1799T>A | p.V600E | EXON | 29.3% | 12.6% |
| OVCYST 061 | BORDERLINE | 4350 | KRAS | NM_004985.3 | c.35G>A | p.G12D | EXON | 51.5% | 2.2% |
| OVCYST 062 | BORDERLINE | 9932 | BRAF | NM_004333.4 | c.1799T>A | p.V600E | EXON | 49.0% | 1.8% |
| OVCYST 063 | BORDERLINE | 9180 | KRAS | NM_004985.3 | c.35G>A | p.G12D | EXON | No tumor available | 1.5% |
| OVCYST 064 | BORDERLINE | 7079 | BRAF | NM_004333.4 | c.1799T>A | p.V600E | EXON | 32.0% | 0.6% |
| OVCYST 065 | BORDERLINE | 2156 | BRAF | NM_004333.4 | c.1799T>A | p.V600E | EXON | 35.8% | 20.5% |
| OVCYST 066 | BORDERLINE | 51 | -- | -- | -- | -- | -- | -- | -- |
| OVCYST 069 | BORDERLINE | 50 | BRAF | NM_004333.4 | c.1799T>A | p.V600E | EXON | 28.8% | 7.7% |
| OVCYST 067 | BORDERLINE | 4386 | -- | -- | -- | -- | -- | -- | -- |
| OVCYST 072 | BORDERLINE | 9 | KRAS | NM_004985.3 | c.35G>T | p.G12V | EXON | 49.8% | 4.4% |
| OVCYST 031 | MALIGNANT (TYPE I) | 542 | KRAS | NM_004985.3 | c.35G>A | p.G12D | EXON | 44.5% | 7.3% |
| OVCYST 035 | MALIGNANT (TYPE I) | 138 | BRAF | NM_004333.4 | c.1799_1814TGAAATCTCGATGGAG>A | p.V600_S605>D | EXON | 30.2% | 7.8% |
| OVCYST 036 | MALIGNANT (TYPE I) | 3296 | KRAS | NM_004985.3 | c.35G>A | p.G12D | EXON | 18.2% | 24.2% |
| OVCYST 046 | MALIGNANT (TYPE I) | 53 | -- | -- | -- | -- | -- | -- | -- |

| FIG. 4 (TABLE 2): MUTATIONS IDENTIFIED IN TUMORS AND CYST FLUIDS | | | | | | | | |
|---|---|---|---|---|---|---|---|---|
| **OVCYST 070 | MALIGNANT (TYPE I) | 812 | TP53 | NM_00054 6.5 | c.743G>A | p.R248Q | EXON | 61.0% | 40.3% |
| OVCYST 071 | MALIGNANT (TYPE I) | 2290 | PIK3R1 | NM_18152 3.2 | c.1683_1684insAAA | p.K561_R56 2insK | EXON | 39.7% | 28.7% |
| OVCYST 074 | MALIGNANT (TYPE I) | 90 | TP53 | NM_00054 6.5 | c.833C>A | p.P278H | EXON | 53.2% | 88.4% |
| OVCYST 075 | MALIGNANT (TYPE I) | 836 | -- | -- | -- | -- | -- | -- | -- |
| OVCYST 076 | MALIGNANT (TYPE I) | 547 | KRAS | NM_00498 5.3 | c.35G>A | p.G12D | EXON | 38.1% | 3.3% |
| OVCYST 077 | MALIGNANT (TYPE I) | 14 | -- | -- | -- | -- | -- | -- | -- |
| **OVCYST 078 | MALIGNANT (TYPE I) | 352 | KRAS | NM_00498 5.3 | c.35G>T | p.G12V | EXON | 45.5% | 30.2% |
| | | | TP53 | NM_00054 6.5 | c.584T>C | p.I195T | EXON | 62.6% | 7.4% |
| | | | NRAS | NM_00252 4.4 | c.182A>G | p.Q61R | EXON | 35.6% | 9.1% |
| **OVCYST 079 | MALIGNANT (TYPE I) | 2998 | PTEN | NM_00031 4.4 | c.275A>T | p.D92V | EXON | 61.2% | 0.5% |
| | | | PPP2R1A | NM_01422 5.5 | c.547C>T | p.R183W | EXON | 41.4% | 0.5% |
| OVCYST 080 | MALIGNANT (TYPE I) | 6423 | KRAS | NM_00498 5.3 | c.35G>T | p.G12V | EXON | 39.7% | 0.2% |
| OVCYST 022 | MALIGNANT (TYPE II) | 102 | TP53 | NM_00054 6.5 | c.722delC | p.S241fs | EXON | 54.3% | 28.5% |
| OVCYST 023 | MALIGNANT (TYPE II) | 4554 | TP53 | NM_00054 6.5 | c.175+1G>T | NA | SPLICE SITE | 54.5% | 81.1% |
| OVCYST 024 | MALIGNANT (TYPE II) | 96 | TP53 | NM_00054 6.5 | c.527G>A | p.C176Y | EXON | 69.0% | 69.4% |
| OVCYST 025 | MALIGNANT (TYPE II) | 1709 | TP53 | NM_00054 6.5 | c.991C>T | p.Q331* | EXON | 37.8% | 31.9% |
| OVCYST 026 | MALIGNANT (TYPE II) | 198 | TP53 | NM_00054 6.5 | c.824G>A | p.C275Y | EXON | 75.7% | 88.8% |

Fig. 4E

FIG. 4 (TABLE 2): MUTATIONS IDENTIFIED IN TUMORS AND CYST FLUIDS

| | | | | | | | |
|---|---|---|---|---|---|---|---|
| OVCYST 027 | MALIGNANT (TYPE II) | 257 | TP53 | NM_000546.5 | c.749C>T | p.P250L | EXON | 46.3% | 90.1% |
| OVCYST 028 | MALIGNANT (TYPE II) | 1192 | TP53 | NM_000546.5 | c.979delT | p.Y327fs | EXON | 43.4% | 51.2% |
| OVCYST 029 | MALIGNANT (TYPE II) | 24200 | TP53 | NM_000546.5 | c.803delA | p.N268fs | EXON | 75.8% | 60.3% |
| OVCYST 032 | MALIGNANT (TYPE II) | 222 | TP53 | NM_000546.5 | c.824G>A | p.C275Y | EXON | 69.9% | 69.6% |
| OVCYST 033 | MALIGNANT (TYPE II) | 114 | TP53 | NM_000546.5 | c.844C>T | p.R282W | EXON | 56.4% | 72.1% |
| OVCYST 034 | MALIGNANT (TYPE II) | 1757 | TP53 | NM_000546.5 | c.731G>T | p.G244V | EXON | 58.2% | 30.1% |
| OVCYST 037 | MALIGNANT (TYPE II) | 1900 | TP53 | NM_000546.5 | c.818G>A | p.R273H | EXON | 54.5% | 63.3% |
| OVCYST 038 | MALIGNANT (TYPE II) | 2131 | TP53 | NM_000546.5 | c.376T>A | p.Y126N | EXON | 61.5% | 40.0% |
| OVCYST 039 | MALIGNANT (TYPE II) | 161 | TP53 | NM_000546.5 | c.711G>A | p.M237I | EXON | 35.8% | 31.8% |
| OVCYST 040 | MALIGNANT (TYPE II) | 10340 | TP53 | NM_000546.5 | c.722C>T | p.S241F | EXON | 85.1% | 90.9% |
| OVCYST 041 | MALIGNANT (TYPE II) | 1142 | TP53 | NM_000546.5 | c.818G>A | p.R273H | EXON | 64.5% | 69.3% |
| OVCYST 073 | MALIGNANT (TYPE II) | 5531 | PIK3CA | NM_006218.2 | c.1624G>A | p.E542K | EXON | NO TUMOR AVAILABLE | 30.9% |
| **OVCYST 081 | MALIGNANT (TYPE II) | 19706 | TP53 | NM_000546.5 | c.839G>A | p.R280K | EXON | 44.5% | 3.0% |
| | | | PIK3R1 | NM_181523.2 | c.1372_1377delGAAAAA | p.E458_K459delEK | EXON | 49.3% | 3.7% |

-- INDICATES NO MUTATION DETECTED
* SAMPLES WITH INSUFFICIENT CYST DNA FOR EVALUATION
** PATIENTS WITH TWO MUTATIONS DETECTED

Fig. 5 (Table 3): Detection of tumor-specific mutations in cyst fluid

| | Fraction of Samples Detected (95% confidence interval) | Median Fraction of Mutant Alleles (IQR) | Total # of Samples |
|---|---|---|---|
| Type | | | |
| Non-neoplastic | 0% (0-31%) | 0% (0-0%) | 10 |
| Benign tumor | 0% (0-26%) | 0% (0-0%) | 12 |
| Borderline tumor | 79% (58-93%) | 2.4% (1.5-10.8%) | 24 |
| Type I cancer | 77% (46-95%) | 7.8% (3.3-28.7%) | 13 |
| Type II cancer | 100% (81-100%) | 60.3% (31.3-70.8%) | 18 |
| Cancer Stage | | | |
| Early (I and II) | 82% (48-97%) | 7.4% (3.0-30.9%) | 11 |
| Late (III and IV) | 95% (75-100%) | 51.2% (30.2-69.5%) | 20 |
| Cysts Requiring Surgery | | | |
| No | 0% (0-22%) | 0% (0-0%) | 22 |
| Yes | 85% (73-94%) | 12.6% (2.7-40.2%) | 55 |

Fig. 5

Fig. 6 (Table 4): Multivariate analysis for markers associated with need for surgery

| Criteria | P value |
|---|---|
| Mutation present | <0.001 |
| Serum CA-125 elevated | 0.01 |
| HE4 elevated | 0.92 |
| Cyst DNA amount | 0.69 |

Fig. 6

FIG. 8 (TABLE S1): PRIMER SEQUENCES USED IN MULTIPLEX ASSAY

| GENE | GENOMIC COORDINATES OF AMPLIFIED REGION* | SEQ ID NOs: 1-133 | SEQ ID NOs: 134-266 | AMPLICON LENGTH (bp) |
|---|---|---|---|---|
| | | FORWARD PRIMER | REVERSE PRIMER SEQUENCE | |
| APC | chr5:112173764 - 112173851 | cacacaggaaacagctatgaccatgcaacatgactgtccttt cacca | cgacgtaaaacgacggccagtNNNNNNNNNNNNNNNtagaccaatt ccgcgttctc | 130 |
| APC | chr5:112173892 - 112173980 | cacacaggaaacagctatgaccatgggcaactaccatcca gcaac | cgacgtaaaacgacggccagtNNNNNNNNNNNNNNNNcttctgtcttc ctgagagttatgaa | 134 |
| APC | chr5:112174054 - 112174132 | cacacaggaaacagctatgaccatggtattctaatttgcat aagcataga | cgacgtaaaacgacggccagtNNNNNNNNNNNNNNNtgtgtgacag atgagagaaatgc | 129 |
| APC | chr5:112174225 - 112174298 | cacacaggaaacagctatgaccatgtgatgttatggtaaa agagtca | cgacgtaaaacgacggccagtNNNNNNNNNNNNNNNtgcactatgt attttatgggctaggt | 124 |
| APC | chr5:112174361 - 112174432 | cacacaggaaacagctatgaccatgggatgataatgatgg agaactagatca | cgacgtaaaacgacggccagtNNNNNNNNNNNNNNNgtttgggtct tgccatct | 119 |
| APC | chr5:112174543 - 112174611 | cacacaggaaacagctatgaccatgtgatttgtttctgaac cattg | cgacgtaaaacgacggccagtNNNNNNNNNNNNNNNcctgtttata ctgagagcactgatga | 117 |
| APC | chr5:112174681 - 112174748 | cacacaggaaacagctatgaccatgtttgttggtctctcttct tcttcat | cgacgtaaaacgacggccagtNNNNNNNNNNNNNNNtcaaaatgt aagccagtcttttgtg | 117 |
| APC | chr5:112174823 - 112174895 | cacacaggaaacagctatgaccatgcgttttactctttgt ccag | cgacgtaaaacgacggccagtNNNNNNNNNNNNNNNcgtcatgtgg atcagcctatt | 115 |
| APC | chr5:112175006 - 112175077 | cacacaggaaacagctatgaccatggaaaaacatattgga gtatcttctacaca | cgacgtaaaacgacggccagtNNNNNNNNNNNNNNNccatccaagt tctgcacagagt | 123 |
| APC | chr5:112175182 - 112175258 | cacacaggaaacagctatgaccatgtgctgtgacactgct ggaa | cgacgtaaaacgacggccagtNNNNNNNNNNNNNNNcagacgaca caggaagcaga | 117 |
| APC | chr5:112175343 - 112175422 | cacacaggaaacagctatgaccatgagaatcagcaggca caaag | cgacgtaaaacgacggccagtNNNNNNNNNNNNNNNaacatgagt ggggtctcctg | 120 |
| APC | chr5:112175520 - 112175600 | cacacaggaaacagctatgaccatggctccgttcagagtga accat | cgacgtaaaacgacggccagtNNNNNNNNNNNNNNNaggaggtgg tggaggtgttt | 122 |
| APC | chr5:112175709 - 112175795 | cacacaggaaacagctatgaccatgagccactcaggctgga tgaac | cgacgtaaaacgacggccagtNNNNNNNNNNNNNNNggacctaag caagtcgcagtaa | 129 |
| APC | chr5:112175913 - 112175981 | cacacaggaaacagctatgaccatggggaatgaaacaga atcagagc | cgacgtaaaacgacggccagtNNNNNNNNNNNNNNNtcaatatcat catcatctgaatcattcta | 119 |
| APC | chr5:112176056 - 112176139 | cacacaggaaacagctatgaccatgcaacctgttttgtgat ggtagaag | cgacgtaaaacgacggccagtNNNNNNNNNNNNNNNccatgccaa caaagtcatca | 128 |

FIG. 8 (TABLE S1): PRIMER SEQUENCES USED IN MULTIPLEX ASSAY

| Gene | Location | Forward Primer | Reverse Primer | Size |
|---|---|---|---|---|
| CDKN2A | chr9:21974669-21974742 | cacacaggaaacagctatgaccatgGGGTCGGGTAG AGGAGGTG | cgagtaaaagacggccagtNNNNNNNNNNNNNctccgctgc agacct | 110 |
| CDKN2A | chr9:21971015-21971121 | cacacaggaaacagctatgaccatgGACCCGCCACT CTCAC | cgagtaaaagacggccagtNNNNNNNNNNNNNNGCTCCTC AGCCAGGTCCA | 142 |
| CTNNB1 | chr3:41266060-41266143 | cacacaggaaacagctatgaccatggccatggAACCAG ACAGAAA | cgagtaaaagacggccagtNNNNNNNNNNNNNNCCTCAGG ATTGCCTTTACCA | 124 |
| EGFR | chr7:55242440-55242519 | cacacaggaaacagctatgaccatgCTGGATCCCAGA AGGTGAGA | cgagtaaaagacggccagtNNNNNNNNNNNNNNCCCACAC AGCAAAGCAGAA | 119 |
| EGFR | chr7:55259508-55259594 | cacacaggaaacagctatgaccatgtTCCCTGGTGTCA GGAAAATG | cgagtaaaagacggccagtNNNNNNNNNNNNNNGCAGCAT GTCAAGATCACAGAT | 129 |
| FBXW7 | chr4:153247315-153247386 | cacacaggaaacagctatgaccatgttgtttctgtttctc ctctg | cgagtaaaagacggccagtNNNNNNNNNNNNNNCTGCAAC ATGACCCATCAAA | 115 |
| FGFR2 | chr10:123257989-123258069 | cacacaggaaacagctatgaccatggGCAGAGTATTTG GGCGAATG | cgagtaaaagacggccagtNNNNNNNNNNNNNNNtctggtgtca gagatgGAGATG | 123 |
| KRAS | chr12:25398230-25398289 | cacacaggaaacagctatgaccatgTTTACCTCTATTG TTGGATCATATTCG | cgagtaaaagacggccagtNNNNNNNNNNNNNTGACTGA ATATAAACTTGTGGTAGTTGG | 115 |
| KRAS | chr12:25378560-25378631 | cacacaggaaacagctatgaccatgtGGGAAATAAATGT GATTTGCCTTCT | cgagtaaaagacggccagtNNNNNNNNNNNNNNTTTCAGT GTTACTTACCTGTCTTGTCTT | 124 |
| NRAS | chr1:115256505-115256588 | cacacaggaaacagctatgaccatgACACCCCCAGGA TTCTTACAG | cgagtaaaagacggccagtNNNNNNNNNNNNNNCCCTGT CCTCATGTATTGG | 125 |
| PIK3CA | chr3:178916801-178916879 | cacacaggaaacagctatgaccatgccccccctcatcaact cttc | cgagtaaaagacggccagtNNNNNNNNNNNNNNGAAAAAG CCGAAGGTCACAA | 119 |
| PIK3CA | chr3:178936043-178936115 | cacacaggaaacagctatgaccatgcCAATGAATTAAG GGAAAATGACAAA | cgagtaaaagacggccagtNNNNNNNNNNNNNCTCCATTT TAGCACTTACCTGTGAC | 123 |
| PIK3CA | chr3:178951947-178952035 | cacacaggaaacagctatgaccatgccatgtgcaattctttc ataaatc | cgagtaaaagacggccagtNNNNNNNNNNNNNNtccaagcct cttgctcagt | 132 |
| PIK3R1 | chr5:67589078-67589162 | cacacaggaaacagctatgaccatgggtttggtgctgata ttaaac | cgagtaaaagacggccagtNNNNNNNNNNNNNNccatattcC CATCTGATGAA | 130 |
| PIK3R1 | chr5:67589480-67589561 | cacacaggaaacagctatgaccatgtgtttccatgtcagct atttgtt | cgagtaaaagacggccagtNNNNNNNNNNNNNTGTAATTT TTCCCTACAGCTTCAA | 131 |
| PIK3R1 | chr5:67590332-67590419 | cacacaggaaacagctatgaccatgtgcagtaagagattgt tctatgaaagg | cgagtaaaagacggccagtNNNNNNNNNNNNNGGGTCG GCACTGTTCTTCA | 135 |
| PIK3R1 | chr5:67590980-67591053 | cacacaggaaacagctatgaccatgttcttttgcctgcagg att | cgagtaaaagacggccagtNNNNNNNNNNNNNTACTCAG CTGCCTGCTCTTC | 115 |

Fig. 8C

FIG. 8 (TABLE S1): PRIMER SEQUENCES USED IN MULTIPLEX ASSAY

| Gene | Location | Forward Primer | Reverse Primer | Size |
|---|---|---|---|---|
| PIK3R1 | chr5:67591114-67591187 | cacacaggaaacagtatgaccatgcctgaattgtagcaatcaccaa | cgacgtaaaacgacggccagtNNNNNNNNNNNNACGTATGAACAG CATTAAACCAGA | 120 |
| PIK3R1 | chr5:67592041-67592115 | cacacaggaaacagctatgaccatgtgaagatttgcccatca | cgacgtaaaacgacggccagtNNNNNNNNNNNNNNtctcccgGACAAGAAAAGTG | 115 |
| POLE | chr12:133253112-133253206 | cacacaggaaacagctatgaccatgccatcccaggagcttactt | cgacgtaaaacgacggccagtNNNNNNNNNNNNNNNggcatttgacattgagacg | 135 |
| PPP2R1A | chr19:52716302-52716401 | cacacaggaaacagctatgaccatgttccctctgagagtgtcagtgt | cgacgtaaaacgacggccagtNNNNNNNNNNNNNNNtggtgatgcccactctgc | 141 |
| PTEN | chr10:89624227-89624322 | cacacaggaaacagctatgaccatgAGCCACAGGCTCCCAGAC | cgacgtaaaacgacggccagtNNNNNNNNNNNNVGACAGAAAGGTAAACAGGAGCA | 137 |
| PTEN | chr10:89685256-89685338 | cacacaggaaacagctatgaccatgaatagttgttttagaagatatttgcaagc | cgacgtaaaacgacggccagtNNNNNNNNNNNNNNttaatggtggcttttgtttgtt | 135 |
| PTEN | chr10:89690739-89690822 | cacacaggaaacagctatgaccatgaagattcaggcaatgtttgttagtatt | cgacgtaaaacgacggccagtNNNNNNNNNNNNNNNNGCAATTAAATTTGCCGTGT | 131 |
| PTEN | chr10:89692767-89692847 | cacacaggaaacagctatgaccatgtttcttattctgagttatcttttttacca | cgacgtaaaacgacggccagtNNNNNNNNNNNNNNNCATGATTGTCATCTTCACTTAGCC | 134 |
| PTEN | chr10:89692900-89692975 | cacacaggaaacagctatgaccatgGCAATTCACTCTAAAGCTGGAAA | cgacgtaaaacgacggccagtNNNNNNNNNNNNNNTGGTCCTTACTTCCCATAGA | 121 |
| PTEN | chr10:89711865-89711928 | cacacaggaaacagctatgaccatgccaattggcttctcttttttttc | cgacgtaaaacgacggccagtNNNNNNNNNNNNNNCACTGGTCTATAATCCAGATGATTCTT | 115 |
| PTEN | chr10:89717590-89717670 | cacacaggaaacagctatgaccatgaggcatttcctgtgaataatactg | cgacgtaaaacgacggccagtNNNNNNNNNNNNNNTGAACTTGTCTTCCCGTCGT | 126 |
| PTEN | chr10:89720757-89720836 | cacacaggaaacagctatgaccatgTCTATGTGATCAAGAAATCCGATAGCA | cgacgtaaaacgacggccagtNNNNNNNNNNNNNNAAGTATCGGTTGGCTTTGTCTTT | 129 |
| PTEN | chr10:89725039-89725114 | cacacaggaaacagctatgaccatgtggttttcattttaaattttcttc | cgacgtaaaacgacggccagtNNNNNNNNNNNNNNNAGGTTCATTGTCACTAACATCTGT | 127 |
| PTEN | chr10:89725178-89725266 | cacacaggaaacagctatgaccatggtcatttcagtttattcaagttta | cgacgtaaaacgacggccagtNNNNNNNNNNNNNNNCTGACACCACTCACTCTGATCC | 138 |
| TP53 | chr17:7579839-7579915 | cacacaggaaacagctatgaccatgccttccaatggatccactcac | cgacgtaaaacgacggccagtNNNNNNNNNNNNactgcttccgggtcact | 116 |
| TP53 | chr17:7579698-7579770 | cacacaggaaacagctatgaccatgagccccctagcagagacct | cgacgtaaaacgacggccagtNNNNNNNNNNNNNcagcccaaccctttgtcctt | 111 |
| TP53 | chr17:7579408-7579482 | cacacaggaaacagctatgaccatgAGCTCCCAGAATGCCAGAG | cgacgtaaaacgacggccagtNNNNNNNNNNNNTGGGAAGGGACAGAACATGA | 114 |
| TP53 | chr17:7578493-7578571 | cacacaggaaacagctatgaccatggccctgactttcaactctgtct | cgacgtaaaacgacggccagtNNNNNNNNNNNNNNNNGGGGTGTGGAATCAACC | 119 |

Fig. 8D

FIG. 8 (TABLE S1): PRIMER SEQUENCES USED IN MULTIPLEX ASSAY

| | | | |
|---|---|---|---|
| TP53 | chr17:75783 54-7578436 | cacacaggaaacagctatgaccatgGCCATGGCCATCTACAAGC | cgacgtaaaacgacggccagtNNNNNNNNNNNNaccagccctgtcgtctctc | 121 |
| TP53 | chr17:7578157 - 7578240 | cacacaggaaacagctatgaccatgGTGGAAGCAAATTTCGTGT | cgacgtaaaacgacggccagtNNNNNNNNNNNNcttaacccctcctcccagag | 124 |
| TP53 | chr17:7577533 - 7577614 | cacacaggaaacagctatgaccatgTGTGATGATGGTGAGGATGG | cgacgtaaaacgacggccagtNNNNNNNNNNNNtcatccttggcctgtgttatc | 123 |
| TP53 | chr17:7577089 - 7577167 | cacacaggaaacagctatgaccatgctcttgcttctcttttcc | cgacgtaaaacgacggccagtNNNNNNNNNNNNGCGAGATTCTTCCTCTGT | 121 |
| TP53 | chr17:7576804 - 7576878 | cacacaggaaacagctatgaccatgaagaagaaacggcattttgag | cgacgtaaaacgacggccagtNNNNNNNNNNNNCCAGCCAAAGAAGAAACCAC | 117 |
| TP53 | chr17:7573901 - 7573987 | cacacaggaaacagctatgaccatgGTTCCGAGAGCTGAATGAGG | cgacgtaaaacgacggccagtNNNNNNNNNNNNtaggaagcagggagtagg | 127 |
| TP53 | chr17:7572912 - 7572989 | cacacaggaaacagctatgaccatggCCACCTGAAGTCCAAAAG | cgacgtaaaacgacggccagtNNNNNNNNNNNNgaggctgcagtggggaac | 117 |
| AKT1 | chr14:105246502 - 105246583 | cacacaggaaacagctatgaccatgTCCTTGTAGCCAATGAAGGTG | cgacgtaaaacgacggccagtNNNNNNNNNNNNagggtctgacgggtagagtgt | 124 |
| APC | chr5:112173652 - 112173733 | cacacaggaaacagctatgaccatgcccaaggcatctcatcgtag | cgacgtaaaacgacggccagtNNNNNNNNNNNNaggacagtcatgttgcagtatt | 125 |
| APC | chr5:112173802 - 112173885 | cacacaggaaacagctatgaccatgttaccagtcctcttcatc | cgacgtaaaacgacggccagtNNNNNNNNNNNNaagttcctggattttctgttgct | 129 |
| APC | chr5:112173974 - 112174062 | cacacaggaaacagctatgaccatggccaaagtcatgaagaagtg | cgacgtaaaacgacggccagtNNNNNNNNNNNNgtgtatgggcagcagagctt | 130 |
| APC | chr5:112174130 - 112174200 | cacacaggaaacagctatgaccatgaagtcggaaaattcaaataggaca | cgacgtaaaacgacggccagtNNNNNNNNNNNNgacctcttttaccataccatca | 119 |
| APC | chr5:112174281 - 112174335 | cacacaggaaacagctatgaccatgaagatgatgaaagtaagttttgcagtt | cgacgtaaaacgacggccagtNNNNNNNNNNNNggtgtatctagttcctcattatca | 110 |
| APC | chr5:112174410 - 112174475 | cacacaggaaacagctatgaccatgagatgagcagttgaactctggaa | cgacgtaaaacgacggccagtNNNNNNNNNNNNccttgattgtctttgctcacttt | 112 |
| APC | chr5:112174587 - 112174663 | cacacaggaaacagctatgaccatgattttggcagcaggaatgtg | cgacgtaaaacgacggccagtNNNNNNNNNNNNtcttgacacaaagactggcttac | 122 |
| APC | chr5:112174729 - 112174802 | cacacaggaaacagctatgacc atgtcaataggctgatccacatgac | cgacgtaaaacgacggccagtNNNNNNNNNNNNtgataagctaccaattatagtgaacg | 123 |
| APC | chr5:112174874 - 112174959 | cacacaggaaacagctatgaccatgttccttcatcacagaaacagtca | cgacgtaaaacgacggccagtNNNNNNNNNNNNtgattctgcctcttggcatta | 130 |

FIG. 8 (TABLE S1): PRIMER SEQUENCES USED IN MULTIPLEX ASSAY

| Gene | Location | Primer 1 | Primer 2 | Size |
|---|---|---|---|---|
| APC | chr5:112175061 - 112175137 | cacacaggaaacagctatgaccatgcttgcaaagtttcttct attaaccaag | cgacgtaaaacgacggccagtNNNNNNNNNNNNNtgattacatc ctatttcatcttcagc | 130 |
| APC | chr5:112175253 - 112175345 | cacacaggaaacagctatgaccatgggtcagctgaagatc ctgtga | cgacgtaaaacgacggccagtNNNNNNNNNNNNNNtcgctcctga agaaaattcaa | 135 |
| APC | chr5:112175404 - 112175479 | cacacaggaaacagctatgaccatgggtgtcagacaccc aaaag | cgagtaaaagacggccagtNNNNNNNNNNNNNNNNctggcaatc gaacgactctc | 116 |
| APC | chr5:112175601 - 112175682 | cacacaggaaacagctatgaccatgccaccagcag agta | cgagtaaaagacggccagtNNNNNNNNNNNNNNNgcagcttgct taggtccactc | 123 |
| APC | chr5:112175837 - 112175913 | cacacaggaaacagctatgaccatggagctgatgagc attt | cgagtaaaagacgcggccagtNNNNNNNNNNNNtggttttcatt tgattcttaggc | 120 |
| APC | chr5:112176000 - 112176080 | cacacaggaaacagctatgaccatgaggacctattagatg attcagatgatg | cgagtaaaacgacggccagtNNNNNNNNNNNNNNggtgagagt aatttgaagcag | 130 |
| BRAF | chr7:140453119 - 140453192 | cacacaggaaacagctagaccatgTGTTTCTTTAC TTACTACACCTCAGA | cgagtaaaagacgcggccagtNNNNNNNNNNNNNAACTGTT CAAACTGATGGGACC | 124 |
| CDKN2A | chr9:21974762 - 2974843 | cacacaggaaacagctatgaccatgggggagagcaggca gc | cgagtaaaagacgcggccagtNNNNNNNNNNNNNNCACCTCCT CTACCCGACCC | 117 |
| CDKN2A | chr9:21971132 - 21971216 | cacacaggaaacagctatgaccatggcgctgaccattct gttct | cgagtaaaagacgcggccagtNNNNNNNNNNNNNNGGGTCGG GTGAGAGTGG | 123 |
| CDKN2A | chr9:21970985 - 21971073 | cacacaggaaacagctatgaccatgCTTCCTGGACAC GCTGGT | cgagtaaaagacgcggccagtNNNNNNNNNNNNNGCAGGTA CCGTGCGACAT | 125 |
| EGFR | chr7:55241657 - 55241734 | cacacaggaaacagctatgaccatgTGTGCCAGGGA CCTTACCT | cgagtaaaagacgcggccagtNNNNNNNNNNNNNNGGAGAAG CTCCCAACCAAG | 116 |
| EGFR | chr7:55249057 - 55249146 | cacacaggaaacagctatgaccatggcgatcgcacacc agttg | cgagtaaaagacgcggccagtNNNNNNNNNNNNNgcatcgcct cacctcac | 129 |
| FBXW7 | chr4:153249349 - 153249437 | cacacaggaaacagctatgaccatggaagtccaacatg acaaga | cgagtaaaagacgcggccagtNNNNNNNNNNNNNNCGGACAC TCAAAGTGTGGAA | 130 |
| FBXW7 | chr4:153247231 - 153247316 | cacacaggaaacagctatgaccatgTTGAGACAGGGCC AGTGTTTACAT | cgagtaaaagacgcggccagtNNNNNNNNNNNNNNCAGTCTCT GGATCCCACAC | 129 |
| FGFR2 | chr10:123279596 - 123279682 | cacacaggaaacagctatgaccatgggcattcactgta aacc | cgagtaaaagacgcggccagtNNNNNNNNNNNNNtcttccctc tccacagA | 127 |
| FGFR2 | chr10:123247510 - 123247588 | cacacaggaaacagctatgaccatgcagcagcagaaatgtt ttggta | cgagtaaaagacgcggccagtNNNNNNNNNNNNNNactgccatg acttacattgg | 121 |
| KRAS | chr12:25380265 - 25380337 | cacacaggaaacagctatgaccatgTTCTCCCTTCTCA GGATTCCTAC | cgagtaaaagacgcggccagtNNNNNNNNNNNNNNNTGTACTG GTCCCTCATTGCAC | 117 |
| MAPK1 | chr22:22127141 - 22127224 | cacacaggaaacagctatgaccatgcattcaaccacac aagagg | cgagtaaaacgacggccagtNNNNNNNNNNNNNNNatctatgtcc ctgaagcagca | 126 |

Fig. 8E

FIG. 8 (TABLE S1): PRIMER SEQUENCES USED IN MULTIPLEX ASSAY

| | | | |
|---|---|---|---|
| NRAS | chr1:115258739 - 115258820 | cacacaggaaacagctagaccatgGATGTGGCTCGC CAATTAAC | cgagtaaagaagggccagtNNNNNNNNNNNNGATTGTC AGTGCGCTTTTCC | 122 |
| PIK3CA | chr3:178921457 - 178921533 | cacacaggaaacagctagaccatgtttcagacgcatt tccac | cgacgtaaaacgacggccagtNNNNNNNNNNNNacattcaagt aggttgcacaa | 120 |
| PIK3CA | chr3:178952014 - 178952094 | cacacaggaaacagctagaccatgTTTGATGACATT GCATACATTCG | cgacgtaaaacgacggccagtNNNNNNNNNNNNGATCCAA TCCATTTTTGTTGTCCAG | 129 |
| PIK3R1 | chr5:67588948 - 67589025 | cacacaggaaacagctagaccatgcagggaagaagtga atgaaaaa | cgacgtaaaacgacggccagtNNNNNNNNNNNNcagctatatt ccctgctacct | 124 |
| PIK3R1 | chr5:67589557 - 67589642 | cacacaggaaacagctagaccatgcta tgaccatgtctaGGATCAAGT TGTCAAAGAAGA | cgacgtaaaacgacggccagtNNNNNNNNNNNNCTGGGAT GTGCGGGTATATT | 131 |
| PIK3R1 | chr5:67590392 - 67590477 | cacacaggaaacagctagaccatgCCAAATGAAAA GGAGCAGCTATTG | cgacgtaaaacgacggccagtNNNNNNNNNNNNTTCTTTCT CATTGCCTTCACG | 130 |
| PIK3R1 | chr5:67591049 - 67591122 | cacacaggaaacagctagaccatgTTGACAGTAGAA GAAGATTGGAAGAA | cgacgtaaaacgacggccagtNNNNNNNNNNNNTGGTCTCT CGTCTTTCTCAGC | 121 |
| POLE | chr12:133250276 - 133250363 | cacacaggaaacagctagaccatgtctgtggtgtccca gttt | cgacgtaaaacgacggccagtNNNNNNNNNNNNgactGCC C ACAGGAAGGTAA | 128 |
| PPP2R1A | chr19:52715960 - 52716038 | cacacaggaaacagctagaccatgACATGGGATG ATCTCACTCTT | cgacgtaaaacgacggccagtNNNNNNNNNNNNTACTTCCG GAACCTGTGCTC | 121 |
| PTEN | chr10:89653765 - 89653832 | cacacaggaaacagctagaccatggctgcatatttcagat atttctttcc | cgacgtaaaacgacggccagtNNNNNNNNNNNNCATCATC AATATTGTTCCTGTATACGC | 121 |
| PTEN | chr10:89690812 - 89690878 | cacacaggaaacagctagaccatgaccatgcagtaagatacagtc tatcgggtttaagt | cgacgtaaaacgacggccagtNNNNNNNNNNNNttttaaacttt tctttagTTGTGCTGA | 124 |
| PTEN | chr10:89692976 - 89693060 | cacacaggaaacagctagaccatgaccatgaaaccaaaatctgtt ttccaa | cgacgtaaaacgacggccagtNNNNNNNNNNNNAGGCACA AGAGCCCTAGAT | 127 |
| PTEN | chr10:89711926 - 89711986 | cacacaggaaacagctagaccatgGCGCTATGTGTA TTATTAGCTACCTG | cgacgtaaaacgacggccagtNNNNNNNNNNNNCGCCACT GAACATTGGAATAG | 110 |
| PTEN | chr10:89717640 - 89717734 | cacacaggaaacagctagaccatgTGTGGTCTCGCCA GCTAAAGG | cgacgtaaaacgacggccagtNNNNNNNNNNNNGTTCTGTT TGTGGAAGAACTCTACTTT | 142 |
| PTEN | chr10:89720693 - 89720757 | cacacaggaaacagctagaccatgTTTGGGTAAATA CATTCTTCATACCA | cgacgtaaaacgacggccagtNNNNNNNNNNNNTCTGCAC GCTCTATACTGCAA | 112 |
| PTEN | chr10:89720833 - 89720895 | cacacaggaaacagctagaccatgTTTAACAAAAAA TGATCTTGACAAAGC | cgacgtaaaacgacggccagtNNNNNNNNNNNNacaagtcaa caaccccaca | 110 |
| PTEN | chr10:89725089 - 89725180 | cacacaggaaacagctagacc atgTAGAGGAGCCG TCAAATCCA | cgacgtaaaacgacggccagtNNNNNNNNNNNNCTGATCTT CATCAAAAGGTTCATTC | 137 |

Fig. 8F

FIG. 8 (TABLE S1): PRIMER SEQUENCES USED IN MULTIPLEX ASSAY

| | | | | |
|---|---|---|---|---|
| TP53 | chr17:7579459-7579551 | cacacaggaaacagctatgaccatgaccatgGCAATGATGAT TTGATGCTG | cgacgtaaaacgacggccagtNNNNNNNNNNNNNNCGGTGTA GGAGCTGCTGG | 132 |
| TP53 | chr17:7579291-7579376 | cacacaggaaacagctatgaccatgaccatgaagtctcatggaagc | cgacgtaaaacgacggccagtNNNNNNNNNNNNNNCCCTTCCC AGAAACCTACC | 127 |
| TP53 | chr17:7578437-7578518 | cacacaggaaacagctatgaccatgaccatgCTCCGTCATGTG CTGTGACT | cgacgtaaaacgacggccagtNNNNNNNNNNNNNNCAACAAG ATGTTTTGCCAACTG | 124 |
| TP53 | chr17:7_578233-7578308 | cacacaggaaacagctatgaccatgtcccaggcctctgatt | cgacgtaaaacgacggccagtNNNNNNNNNNNNNNCGAAAAG TGTTCGTCGTCATCCA | 116 |
| TP53 | chr17:7577498-7577584 | cacacaggaaacagctatgaccatgTGGCCTCTGACTG TACCACCATC | cgacgtaaaacgacggccagtNNNNNNNNNNNNNNgtggcaagt gctcctga | 127 |
| TP53 | chr17:7577017-7577102 | cacacaggaaacagctatgaccatgCGTGTTTGCGCC TGTCCTG | cgacgtaaaacgacggccagtNNNNNNNNNNNNNNgcttcttgtc ctgcttgctt | 125 |
| TP53 | chr17:7576865-7576933 | cacacaggaaacagctatgaccatgttttatccactttcctt gcctct | cgacgtaaaacgacggccagtNNNNNNNNNNNNNNcaagactta gtacCTGAAGGGTGAA | 117 |
| TP53 | chr17:7573964-7574039 | cacacaggaaacagctatgaccatgCCCTGGCTCCTT CCCAG | cgacgtaaaacgacggccagtNNNNNNNNNNNNNNcttctccccc tcctctgttg | 113 |
| TP53 | chr17:7572950-7573022 | cacacaggaaacagctatgaccatgatgtcatctctcctccc tgct | cgacgtaaaacgacggccagtNNNNNNNNNNNNNNAGTCTGA GTCAGGCCCTTCTG | 115 |
| APC | chr5:112173706-112173776 | cacacaggaaacagctatgaccatgtgattatgttttgaca ccaatcg | cgacgtaaaacgacggccagtNNNNNNNNNNNNNNgaagaggag ctgggtaacactg | 117 |
| APC | chr5:112173872-112173945 | cacacaggaaacagctatgaccatggagaacgcggaattg gtcta | cgacgtaaaacgacggccagtNNNNNNNNNNNNNNccatgactttt ggcaatctgg | 114 |
| APC | chr5:112174156-112174226 | cacacaggaaacagctatgaccatgttctatgcttatgcc aaattaga | cgacgtaaaacgacggccagtNNNNNNNNNNNNNNggattcaatc gagggttttca | 116 |
| APC | chr5:112174314-112174403 | cacacaggaaacagctatgaccatgagcgacctagccca taaaa | cgacgtaaaacgacggccagtNNNNNNNNNNNNNNtgaaggactt tgccttccag | 130 |
| APC | chr5:112174469-112174546 | cacacaggaaacagctatgaccatgatgtggttggaacttg aggtg | cgacgtaaaacgacggccagtNNNNNNNNNNNNNNgacccaaac acatatagaagatgaa | 125 |
| APC | chr5:112174633-112174712 | cacacaggaaacagctatgaccatgccaatggttcagaaa caaatcg | cgacgtaaaacgacggccagtNNNNNNNNNNNNNNtcttcagagt aacgttcactataattgg | 130 |
| APC | chr5:112174782-112174852 | cacacaggaaacagctatgaccatgaagaagagagacca acaaattatgca | cgacgtaaaacgacggccagtNNNNNNNNNNNNNNaaaatgact gtttctgtgatgaagg | 123 |
| APC | chr5:112174936-112175009 | cacacaggaaacagctatgaccatgccgaacatatgtcttc aagcag | cgacgtaaaacgacggccagtNNNNNNNNNNNNNNagcctttga ggctgaccac | 116 |
| APC | chr5:112175138-112175213 | cacacaggaaacagctatgaccatgatgtagttcattatc atctttgtcatca | cgacgtaaaacgacggccagtNNNNNNNNNNNNNNgctgaccta gttccaatctttcctt | 130 |

Fig. 8G

FIG. 8 (TABLE S1): PRIMER SEQUENCES USED IN MULTIPLEX ASSAY

| | | | |
|---|---|---|---|
| APC | chr5:112175443 - 112175520 | cacacaggaaacagctatgaccatgccaggagaccccactc atgtt | cgacgtaaaacgacggccagtNNNNNNNNNNatgccactta ccattccactg | 119 |
| APC | chr5:112175640 - 112175726 | cacacaggaaacagctatgaccatgCTCAAACAGCTC AAACCAAGC | cgacgtaaaacgacggccagtNNNNNNNNNNNNNAGCATCT GGAAGAACCTGGA | 128 |
| APC | chr5:112175782 - 112175870 | cacacaggaaacagctatgaccatgtttgccacggaaagt actcc | cgacgtaaaacgacggccagtNNNNNNNNNNNNNNccattgtca ttttcctgaactg | 132 |
| APC | chr5:112175954 - 112176022 | cacacaggaaacagctatgaccatgaaaaccaagagaaa gaggcagaa | cgacgtaaaacgacggccagtNNNNNNNNNNNNNNttggcatggc agaaataataca | 114 |
| CDKN2A | chr9:21974704 - 21974781 | cacacaggaaacagctatgaccatgAGCCTTCGGCTG ACTGG | cgacgtaaaacgacggccagtNNNNNNNNNNNNNGGCCTCC GACCGTAACTATT | 115 |
| CDKN2A | chr9:21971092 - 21971171 | cacacaggaaacagctatgaccatgCCGAGTGGCGG AGCTG | cgacgtaaaacgacggccagtNNNNNNNNNNNNNNCACCAGC GTGTCCAGGAAG | 115 |
| CDKN2A | chr9:21970899 - 21970986 | cacacaggaaacagctatgaccatgAGGACTGGGC CATCG | cgacgtaaaacgacggccagtNNNNNNNNNNNNNacaaattctc agatcatcagtcctc | 129 |
| PIK3R1 | chr5:67589582 - 67589651 | cacacaggaaacagctatgaccatgAGATAATATTGA AGCTGTAGGGAAAAA | cgacgtaaaacgacggccagtNNNNNNNNNNNAAAACTC ACCTGGATGTGC | 118 |
| PIK3R1 | chr5:67590439 - 67590511 | cacacaggaaacagctatgaccatgTTTGAAGAACAG TGCCAGACC | cgacgtaaaacgacggccagtNNNNNNNNNNNNNNagcacaaga acaagggaaaca | 115 |
| PTEN | chr10:89653818 - 89653897 | cacacaggaaacagctatgaccatggaaaacacaacatga atataaacattcaa | cgacgtaaaacgacggccagtNNNNNNNNNNNNCATTATTG CTATGGGATTTCCTG | 131 |
| PTEN | chr10:89711943 - 89712020 | cacacaggaaacagctatgaccatgGCTACCTGTTAA AGAATCATCTGA | cgacgtaaaacgacggccagtNNNNNNNNNNNNNNgggaaggatg agaatttcaagcac | 126 |
| TP53 | chr17:7579522 - 7579595 | cacacaggaaacagctatgaccatgtgactgctcttttcacc catc | cgacgtaaaacgacggccagtNNNNNNNNNNNNNNTCATCTG GACCTGGGTCTTC | 115 |
| TP53 | chr17:7579358 - 7579444 | cacacaggaaacagctatgaccatgCTGCACCAGCAG CTCCTAC | cgacgtaaaacgacggccagtNNNNNNNNNNNNNNCAGAATG CAAGAACCCCAGA | 126 |

*COORDINATES REFER TO THE HUMAN REFERENCE GENOME hg19 RELEASE (GENOME REFERENCE CONSORTIUM GRCh37, FEB 2009).

** N = BASES WITH AN EQUAL PROBABILITY OF A, C, T, AND G

Fig. 8H

| CYST CLASSIFICATION | PATIENT ID | BRAF | KRAS | NRAS | PIK3CA | PIK3R1 | PPP2R1A | PTEN | TP53 |
|---|---|---|---|---|---|---|---|---|---|
| NON-NEOPLASTIC | *OVCYST 001 | | | | | | | | |
| | *OVCYST 003 | | | | | | | | |
| | OVCYST 004 | | | | | | | | |
| | OVCYST 005 | | | | | | | | |
| | OVCYST 006 | | | | | | | | |
| | OVCYST 007 | | | | | | | | |
| | OVCYST 012 | | | | | | | | |
| | OVCYST 014 | | | | | | | | |
| | *OVCYST 016 | | | | | | | | |
| | *OVCYST 021 | | | | | | | | |
| BENIGN | OVCYST 009 | | | | | | | | |
| | OVCYST 011 | | | | | | | | |
| | OVCYST 008 | | | | | | | | |
| | OVCYST 013 | | | | | | | | |
| | OVCYST 015 | | | | | | | | |
| | OVCYST 017 | | | | | | | | |
| | OVCYST 018 | | | | | | | | |
| | OVCYST 019 | | | | | | | | |
| | OVCYST 020 | | | | | | | | |
| | OVCYST 044 | | | | | | | | |
| | OVCYST 056 | | | | | | | | |
| BORDERLINE | OVCYST 042 | ▨ | | | | | | | |
| | OVCYST 043 | | ▨ | | | | | | |
| | OVCYST 045 | ▨ | | | | | | | |
| | OVCYST 047 | ▨ | | | | | | | |
| | *OVCYST 048 | | | | | | | | |
| | OVCYST 049 | ▨ | | | | | | | |
| | OVCYST 050 | ▨ | | | | | | | |
| | OVCYST 051 | | | | | | | | |
| | OVCYST 053 | ▨ | | | | | | | |
| | OVCYST 054 | | ▨ | | | | | | |
| | OVCYST 055 | | ▨ | | | | | | |
| | OVCYST 057 | | | | | | | | |
| | OVCYST 058 | | | | | | | | |
| | OVCYST 059 | ▨ | | | | | | | |
| | OVCYST 060 | ▨ | | | | | | | |
| | OVCYST 061 | | ▨ | | | | | | |
| | OVCYST 062 | ▨ | | | | | | | |
| | OVCYST 063 | | ▨ | | | | | | |
| | OVCYST 064 | ▨ | | | | | | | |
| | OVCYST 065 | ▨ | | | | | | | |
| | OVCYST 066 | | | | | | | | |
| | OVCYST 069 | | | | | | | | |
| | OVCYST 067 | ▨ | | | | | | | |
| | OVCYST 072 | | ▨ | | | | | | |

Fig. 9A

|  |  |  |  |  |  |  |  |  |  |  |
|---|---|---|---|---|---|---|---|---|---|---|
| MALIGNANT (TYPE I) | OVCYST 031 |  | ░ |  |  |  |  |  |  |  |
|  | OVCYST 035 | ░ |  |  |  |  |  |  |  |  |
|  | OVCYST 036 |  | ▨ |  |  |  |  |  |  |  |
|  | OVCYST 046 |  |  |  |  |  |  |  |  |  |
|  | **OVCYST 070 |  |  |  | ▨ |  |  |  |  | ▨ |
|  | OVCYST 071 |  |  |  |  |  |  |  |  | ▨ |
|  | OVCYST 074 |  |  |  |  |  |  |  |  |  |
|  | OVCYST 075 |  | ░ |  |  |  |  |  |  |  |
|  | OVCYST 076 |  |  |  |  |  |  |  |  |  |
|  | OVCYST 077 |  | ▨ |  |  |  |  |  |  |  |
|  | **OVCYST 078 |  |  | ░ |  |  |  |  |  | ░ |
|  | **OVCYST 079 |  |  |  |  |  |  | ▨ | ▨ |  |
| MALIGNANT (TYPE II) | OVCYST 080 |  | ▨ |  |  |  |  |  |  |  |
|  | OVCYST 022 |  |  |  |  |  |  |  |  | ▨ |
|  | OVCYST 023 |  |  |  |  |  |  |  |  | ▨ |
|  | OVCYST 024 |  |  |  |  |  |  |  |  | ▨ |
|  | OVCYST 025 |  |  |  |  |  |  |  |  | ▨ |
|  | OVCYST 026 |  |  |  |  |  |  |  |  | ▨ |
|  | OVCYST 027 |  |  |  |  |  |  |  |  | ▨ |
|  | OVCYST 028 |  |  |  |  |  |  |  |  | ▨ |
|  | OVCYST 029 |  |  |  |  |  |  |  |  | ▨ |
|  | OVCYST 032 |  |  |  |  |  |  |  |  | ▨ |
|  | OVCYST 033 |  |  |  |  |  |  |  |  | ▨ |
|  | OVCYST 034 |  |  |  |  |  |  |  |  | ▨ |
|  | OVCYST 037 |  |  |  |  |  |  |  |  | ▨ |
|  | OVCYST 038 |  |  |  |  |  |  |  |  | ▨ |
|  | OVCYST 039 |  |  |  |  |  |  |  |  | ▨ |
|  | OVCYST 040 |  |  |  |  |  |  |  |  | ▨ |
|  | OVCYST 041 |  |  |  |  |  |  |  |  |  |
|  | OVCYST 073 |  |  |  | ▨ |  |  |  |  |  |
|  | **OVCYST 081 |  |  |  |  | ░ |  |  |  | ░ |

Fig. 9B

SEQUENCE LISTING

```
<160> NUMBER OF SEQ ID NOS: 266

<210> SEQ ID NO 1
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 1
cacacaggaa acagctatga ccatgcaaca tgactgtcct ttcacca            47

<210> SEQ ID NO 2
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 2
cacacaggaa acagctatga ccatgggcaa ctaccatcca gcaac              45

<210> SEQ ID NO 3
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 3
cacacaggaa acagctatga ccatggtatt ctaatttggc ataaggcata ga      52

<210> SEQ ID NO 4
<211> LENGTH: 49
<212> TYPE: DNA
<213> ORGANISM: Artificial Sequence
<220> FEATURE:
<223> OTHER INFORMATION: Forward and reverse primers

<400> SEQUENCE: 4
cacacaggaa acagctatga ccatgtgatg gttatggtaa aagaggtca          49

<210> SEQ ID NO 5
<211> LENGTH: 53
<212> TYPE: DNA
<213> ORGANISM: Artificial Sequence
```

```
<220> FEATURE:
<223> OTHER INFORMATION: Forward and reverse primers

<400> SEQUENCE: 5
cacacaggaa acagctatga ccatgggatg ataatgatgg agaactagat aca        53

<210> SEQ ID NO 6
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 6
cacacaggaa acagctatga ccatgtcgat ttgtttctga accattg                47

<210> SEQ ID NO 7
<211> LENGTH: 50
<212> TYPE: DNA
<213> ORGANISM: Artificial Sequence
<220> FEATURE:
<223> OTHER INFORMATION: Forward and reverse primers

<400> SEQUENCE: 7
cacacaggaa acagctatga ccatgtttgt tggtctctct tcttcttcat             50

<210> SEQ ID NO 8
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 8
cacacaggaa acagctatga ccatgcggtt ttactgcttt gtccag                 46

<210> SEQ ID NO 9
<211> LENGTH: 54
<212> TYPE: DNA
<213> ORGANISM: Artificial Sequence
<220> FEATURE:
<223> OTHER INFORMATION: Forward and reverse primers

<400> SEQUENCE: 9
cacacaggaa acagctatga ccatggaaaa acatattgga gtatcttcta caca        54

<210> SEQ ID NO 10
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 10
cacacaggaa acagctatga ccatggtgct gtgacactgc tggaa                  45

<210> SEQ ID NO 11
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 11
cacacaggaa acagctatga ccatgagaat cagccaggca caaag                  45
```

```
<210> SEQ ID NO 12
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 12
cacacaggaa acagctatga ccatggctcc gttcagagtg aaccat            46

<210> SEQ ID NO 13
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 13
cacacaggaa acagctatga ccatgagcac tcaggctgga tgaac             45

<210> SEQ ID NO 14
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 14
cacacaggaa acagctatga ccatggggaa tgaaacagaa tcagagc           47

<210> SEQ ID NO 15
<211> LENGTH: 49
<212> TYPE: DNA
<213> ORGANISM: Artificial Sequence
<220> FEATURE:
<223> OTHER INFORMATION: Forward and reverse primers

<400> SEQUENCE: 15
cacacaggaa acagctatga ccatgcaacc tgttttgtga tggtagaag         49

<210> SEQ ID NO 16
<211> LENGTH: 44
<212> TYPE: DNA
<213> ORGANISM: Artificial Sequence
<220> FEATURE:
<223> OTHER INFORMATION: Forward and reverse primers

<400> SEQUENCE: 16
cacacaggaa acagctatga ccatggggtc gggtagagga ggtg              44

<210> SEQ ID NO 17
<211> LENGTH: 42
<212> TYPE: DNA
<213> ORGANISM: Artificial Sequence
<220> FEATURE:
<223> OTHER INFORMATION: Forward and reverse primers

<400> SEQUENCE: 17
cacacaggaa acagctatga ccatggaccc cgccactctc ac                42

<210> SEQ ID NO 18
<211> LENGTH: 45
<212> TYPE: DNA
<213> ORGANISM: Artificial Sequence
<220> FEATURE:
<223> OTHER INFORMATION: Forward and reverse primers
```

<400> SEQUENCE: 18
cacacaggaa acagctatga ccatggccat ggaaccagac agaaa    45

<210> SEQ ID NO 19
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 19
cacacaggaa acagctatga ccatgctgga tcccagaagg tgaga    45

<210> SEQ ID NO 20
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 20
cacacaggaa acagctatga ccatgtccct ggtgtcagga aaatg    45

<210> SEQ ID NO 21
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 21
cacacaggaa acagctatga ccatgttgtt tttctgtttc tccctctg    48

<210> SEQ ID NO 22
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 22
cacacaggaa acagctatga ccatggcaga gtatttgggc gaatg    45

<210> SEQ ID NO 23
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 23
cacacaggaa acagctatga ccatgtttac ctctattgtt ggatcatatt cg    52

<210> SEQ ID NO 24
<211> LENGTH: 49
<212> TYPE: DNA
<213> ORGANISM: Artificial Sequence
<220> FEATURE:
<223> OTHER INFORMATION: Forward and reverse primers

<400> SEQUENCE: 24
cacacaggaa acagctatga ccatgggaaa taaatgtgat ttgccttct    49

<210> SEQ ID NO 25

```
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 25
cacacaggaa acagctatga ccatgacacc cccaggattc ttacag            46

<210> SEQ ID NO 26
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 26
cacacaggaa acagctatga ccatgccccc tccatcaact tcttc             45

<210> SEQ ID NO 27
<211> LENGTH: 50
<212> TYPE: DNA
<213> ORGANISM: Artificial Sequence
<220> FEATURE:
<223> OTHER INFORMATION: Forward and reverse primers

<400> SEQUENCE: 27
cacacaggaa acagctatga ccatgcaatg aattaaggga aaatgacaaa        50

<210> SEQ ID NO 28
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 28
cacacaggaa acagctatga ccatggcatg ccaatctctt cataaatc          48

<210> SEQ ID NO 29
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 29
cacacaggaa acagctatga ccatggggtt ttgggctgat attaaaac          48

<210> SEQ ID NO 30
<211> LENGTH: 49
<212> TYPE: DNA
<213> ORGANISM: Artificial Sequence
<220> FEATURE:
<223> OTHER INFORMATION: Forward and reverse primers

<400> SEQUENCE: 30
cacacaggaa acagctatga ccatgtgttt ccatgtcagc tattttgtt         49

<210> SEQ ID NO 31
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 31
```

```
cacacaggaa acagctatga ccatgtgcag taagagattg ttctatgaaa gg        52
```

<210> SEQ ID NO 32
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 32

```
cacacaggaa acagctatga ccatgtttct tttgcctgca ggatt                45
```

<210> SEQ ID NO 33
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 33

```
cacacaggaa acagctatga ccatgcctga attgtagcaa tcaccaa              47
```

<210> SEQ ID NO 34
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 34

```
cacacaggaa acagctatga ccatggatga agatttgccc catca                45
```

<210> SEQ ID NO 35
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 35

```
cacacaggaa acagctatga ccatgcccat cccaggagct tactt                45
```

<210> SEQ ID NO 36
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 36

```
cacacaggaa acagctatga ccatgttccc ttctgagagt gtcagtgt             48
```

<210> SEQ ID NO 37
<211> LENGTH: 43
<212> TYPE: DNA
<213> ORGANISM: Artificial Sequence
<220> FEATURE:
<223> OTHER INFORMATION: Forward and reverse primers

<400> SEQUENCE: 37

```
cacacaggaa acagctatga ccatgagcca caggctccca gac                  43
```

<210> SEQ ID NO 38
<211> LENGTH: 54
<212> TYPE: DNA

```
<213> ORGANISM: Artificial Sequence
<220> FEATURE:
<223> OTHER INFORMATION: Forward and reverse primers

<400> SEQUENCE: 38
cacacaggaa acagctatga ccatgaatag ttgttttaga agatatttgc aagc            54

<210> SEQ ID NO 39
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 39
cacacaggaa acagctatga ccatgaagat tcaggcaatg tttgttagta tt              52

<210> SEQ ID NO 40
<211> LENGTH: 54
<212> TYPE: DNA
<213> ORGANISM: Artificial Sequence
<220> FEATURE:
<223> OTHER INFORMATION: Forward and reverse primers

<400> SEQUENCE: 40
cacacaggaa acagctatga ccatgtttct tattctgagg ttatctttt acca             54

<210> SEQ ID NO 41
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 41
cacacaggaa acagctatga ccatggcaat tcactgtaaa gctggaaa                   48

<210> SEQ ID NO 42
<211> LENGTH: 49
<212> TYPE: DNA
<213> ORGANISM: Artificial Sequence
<220> FEATURE:
<223> OTHER INFORMATION: Forward and reverse primers

<400> SEQUENCE: 42
cacacaggaa acagctatga ccatgtcaat ttggcttctc tttttttc                   49

<210> SEQ ID NO 43
<211> LENGTH: 50
<212> TYPE: DNA
<213> ORGANISM: Artificial Sequence
<220> FEATURE:
<223> OTHER INFORMATION: Forward and reverse primers

<400> SEQUENCE: 43
cacacaggaa acagctatga ccatgaggca tttcctgtga ataatactg                  50

<210> SEQ ID NO 44
<211> LENGTH: 51
<212> TYPE: DNA
<213> ORGANISM: Artificial Sequence
<220> FEATURE:
<223> OTHER INFORMATION: Forward and reverse primers

<400> SEQUENCE: 44
cacacaggaa acagctatga ccatgtctat gtgatcaaga aatcgatagc a               51
```

```
<210> SEQ ID NO 45
<211> LENGTH: 51
<212> TYPE: DNA
<213> ORGANISM: Artificial Sequence
<220> FEATURE:
<223> OTHER INFORMATION: Forward and reverse primers

<400> SEQUENCE: 45
cacacaggaa acagctatga ccatgtgggt tttcatttta aattttcttt c          51

<210> SEQ ID NO 46
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 46
cacacaggaa acagctatga ccatgggtcc attttcagtt tattcaagtt ta         52

<210> SEQ ID NO 47
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 47
cacacaggaa acagctatga ccatgccttc caatggatcc actcac               46

<210> SEQ ID NO 48
<211> LENGTH: 44
<212> TYPE: DNA
<213> ORGANISM: Artificial Sequence
<220> FEATURE:
<223> OTHER INFORMATION: Forward and reverse primers

<400> SEQUENCE: 48
cacacaggaa acagctatga ccatgagccc cctagcagag acct                 44

<210> SEQ ID NO 49
<211> LENGTH: 44
<212> TYPE: DNA
<213> ORGANISM: Artificial Sequence
<220> FEATURE:
<223> OTHER INFORMATION: Forward and reverse primers

<400> SEQUENCE: 49
cacacaggaa acagctatga ccatgagctc ccagaatgcc agag                 44

<210> SEQ ID NO 50
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 50
cacacaggaa acagctatga ccatggccct gactttcaac tctgtct              47

<210> SEQ ID NO 51
<211> LENGTH: 44
<212> TYPE: DNA
<213> ORGANISM: Artificial Sequence
<220> FEATURE:
```

<223> OTHER INFORMATION: Forward and reverse primers

<400> SEQUENCE: 51
cacacaggaa acagctatga ccatggccat ggccatctac aagc                44

<210> SEQ ID NO 52
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 52
cacacaggaa acagctatga ccatggtgga aggaaatttg cgtgt                45

<210> SEQ ID NO 53
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 53
cacacaggaa acagctatga ccatgtgtga tgatggtgag gatgg                45

<210> SEQ ID NO 54
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 54
cacacaggaa acagctatga ccatgtgcct cttgcttctc ttttcc               46

<210> SEQ ID NO 55
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 55
cacacaggaa acagctatga ccatgaagaa gaaaacggca ttttgag              47

<210> SEQ ID NO 56
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 56
cacacaggaa acagctatga ccatggttcc gagagctgaa tgagg                45

<210> SEQ ID NO 57
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 57
cacacaggaa acagctatga ccatggccac ctgaagtcca aaaag                45

```
<210> SEQ ID NO 58
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 58
cacacaggaa acagctatga ccatgtcctt gtagccaatg aaggtg            46

<210> SEQ ID NO 59
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 59
cacacaggaa acagctatga ccatgcccaa ggcatctcat cgtag             45

<210> SEQ ID NO 60
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 60
cacacaggaa acagctatga ccatgtgtta cccagctcct cttcatc           47

<210> SEQ ID NO 61
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 61
cacacaggaa acagctatga ccatggccaa agtcatggaa gaagtg            46

<210> SEQ ID NO 62
<211> LENGTH: 49
<212> TYPE: DNA
<213> ORGANISM: Artificial Sequence
<220> FEATURE:
<223> OTHER INFORMATION: Forward and reverse primers

<400> SEQUENCE: 62
cacacaggaa acagctatga ccatgaagtc ggaaaattca aataggaca         49

<210> SEQ ID NO 63
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 63
cacacaggaa acagctatga ccatgaagat gatgaaagta agttttgcag tt     52

<210> SEQ ID NO 64
<211> LENGTH: 48
<212> TYPE: DNA
<213> ORGANISM: Artificial Sequence
<220> FEATURE:
<223> OTHER INFORMATION: Forward and reverse primers
```

<400> SEQUENCE: 64
cacacaggaa acagctatga ccatgagatg agcagttgaa ctctggaa        48

<210> SEQ ID NO 65
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 65
cacacaggaa acagctatga ccatgatttt ggacagcagg aatgtg          46

<210> SEQ ID NO 66
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 66
cacacaggaa acagctatga ccatgtcaat aggctgatcc acatgac         47

<210> SEQ ID NO 67
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 67
cacacaggaa acagctatga ccatgttcct tcatcacaga aacagtca        48

<210> SEQ ID NO 68
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 68
cacacaggaa acagctatga ccatgcttgc aaagtttctt ctattaacca ag    52

<210> SEQ ID NO 69
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 69
cacacaggaa acagctatga ccatgggtca gctgaagatc ctgtga          46

<210> SEQ ID NO 70
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 70
cacacaggaa acagctatga ccatgggtgc tcagacaccc aaaag           45

<210> SEQ ID NO 71
<211> LENGTH: 45

```
<212> TYPE: DNA
<213> ORGANISM: Artificial Sequence
<220> FEATURE:
<223> OTHER INFORMATION: Forward and reverse primers

<400> SEQUENCE: 71
cacacaggaa acagctatga ccatgcatgc caccaagcag aagta            45

<210> SEQ ID NO 72
<211> LENGTH: 44
<212> TYPE: DNA
<213> ORGANISM: Artificial Sequence
<220> FEATURE:
<223> OTHER INFORMATION: Forward and reverse primers

<400> SEQUENCE: 72
cacacaggaa acagctatga ccatggagcc tcgatgagcc attt              44

<210> SEQ ID NO 73
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 73
cacacaggaa acagctatga ccatgaggac ctattagatg attcagatga tg     52

<210> SEQ ID NO 74
<211> LENGTH: 53
<212> TYPE: DNA
<213> ORGANISM: Artificial Sequence
<220> FEATURE:
<223> OTHER INFORMATION: Forward and reverse primers

<400> SEQUENCE: 74
cacacaggaa acagctatga ccatgtgttt tcctttactt actacacctc aga    53

<210> SEQ ID NO 75
<211> LENGTH: 41
<212> TYPE: DNA
<213> ORGANISM: Artificial Sequence
<220> FEATURE:
<223> OTHER INFORMATION: Forward and reverse primers

<400> SEQUENCE: 75
cacacaggaa acagctatga ccatgggggga gagcaggcag c                41

<210> SEQ ID NO 76
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 76
cacacaggaa acagctatga ccatgtggct ctgaccattc tgttct            46

<210> SEQ ID NO 77
<211> LENGTH: 43
<212> TYPE: DNA
<213> ORGANISM: Artificial Sequence
<220> FEATURE:
<223> OTHER INFORMATION: Forward and reverse primers

<400> SEQUENCE: 77
```
cacacaggaa acagctatga ccatgcttcc tggacacgct ggt        43

<210> SEQ ID NO 78
<211> LENGTH: 44
<212> TYPE: DNA
<213> ORGANISM: Artificial Sequence
<220> FEATURE:
<223> OTHER INFORMATION: Forward and reverse primers

<400> SEQUENCE: 78
cacacaggaa acagctatga ccatgtgtgc cagggacctt acct        44

<210> SEQ ID NO 79
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 79
cacacaggaa acagctatga ccatgcgatc tgcacacacc agttg        45

<210> SEQ ID NO 80
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 80
cacacaggaa acagctatga ccatggaagt cccaaccatg acaaga        46

<210> SEQ ID NO 81
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 81
cacacaggaa acagctatga ccatgttgag acaggccagt gtttacat        48

<210> SEQ ID NO 82
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 82
cacacaggaa acagctatga ccatggctgg gcatcactgt aaacc        45

<210> SEQ ID NO 83
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 83
cacacaggaa acagctatga ccatggcagc cagaaatgtt ttggta        46

<210> SEQ ID NO 84
<211> LENGTH: 48
<212> TYPE: DNA
<213> ORGANISM: Artificial Sequence -continued

```
<220> FEATURE:
<223> OTHER INFORMATION: Forward and reverse primers

<400> SEQUENCE: 84
cacacaggaa acagctatga ccatgttctc ccttctcagg attcctac                    48

<210> SEQ ID NO 85
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 85
cacacaggaa acagctatga ccatgacatt caacccacac aagagg                      46

<210> SEQ ID NO 86
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 86
cacacaggaa acagctatga ccatggatgt ggctcgccaa ttaac                       45

<210> SEQ ID NO 87
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 87
cacacaggaa acagctatga ccatgttatt ccagacgcat ttccac                      46

<210> SEQ ID NO 88
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 88
cacacaggaa acagctatga ccatgtttga tgacattgca tacattcg                    48

<210> SEQ ID NO 89
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 89
cacacaggaa acagctatga ccatgtcagg gaagaagtga atgaaaaa                    48

<210> SEQ ID NO 90
<211> LENGTH: 50
<212> TYPE: DNA
<213> ORGANISM: Artificial Sequence
<220> FEATURE:
<223> OTHER INFORMATION: Forward and reverse primers

<400> SEQUENCE: 90
cacacaggaa acagctatga ccatgtctag gatcaagttg tcaaagaaga                  50
```

<210> SEQ ID NO 91
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 91
cacacaggaa acagctatga ccatgccaaa tgaaaaggac agctattg                48

<210> SEQ ID NO 92
<211> LENGTH: 51
<212> TYPE: DNA
<213> ORGANISM: Artificial Sequence
<220> FEATURE:
<223> OTHER INFORMATION: Forward and reverse primers

<400> SEQUENCE: 92
cacacaggaa acagctatga ccatgttgac agtagaagaa gattggaaga a            51

<210> SEQ ID NO 93
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 93
cacacaggaa acagctatga ccatggtctg tgtggtgccc agttt                   45

<210> SEQ ID NO 94
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 94
cacacaggaa acagctatga ccatgacatg gggatgatct cactctt                 47

<210> SEQ ID NO 95
<211> LENGTH: 51
<212> TYPE: DNA
<213> ORGANISM: Artificial Sequence
<220> FEATURE:
<223> OTHER INFORMATION: Forward and reverse primers

<400> SEQUENCE: 95
cacacaggaa acagctatga ccatggctgc atatttcaga tatttctttc c            51

<210> SEQ ID NO 96
<211> LENGTH: 54
<212> TYPE: DNA
<213> ORGANISM: Artificial Sequence
<220> FEATURE:
<223> OTHER INFORMATION: Forward and reverse primers

<400> SEQUENCE: 96
cacacaggaa acagctatga ccatgcagta agatacagtc tatcgggttt aagt         54

<210> SEQ ID NO 97
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 97
cacacaggaa acagctatga ccatgaaacc caaaatctgt tttccaa                47

<210> SEQ ID NO 98
<211> LENGTH: 53
<212> TYPE: DNA
<213> ORGANISM: Artificial Sequence
<220> FEATURE:
<223> OTHER INFORMATION: Forward and reverse primers

<400> SEQUENCE: 98
cacacaggaa acagctatga ccatggcgct atgtgtatta ttatagctac ctg         53

<210> SEQ ID NO 99
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 99
cacacaggaa acagctatga ccatgtgtgg tctgccagct aaagg                  45

<210> SEQ ID NO 100
<211> LENGTH: 51
<212> TYPE: DNA
<213> ORGANISM: Artificial Sequence
<220> FEATURE:
<223> OTHER INFORMATION: Forward and reverse primers

<400> SEQUENCE: 100
cacacaggaa acagctatga ccatgtttgg gtaaatacat tcttcatacc a           51

<210> SEQ ID NO 101
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 101
cacacaggaa acagctatga ccatgtttaa caaaaaatga tcttgacaaa gc          52

<210> SEQ ID NO 102
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 102
cacacaggaa acagctatga ccatgtagag gagccgtcaa atcca                  45

<210> SEQ ID NO 103
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 103
cacacaggaa acagctatga ccatggcaat ggatgatttg atgctg                 46

<210> SEQ ID NO 104

```
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 104
cacacaggaa acagctatga ccatggcatt gaagtctcat ggaagc              46

<210> SEQ ID NO 105
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 105
cacacaggaa acagctatga ccatgctccg tcatgtgctg tgact               45

<210> SEQ ID NO 106
<211> LENGTH: 43
<212> TYPE: DNA
<213> ORGANISM: Artificial Sequence
<220> FEATURE:
<223> OTHER INFORMATION: Forward and reverse primers

<400> SEQUENCE: 106
cacacaggaa acagctatga ccatggtccc caggcctctg att                 43

<210> SEQ ID NO 107
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 107
cacacaggaa acagctatga ccatgtggct ctgactgtac caccatc             47

<210> SEQ ID NO 108
<211> LENGTH: 44
<212> TYPE: DNA
<213> ORGANISM: Artificial Sequence
<220> FEATURE:
<223> OTHER INFORMATION: Forward and reverse primers

<400> SEQUENCE: 108
cacacaggaa acagctatga ccatgcgtgt ttgtgcctgt cctg                44

<210> SEQ ID NO 109
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 109
cacacaggaa acagctatga ccatgtttta tcacctttcc ttgcctct            48

<210> SEQ ID NO 110
<211> LENGTH: 42
<212> TYPE: DNA
<213> ORGANISM: Artificial Sequence
<220> FEATURE:
<223> OTHER INFORMATION: Forward and reverse primers

<400> SEQUENCE: 110
```
cacacaggaa acagctatga ccatgccctg gctccttccc ag        42

<210> SEQ ID NO 111
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 111
cacacaggaa acagctatga ccatgatgtc atctctcctc cctgct        46

<210> SEQ ID NO 112
<211> LENGTH: 49
<212> TYPE: DNA
<213> ORGANISM: Artificial Sequence
<220> FEATURE:
<223> OTHER INFORMATION: Forward and reverse primers

<400> SEQUENCE: 112
cacacaggaa acagctatga ccatgtgatt atgttttga caccaatcg        49

<210> SEQ ID NO 113
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 113
cacacaggaa acagctatga ccatggagaa cgcggaattg gtcta        45

<210> SEQ ID NO 114
<211> LENGTH: 50
<212> TYPE: DNA
<213> ORGANISM: Artificial Sequence
<220> FEATURE:
<223> OTHER INFORMATION: Forward and reverse primers

<400> SEQUENCE: 114
cacacaggaa acagctatga ccatggttct atgccttatg ccaaattaga        50

<210> SEQ ID NO 115
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 115
cacacaggaa acagctatga ccatgagccg acctagccca taaaa        45

<210> SEQ ID NO 116
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 116
cacacaggaa acagctatga ccatgatgtg gttggaactt gaggtg        46

<210> SEQ ID NO 117
<211> LENGTH: 47
<212> TYPE: DNA

<213> ORGANISM: Artificial Sequence
<220> FEATURE:
<223> OTHER INFORMATION: Forward and reverse primers

<400> SEQUENCE: 117
cacacaggaa acagctatga ccatgccaat ggttcagaaa caaatcg				47

<210> SEQ ID NO 118
<211> LENGTH: 52
<212> TYPE: DNA
<213> ORGANISM: Artificial Sequence
<220> FEATURE:
<223> OTHER INFORMATION: Forward and reverse primers

<400> SEQUENCE: 118
cacacaggaa acagctatga ccatgaagaa gagagaccaa caaattatag ca				52

<210> SEQ ID NO 119
<211> LENGTH: 47
<212> TYPE: DNA
<213> ORGANISM: Artificial Sequence
<220> FEATURE:
<223> OTHER INFORMATION: Forward and reverse primers

<400> SEQUENCE: 119
cacacaggaa acagctatga ccatgccgaa catatgtctt caagcag				47

<210> SEQ ID NO 120
<211> LENGTH: 54
<212> TYPE: DNA
<213> ORGANISM: Artificial Sequence
<220> FEATURE:
<223> OTHER INFORMATION: Forward and reverse primers

<400> SEQUENCE: 120
cacacaggaa acagctatga ccatggatgt agttcattat catctttgtc atca				54

<210> SEQ ID NO 121
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 121
cacacaggaa acagctatga ccatgcagga gaccccactc atgtt				45

<210> SEQ ID NO 122
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 122
cacacaggaa acagctatga ccatgctcaa acagctcaaa ccaagc				46

<210> SEQ ID NO 123
<211> LENGTH: 45
<212> TYPE: DNA
<213> ORGANISM: Artificial Sequence
<220> FEATURE:
<223> OTHER INFORMATION: Forward and reverse primers

<400> SEQUENCE: 123
cacacaggaa acagctatga ccatgtttgc cacggaaagt actcc				45

<210> SEQ ID NO 124
<211> LENGTH: 48
<212> TYPE: DNA
<213> ORGANISM: Artificial Sequence
<220> FEATURE:
<223> OTHER INFORMATION: Forward and reverse primers

<400> SEQUENCE: 124
cacacaggaa acagctatga ccatgaaaac caagagaaag aggcagaa         48

<210> SEQ ID NO 125
<211> LENGTH: 42
<212> TYPE: DNA
<213> ORGANISM: Artificial Sequence
<220> FEATURE:
<223> OTHER INFORMATION: Forward and reverse primers

<400> SEQUENCE: 125
cacacaggaa acagctatga ccatgagcct tcggctgact gg               42

<210> SEQ ID NO 126
<211> LENGTH: 41
<212> TYPE: DNA
<213> ORGANISM: Artificial Sequence
<220> FEATURE:
<223> OTHER INFORMATION: Forward and reverse primers

<400> SEQUENCE: 126
cacacaggaa acagctatga ccatgccgag tggcggagct g                41

<210> SEQ ID NO 127
<211> LENGTH: 41
<212> TYPE: DNA
<213> ORGANISM: Artificial Sequence
<220> FEATURE:
<223> OTHER INFORMATION: Forward and reverse primers

<400> SEQUENCE: 127
cacacaggaa acagctatga ccatgaggag ctgggccatc g                41

<210> SEQ ID NO 128
<211> LENGTH: 53
<212> TYPE: DNA
<213> ORGANISM: Artificial Sequence
<220> FEATURE:
<223> OTHER INFORMATION: Forward and reverse primers

<400> SEQUENCE: 128
cacacaggaa acagctatga ccatgagata atattgaagc tgtagggaaa aaa   53

<210> SEQ ID NO 129
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 129
cacacaggaa acagctatga ccatgtttga agaacagtgc cagacc           46

<210> SEQ ID NO 130
<211> LENGTH: 53
<212> TYPE: DNA
<213> ORGANISM: Artificial Sequence
<220> FEATURE:

<223> OTHER INFORMATION: Forward and reverse primers

<400> SEQUENCE: 130
cacacaggaa acagctatga ccatggaaaa cacaacatga atataaacat caa    53

<210> SEQ ID NO 131
<211> LENGTH: 50
<212> TYPE: DNA
<213> ORGANISM: Artificial Sequence
<220> FEATURE:
<223> OTHER INFORMATION: Forward and reverse primers

<400> SEQUENCE: 131
cacacaggaa acagctatga ccatggctac ctgttaaaga atcatctgga    50

<210> SEQ ID NO 132
<211> LENGTH: 46
<212> TYPE: DNA
<213> ORGANISM: Artificial Sequence
<220> FEATURE:
<223> OTHER INFORMATION: Forward and reverse primers

<400> SEQUENCE: 132
cacacaggaa acagctatga ccatgtgact gctcttttca cccatc    46

<210> SEQ ID NO 133
<211> LENGTH: 44
<212> TYPE: DNA
<213> ORGANISM: Artificial Sequence
<220> FEATURE:
<223> OTHER INFORMATION: Forward and reverse primers

<400> SEQUENCE: 133
cacacaggaa acagctatga ccatgctgca ccagcagctc ctac    44

<210> SEQ ID NO 134
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 134
cgacgtaaaa cgacggccag tnnnnnnnnn nnnnntagac caattccgcg ttctc    55

<210> SEQ ID NO 135
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 135
cgacgtaaaa cgacggccag tnnnnnnnnn nnnnncttct gtcttcctga gaggtatgaa    60

<210> SEQ ID NO 136
<211> LENGTH: 58
<212> TYPE: DNA
<213> ORGANISM: Artificial Sequence
<220> FEATURE:
<223> OTHER INFORMATION: Forward and reverse primers

```
<221> NAME/KEY: misc_feature
<222> LOCATION: (1)...(58)
<223> OTHER INFORMATION: n = A,T,C or G

<400> SEQUENCE: 136
cgacgtaaaa cgacggccag tnnnnnnnnn nnnnntgtgt gacagatgag agaaatgc      58

<210> SEQ ID NO 137
<211> LENGTH: 61
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(61)
<223> OTHER INFORMATION: n = A,T,C or G

<400> SEQUENCE: 137
cgacgtaaaa cgacggccag tnnnnnnnnn nnnnntgcac tatgtatttt atgggctagg    60
t                                                                    61

<210> SEQ ID NO 138
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 138
cgacgtaaaa cgacggccag tnnnnnnnnn nnnnngtttg ggtcttgccc atct          54

<210> SEQ ID NO 139
<211> LENGTH: 61
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(61)
<223> OTHER INFORMATION: n = A,T,C or G

<400> SEQUENCE: 139
cgacgtaaaa cgacggccag tnnnnnnnnn nnnnncctgt ttatactgag agcactgatg    60
a                                                                    61

<210> SEQ ID NO 140
<211> LENGTH: 59
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(59)
<223> OTHER INFORMATION: n = A,T,C or G

<400> SEQUENCE: 140
cgacgtaaaa cgacggccag tnnnnnnnnn nnnnntcaaa atgtaagcca gtctttgtg     59

<210> SEQ ID NO 141
<211> LENGTH: 56
<212> TYPE: DNA
<213> ORGANISM: Artificial Sequence
<220> FEATURE:
<223> OTHER INFORMATION: Forward and reverse primers
```

<221> NAME/KEY: misc_feature
<222> LOCATION: (1)...(56)
<223> OTHER INFORMATION: n = A,T,C or G

<400> SEQUENCE: 141
cgacgtaaaa cgacggccag tnnnnnnnnn nnnnncgtca tgtggatcag cctatt    56

<210> SEQ ID NO 142
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 142
cgacgtaaaa cgacggccag tnnnnnnnnn nnnnnccatc caagttctgc acagagt    57

<210> SEQ ID NO 143
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 143
cgacgtaaaa cgacggccag tnnnnnnnnn nnnnncagac gacacaggaa gcaga    55

<210> SEQ ID NO 144
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 144
cgacgtaaaa cgacggccag tnnnnnnnnn nnnnnaacat gagtggggtc tcctg    55

<210> SEQ ID NO 145
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 145
cgacgtaaaa cgacggccag tnnnnnnnnn nnnnnaggag gtggtggagg tgttt    55

<210> SEQ ID NO 146
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

```
<400> SEQUENCE: 146
cgacgtaaaa cgacggccag tnnnnnnnnn nnnnnggacc taagcaagct gcagtaa        57

<210> SEQ ID NO 147
<211> LENGTH: 63
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(63)
<223> OTHER INFORMATION: n = A,T,C or G

<400> SEQUENCE: 147
cgacgtaaaa cgacggccag tnnnnnnnnn nnnnntcaat atcatcatca tctgaatcat     60
cta                                                                   63

<210> SEQ ID NO 148
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 148
cgacgtaaaa cgacggccag tnnnnnnnnn nnnnnccatg ccaacaaagt catca          55

<210> SEQ ID NO 149
<211> LENGTH: 52
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(52)
<223> OTHER INFORMATION: n = A,T,C or G

<400> SEQUENCE: 149
cgacgtaaaa cgacggccag tnnnnnnnnn nnnnnctccc gctgcagacc ct             52

<210> SEQ ID NO 150
<211> LENGTH: 53
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(53)
<223> OTHER INFORMATION: n = A,T,C or G

<400> SEQUENCE: 150
cgacgtaaaa cgacggccag tnnnnnnnnn nnnnngctcc tcagccaggt cca            53

<210> SEQ ID NO 151
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 151
```
cgacgtaaaa cgacggccag tnnnnnnnnn nnnnncctca ggattgcctt tacca        55

<210> SEQ ID NO 152
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 152
cgacgtaaaa cgacggccag tnnnnnnnnn nnnnncccac acagcaaagc agaa         54

<210> SEQ ID NO 153
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 153
cgacgtaaaa cgacggccag tnnnnnnnnn nnnnngcagc atgtcaagat cacagat      57

<210> SEQ ID NO 154
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 154
cgacgtaaaa cgacggccag tnnnnnnnnn nnnnnctgca acatgaccca tcaaa        55

<210> SEQ ID NO 155
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 155
cgacgtaaaa cgacggccag tnnnnnnnnn nnnntctgg tgtcagagat ggagatg       57

<210> SEQ ID NO 156
<211> LENGTH: 63
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(63)
<223> OTHER INFORMATION: n = A,T,C or G

<400> SEQUENCE: 156
cgacgtaaaa cgacggccag tnnnnnnnnn nnnnntgact gaatataaac ttgtggtagt   60
tgg                                                                 63

<210> SEQ ID NO 157
<211> LENGTH: 63
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(63)
<223> OTHER INFORMATION: n = A,T,C or G

<400> SEQUENCE: 157
cgacgtaaaa cgacggccag tnnnnnnnnn nnnnntttca gtgttactta cctgtcttgt      60
ctt                                                                   63

<210> SEQ ID NO 158
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 158
cgacgtaaaa cgacggccag tnnnnnnnnn nnnnncgcct gtcctcatgt attgg           55

<210> SEQ ID NO 159
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 159
cgacgtaaaa cgacggccag tnnnnnnnnn nnnnngaaaa agccgaaggt cacaa           55

<210> SEQ ID NO 160
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 160
cgacgtaaaa cgacggccag tnnnnnnnnn nnnnnctcca ttttagcact tacctgtgac      60

<210> SEQ ID NO 161
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 161
cgacgtaaaa cgacggccag tnnnnnnnnn nnnnntccaa agcctcttgc tcagt           55

<210> SEQ ID NO 162

```
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 162
cgacgtaaaa cgacggccag tnnnnnnnnn nnnnnccata tttcccatct cgatgaa      57

<210> SEQ ID NO 163
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 163
cgacgtaaaa cgacggccag tnnnnnnnnn nnnnntgtaa ttttttccct acagcttcaa   60

<210> SEQ ID NO 164
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 164
cgacgtaaaa cgacggccag tnnnnnnnnn nnnnngggtc tggcactgtt cttca        55

<210> SEQ ID NO 165
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 165
cgacgtaaaa cgacggccag tnnnnnnnnn nnnnntactc agctgcctgc ttcttc       56

<210> SEQ ID NO 166
<211> LENGTH: 59
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(59)
<223> OTHER INFORMATION: n = A,T,C or G

<400> SEQUENCE: 166
cgacgtaaaa cgacggccag tnnnnnnnnn nnnnnacgta tgaacagcat taaaccaga    59

<210> SEQ ID NO 167
<211> LENGTH: 55
<212> TYPE: DNA
<213> ORGANISM: Artificial Sequence
<220> FEATURE:
```

<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 167
cgacgtaaaa cgacggccag tnnnnnnnnn nnnnntctcc cggacaagaa aagtg    55

<210> SEQ ID NO 168
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 168
cgacgtaaaa cgacggccag tnnnnnnnnn nnnnntggca tttgacattg agacg    55

<210> SEQ ID NO 169
<211> LENGTH: 53
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(53)
<223> OTHER INFORMATION: n = A,T,C or G

<400> SEQUENCE: 169
cgacgtaaaa cgacggccag tnnnnnnnnn nnnnntggtg atgcccactc tgc    53

<210> SEQ ID NO 170
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 170
cgacgtaaaa cgacggccag tnnnnnnnnn nnnnntgaca gaaaggtaaa gaggagca    58

<210> SEQ ID NO 171
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 171
cgacgtaaaa cgacggccag tnnnnnnnnn nnnnnttaat ggtggctttt tgtttgtt    58

<210> SEQ ID NO 172
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 172
cgacgtaaaa cgacggccag tnnnnnnnnn nnnnngcaat taaatttggc ggtgt    55

<210> SEQ ID NO 173
<211> LENGTH: 59
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(59)
<223> OTHER INFORMATION: n = A,T,C or G

<400> SEQUENCE: 173
cgacgtaaaa cgacggccag tnnnnnnnnn nnnnncatga ttgtcatctt cacttagcc    59

<210> SEQ ID NO 174
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 174
cgacgtaaaa cgacggccag tnnnnnnnnn nnnnntggtc cttacttccc catagaa    57

<210> SEQ ID NO 175
<211> LENGTH: 62
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(62)
<223> OTHER INFORMATION: n = A,T,C or G

<400> SEQUENCE: 175
cgacgtaaaa cgacggccag tnnnnnnnnn nnnnncactg gtctataatc cagatgattc    60
tt    62

<210> SEQ ID NO 176
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 176
cgacgtaaaa cgacggccag tnnnnnnnnn nnnnntgaac ttgtcttccc gtcgt    55

<210> SEQ ID NO 177
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 177
cgacgtaaaa cgacggccag tnnnnnnnnn nnnnnaagta tcggttggct ttgtcttt        58

<210> SEQ ID NO 178
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 178
cgacgtaaaa cgacggccag tnnnnnnnnn nnnnaggtt cattgtcact aacatctggt        60

<210> SEQ ID NO 179
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 179
cgacgtaaaa cgacggccag tnnnnnnnnn nnnnnctgac accactgact ctgatcc        57

<210> SEQ ID NO 180
<211> LENGTH: 53
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(53)
<223> OTHER INFORMATION: n = A,T,C or G

<400> SEQUENCE: 180
cgacgtaaaa cgacggccag tnnnnnnnnn nnnnnactgc cttccgggtc act        53

<210> SEQ ID NO 181
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 181
cgacgtaaaa cgacggccag tnnnnnnnnn nnnnncagcc caaccttgt cctt        54

<210> SEQ ID NO 182
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 182
cgacgtaaaa cgacggccag tnnnnnnnnn nnnnntggga agggacagaa gatga        55

```
<210> SEQ ID NO 183
<211> LENGTH: 53
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(53)
<223> OTHER INFORMATION: n = A,T,C or G

<400> SEQUENCE: 183
cgacgtaaaa cgacggccag tnnnnnnnnn nnnnnggggg tgtggaatca acc          53

<210> SEQ ID NO 184
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 184
cgacgtaaaa cgacggccag tnnnnnnnnn nnnnnaccag ccctgtcgtc tctc         54

<210> SEQ ID NO 185
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 185
cgacgtaaaa cgacggccag tnnnnnnnnn nnnnncttaa cccctcctcc cagag        55

<210> SEQ ID NO 186
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 186
cgacgtaaaa cgacggccag tnnnnnnnnn nnnnntcatc ttgggcctgt gttatc       56

<210> SEQ ID NO 187
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 187
cgacgtaaaa cgacggccag tnnnnnnnnn nnnnngcgga gattctcttc ctctgt       56

<210> SEQ ID NO 188
<211> LENGTH: 55
<212> TYPE: DNA
<213> ORGANISM: Artificial Sequence
```

```
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 188
cgacgtaaaa cgacggccag tnnnnnnnnn nnnnnccagc caaagaagaa accac      55

<210> SEQ ID NO 189
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 189
cgacgtaaaa cgacggccag tnnnnnnnnn nnnnntagga aggcagggga gtagg      55

<210> SEQ ID NO 190
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 190
cgacgtaaaa cgacggccag tnnnnnnnnn nnnnngaggc tgtcagtggg gaac       54

<210> SEQ ID NO 191
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 191
cgacgtaaaa cgacggccag tnnnnnnnnn nnnnnagggt ctgacgggta gagtgt     56

<210> SEQ ID NO 192
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 192
cgacgtaaaa cgacggccag tnnnnnnnnn nnnnnaggac agtcatgttg ccagtatt   58

<210> SEQ ID NO 193
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
```

<223> OTHER INFORMATION: n = A,T,C or G

<400> SEQUENCE: 193
cgacgtaaaa cgacggccag tnnnnnnnnn nnnnaagtt cctggatttt ctgttgct            58

<210> SEQ ID NO 194
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 194
cgacgtaaaa cgacggccag tnnnnnnnnn nnnngtgta tgggcagcag agctt              55

<210> SEQ ID NO 195
<211> LENGTH: 59
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(59)
<223> OTHER INFORMATION: n = A,T,C or G

<400> SEQUENCE: 195
cgacgtaaaa cgacggccag tnnnnnnnnn nnnnntgacc tcttttacca taaccatca         59

<210> SEQ ID NO 196
<211> LENGTH: 63
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(63)
<223> OTHER INFORMATION: n = A,T,C or G

<400> SEQUENCE: 196
cgacgtaaaa cgacggccag tnnnnnnnnn nnnnntggtg tatctagttc tccatcatta        60
tca                                                                     63

<210> SEQ ID NO 197
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 197
cgacgtaaaa cgacggccag tnnnnnnnnn nnnnnccttg attgtctttg ctcacttt          58

<210> SEQ ID NO 198
<211> LENGTH: 59
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(59)
<223> OTHER INFORMATION: n = A,T,C or G

<400> SEQUENCE: 198
cgacgtaaaa cgacggccag tnnnnnnnnn nnnnnttctt gacacaaaga ctggcttac    59

<210> SEQ ID NO 199
<211> LENGTH: 62
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(62)
<223> OTHER INFORMATION: n = A,T,C or G

<400> SEQUENCE: 199
cgacgtaaaa cgacggccag tnnnnnnnnn nnnnntgata agcctaccaa ttatagtgaa    60
cg    62

<210> SEQ ID NO 200
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 200
cgacgtaaaa cgacggccag tnnnnnnnnn nnnnntgatt ctgcctcttg gcatta    56

<210> SEQ ID NO 201
<211> LENGTH: 61
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(61)
<223> OTHER INFORMATION: n = A,T,C or G

<400> SEQUENCE: 201
cgacgtaaaa cgacggccag tnnnnnnnnn nnnnntgatt acatcctatt tcatcttcag    60
c    61

<210> SEQ ID NO 202
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 202
cgacgtaaaa cgacggccag tnnnnnnnnn nnnnntcgct cctgaagaaa attcaa    56

<210> SEQ ID NO 203
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 203
cgacgtaaaa cgacggccag tnnnnnnnnn nnnnnctggc aatcgaacga ctctc        55

<210> SEQ ID NO 204
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 204
cgacgtaaaa cgacggccag tnnnnnnnnn nnnnngcagc ttgcttaggt ccactc       56

<210> SEQ ID NO 205
<211> LENGTH: 59
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(59)
<223> OTHER INFORMATION: n = A,T,C or G

<400> SEQUENCE: 205
cgacgtaaaa cgacggccag tnnnnnnnnn nnnnntggtt tcatttgat tctttaggc    59

<210> SEQ ID NO 206
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 206
cgacgtaaaa cgacggccag tnnnnnnnnn nnnnnggtgg aggtaatttt gaagcag     57

<210> SEQ ID NO 207
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 207
cgacgtaaaa cgacggccag tnnnnnnnnn nnnnnaactg ttcaaactga tgggacc     57

<210> SEQ ID NO 208
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 208
cgacgtaaaa cgacggccag tnnnnnnnnn nnnnncacct cctctacccg accc        54

```
<210> SEQ ID NO 209
<211> LENGTH: 52
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(52)
<223> OTHER INFORMATION: n = A,T,C or G

<400> SEQUENCE: 209
cgacgtaaaa cgacggccag tnnnnnnnnn nnnnngggtc gggtgagagt gg            52

<210> SEQ ID NO 210
<211> LENGTH: 53
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(53)
<223> OTHER INFORMATION: n = A,T,C or G

<400> SEQUENCE: 210
cgacgtaaaa cgacggccag tnnnnnnnnn nnnnngcagg taccgtgcga cat           53

<210> SEQ ID NO 211
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 211
cgacgtaaaa cgacggccag tnnnnnnnnn nnnnnggaga agctcccaac caag          54

<210> SEQ ID NO 212
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 212
cgacgtaaaa cgacggccag tnnnnnnnnn nnnnngcatc tgcctcacct ccac          54

<210> SEQ ID NO 213
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 213
cgacgtaaaa cgacggccag tnnnnnnnnn nnnncggac actcaaagtg tggaa          55

<210> SEQ ID NO 214
<211> LENGTH: 55
<212> TYPE: DNA
```

```
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 214
cgacgtaaaa cgacggccag tnnnnnnnnn nnnnncagtc tctggatccc acacc        55

<210> SEQ ID NO 215
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 215
cgacgtaaaa cgacggccag tnnnnnnnnn nnnnntcttc cctctctcca ccaga        55

<210> SEQ ID NO 216
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 216
cgacgtaaaa cgacggccag tnnnnnnnnn nnnnnactgc catcgactta cattgg       56

<210> SEQ ID NO 217
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 217
cgacgtaaaa cgacggccag tnnnnnnnnn nnnnntgtac tggtccctca ttgcac       56

<210> SEQ ID NO 218
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 218
cgacgtaaaa cgacggccag tnnnnnnnnn nnnnnatcta tgtccctgaa gcagca       56

<210> SEQ ID NO 219
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
```

<222> LOCATION: (1)...(55)
<223> OTHER INFORMATION: n = A,T,C or G

<400> SEQUENCE: 219
cgacgtaaaa cgacggccag tnnnnnnnnn nnnnngattg tcagtgcgct tttcc       55

<210> SEQ ID NO 220
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 220
cgacgtaaaa cgacggccag tnnnnnnnnn nnnnnacatt cacgtaggtt gcacaaa     57

<210> SEQ ID NO 221
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 221
cgacgtaaaa cgacggccag tnnnnnnnnn nnnnngatcc aatccatttt tgttgtccag  60

<210> SEQ ID NO 222
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 222
cgacgtaaaa cgacggccag tnnnnnnnnn nnnnncagct atattccctg gcttacct   58

<210> SEQ ID NO 223
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 223
cgacgtaaaa cgacggccag tnnnnnnnnn nnnnnctggg atgtgcgggt atatt       55

<210> SEQ ID NO 224
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 224

```
cgacgtaaaa cgacggccag tnnnnnnnnn nnnnttcttt tctcattgcc ttcacg        56
```

<210> SEQ ID NO 225
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 225

```
cgacgtaaaa cgacggccag tnnnnnnnnn nnnnntggtc tctcgtcttt ctcagc        56
```

<210> SEQ ID NO 226
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 226

```
cgacgtaaaa cgacggccag tnnnnnnnnn nnnnngactg cccacaggaa ggtaa         55
```

<210> SEQ ID NO 227
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 227

```
cgacgtaaaa cgacggccag tnnnnnnnnn nnnnntactt ccggaacctg tgctc         55
```

<210> SEQ ID NO 228
<211> LENGTH: 62
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(62)
<223> OTHER INFORMATION: n = A,T,C or G

<400> SEQUENCE: 228

```
cgacgtaaaa cgacggccag tnnnnnnnnn nnnnncatca tcaatattgt tcctgtatac    60
gc                                                                    62
```

<210> SEQ ID NO 229
<211> LENGTH: 63
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(63)
<223> OTHER INFORMATION: n = A,T,C or G

<400> SEQUENCE: 229

```
cgacgtaaaa cgacggccag tnnnnnnnnn nnnnnttttta aacttttctt ttagttgtgc    60
``` tga                                                              63

<210> SEQ ID NO 230
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 230
cgacgtaaaa cgacggccag tnnnnnnnnn nnnnnaggca caagaggccc tagat        55

<210> SEQ ID NO 231
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 231
cgacgtaaaa cgacggccag tnnnnnnnnn nnnnncgcca ctgaacattg gaatag       56

<210> SEQ ID NO 232
<211> LENGTH: 62
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(62)
<223> OTHER INFORMATION: n = A,T,C or G

<400> SEQUENCE: 232
cgacgtaaaa cgacggccag tnnnnnnnnn nnnnngttct gtttgtggaa gaactctact   60
tt                                                                 62

<210> SEQ ID NO 233
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 233
cgacgtaaaa cgacggccag tnnnnnnnnn nnnnntctgc acgctctata ctgcaa       56

<210> SEQ ID NO 234
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 234
cgacgtaaaa cgacggccag tnnnnnnnnn nnnnnacaag tcaacaaccc ccaca        55

<210> SEQ ID NO 235
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 235
cgacgtaaaa cgacggccag tnnnnnnnnn nnnnnctgat cttcatcaaa aggttcattc    60

<210> SEQ ID NO 236
<211> LENGTH: 53
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(53)
<223> OTHER INFORMATION: n = A,T,C or G

<400> SEQUENCE: 236
cgacgtaaaa cgacggccag tnnnnnnnnn nnnncggtg taggagctgc tgg    53

<210> SEQ ID NO 237
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 237
cgacgtaaaa cgacggccag tnnnnnnnnn nnnnccctt cccagaaaac ctacc    55

<210> SEQ ID NO 238
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 238
cgacgtaaaa cgacggccag tnnnnnnnnn nnnncaaca agatgttttg ccaactg    57

<210> SEQ ID NO 239
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 239
cgacgtaaaa cgacggccag tnnnnnnnnn nnnncgaaa agtgtttctg tcatcca    57

<210> SEQ ID NO 240
<211> LENGTH: 53

```
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(53)
<223> OTHER INFORMATION: n = A,T,C or G

<400> SEQUENCE: 240
cgacgtaaaa cgacggccag tnnnnnnnnn nnnnngtggc aagtggctcc tga          53

<210> SEQ ID NO 241
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 241
cgacgtaaaa cgacggccag tnnnnnnnnn nnnnngcttc ttgtcctgct tgctt        55

<210> SEQ ID NO 242
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 242
cgacgtaaaa cgacggccag tnnnnnnnnn nnnnncaaga cttagtacct gaagggtgaa   60

<210> SEQ ID NO 243
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 243
cgacgtaaaa cgacggccag tnnnnnnnnn nnnnncttct cccctcctc tgttg         55

<210> SEQ ID NO 244
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 244
cgacgtaaaa cgacggccag tnnnnnnnnn nnnnnagtct gagtcaggcc cttctg       56

<210> SEQ ID NO 245
<211> LENGTH: 57
<212> TYPE: DNA
<213> ORGANISM: Artificial Sequence
<220> FEATURE:
<223> OTHER INFORMATION: Forward and reverse primers
```

```
<221> NAME/KEY: misc_feature
<222> LOCATION: (1)...(57)
<223> OTHER INFORMATION: n = A,T,C or G

<400> SEQUENCE: 245
cgacgtaaaa cgacggccag tnnnnnnnnn nnnnngaaga ggagctgggt aacactg      57

<210> SEQ ID NO 246
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 246
cgacgtaaaa cgacggccag tnnnnnnnnn nnnnnccatg actttggcaa tctgg        55

<210> SEQ ID NO 247
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 247
cgacgtaaaa cgacggccag tnnnnnnnnn nnnnnggatt caatcgaggg tttca        55

<210> SEQ ID NO 248
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 248
cgacgtaaaa cgacggccag tnnnnnnnnn nnnnntgaag gactttgcct tccag        55

<210> SEQ ID NO 249
<211> LENGTH: 61
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(61)
<223> OTHER INFORMATION: n = A,T,C or G

<400> SEQUENCE: 249
cgacgtaaaa cgacggccag tnnnnnnnnn nnnnngaccc aaacacataa tagaagatga   60
a                                                                   61

<210> SEQ ID NO 250
<211> LENGTH: 63
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(63)
```

<223> OTHER INFORMATION: n = A,T,C or G

<400> SEQUENCE: 250
cgacgtaaaa cgacggccag tnnnnnnnnn nnnntcttc agagtaacgt tcactataat    60
tgg    63

<210> SEQ ID NO 251
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 251
cgacgtaaaa cgacggccag tnnnnnnnnn nnnnaaaat gactgtttct gtgatgaagg    60

<210> SEQ ID NO 252
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 252
cgacgtaaaa cgacggccag tnnnnnnnnn nnnnagcct tttgaggctg accac    55

<210> SEQ ID NO 253
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 253
cgacgtaaaa cgacggccag tnnnnnnnnn nnnngctga cctagttcca atcttttctt    60

<210> SEQ ID NO 254
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 254
cgacgtaaaa cgacggccag tnnnnnnnnn nnnnatgcc acttaccatt ccactg    56

<210> SEQ ID NO 255
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

```
<400> SEQUENCE: 255
cgacgtaaaa cgacggccag tnnnnnnnnn nnnnnagcat ctggaagaac ctgga        55

<210> SEQ ID NO 256
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 256
cgacgtaaaa cgacggccag tnnnnnnnnn nnnnncccat tgtcattttc ctgaactg     58

<210> SEQ ID NO 257
<211> LENGTH: 57
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(57)
<223> OTHER INFORMATION: n = A,T,C or G

<400> SEQUENCE: 257
cgacgtaaaa cgacggccag tnnnnnnnnn nnnnnttggc atggcagaaa taataca      57

<210> SEQ ID NO 258
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 258
cgacgtaaaa cgacggccag tnnnnnnnnn nnnnnggcct ccgaccgtaa ctatt        55

<210> SEQ ID NO 259
<211> LENGTH: 54
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(54)
<223> OTHER INFORMATION: n = A,T,C or G

<400> SEQUENCE: 259
cgacgtaaaa cgacggccag tnnnnnnnnn nnnnncacca gcgtgtccag gaag         54

<210> SEQ ID NO 260
<211> LENGTH: 60
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(60)
<223> OTHER INFORMATION: n = A,T,C or G

<400> SEQUENCE: 260
cgacgtaaaa cgacggccag tnnnnnnnnn nnnnnacaaa ttctcagatc atcagtcctc   60
```

```
<210> SEQ ID NO 261
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 261
cgacgtaaaa cgacggccag tnnnnnnnnn nnnnnaaaac tcacctggga tgtgc      55

<210> SEQ ID NO 262
<211> LENGTH: 56
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(56)
<223> OTHER INFORMATION: n = A,T,C or G

<400> SEQUENCE: 262
cgacgtaaaa cgacggccag tnnnnnnnnn nnnnnagcac aagaacaagg gaaaca     56

<210> SEQ ID NO 263
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 263
cgacgtaaaa cgacggccag tnnnnnnnnn nnnncatta ttgctatggg atttcctg    58

<210> SEQ ID NO 264
<211> LENGTH: 58
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(58)
<223> OTHER INFORMATION: n = A,T,C or G

<400> SEQUENCE: 264
cgacgtaaaa cgacggccag tnnnnnnnnn nnnnnggaag gatgagaatt tcaagcac    58

<210> SEQ ID NO 265
<211> LENGTH: 55
<212> TYPE: DNA
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 265
cgacgtaaaa cgacggccag tnnnnnnnnn nnnnntcatc tggacctggg tcttc       55

<210> SEQ ID NO 266
<211> LENGTH: 55
<212> TYPE: DNA
```

```
<213> ORGANISM: Artificial Sequence
<220> FEATURE:
<223> OTHER INFORMATION: Forward and reverse primers
<221> NAME/KEY: misc_feature
<222> LOCATION: (1)...(55)
<223> OTHER INFORMATION: n = A,T,C or G

<400> SEQUENCE: 266
cgacgtaaaa cgacggccag tnnnnnnnnn nnnnncagaa tgcaagaagc ccaga          55
```

ASSAYING OVARIAN CYST FLUID

This application is a National Stage application under 35 U.S.C. § 371 of International Application No. PCT/US2016/046453, having an International Filing Date of Aug. 11, 2016, which claims the benefit of U.S. Provisional Application Nos. 62/203,573, filed Aug. 11, 2015, each of which is incorporated herein by reference in its entirety.

This invention was made with government support under CA 43460, 57345, and 62924 awarded by National Institutes of Health. The government has certain rights in the invention.

TECHNICAL FIELD OF THE INVENTION

This invention is related to the area of DNA analysis. In particular, it relates to analysis of genes in clinical samples.

BACKGROUND OF THE INVENTION

Ovarian cancer is the most lethal gynecologic malignancy, with 21,980 estimated new cases and 14,270 estimated deaths in the United States in 2014. Approximately 1.3% of women will be diagnosed with ovarian cancer during their lifetime (1). These cancers commonly present as an adnexal mass with cystic components, but are not associated with specific symptoms. As a result, two-thirds of ovarian cancers are diagnosed at late stage (Stage III and IV), when the 5-year survival is less than 30% (1).

Complicating the diagnosis of ovarian cancer is the fact that ovarian cysts are common in women of all ages, with a prevalence of 35% and 17% in pre- and post-menopausal women, respectively (2). These cysts are frequently benign and found incidentally on routine imaging (2). Though malignancy is an unusual cause of the cysts, 30% of the cysts exhibit radiographic features suspicious for malignancy, such as solid areas or mass (2). In addition to the anxiety that such findings provoke, many women undergo unnecessary surgery for cysts that are not malignant and may not be responsible for the symptoms they have. For example, only 5% of 570 women in a large ovarian cancer screening randomized trial who underwent surgical evaluation actually had a malignancy (3). Compounding this issue is the fact that surgery for ovarian cysts requires general anesthesia and is associated with significant morbidity, causing serious complications in 15% of women. These complications include damage to nerves and ureters, bleeding, infection, perforation of adjacent viscera, as well as hormonal and fertility loss (in the case of bilateral oophorectomy) (4). Even minimal procedures such as ovarian cystectomy can affect fertility in premenopausal women by decreasing follicular response and oocyte number (5, 6). If a preoperative test could be performed that indicated whether the cystic lesion was benign or malignant, unnecessary surgery and its associated complications could be avoided in a large number of patients, particularly women of reproductive age who wish to preserve their fertility, as well as women whose medical comorbidities or functional status makes anesthesia and surgery hazardous.

Ovarian cysts and tumors are classified as non-neoplastic, benign, borderline, or malignant based on microscopic examination after surgical removal (FIG. 1). Non-neoplastic cysts are by far the most common class of ovarian cyst. They are frequently functional in pre-menopausal women, arising when an egg is not released properly from either the follicle or corpus *luteum* and usually resolve spontaneously within several months (7). Benign cystic tumors, such as cystadenomas and cystadenofibromas, rarely progress to malignancy (8, 9). No genetic alterations have yet been identified in either non-neoplastic cysts or in benign cystic tumors (9). Neither of these cyst types requires surgery unless they are symptomatic or have undergone torsion (8). These cysts can be easily sampled with ultrasound-guided fine-needle aspiration in an outpatient setting without the need for anesthesia (10).

At the other end of the spectrum are epithelial ovarian cancers, which are potentially lethal and unequivocally require surgery. A dualistic model has been proposed to classify these neoplasms (11). Type I tumors are composed of low-grade serous, low-grade endometrioid, clear cell, and mucinous carcinomas. They are clinically indolent, frequently diagnosed at early stage (Stage I or II), and develop from well-established precursor lesions ("borderline" or "atypical proliferative" tumors, as described below) (12). Type I cancers commonly exhibit mutations in KRAS, BRAF, CTNNB1, PIK3CA, PTEN, ARID1A, or PPP2R1A (11). In contrast, type II tumors are generally high-grade serous carcinomas. They are highly aggressive, most often diagnosed in late stage (Stage III or IV), and have suggested origins from the distal fallopian tube (13). Type II cancers almost always harbor TP53 mutations (14). Also unlike type I cancers, which are relatively chemo-resistant and more often treated only with surgical excision, type II cancers respond to conventional chemotherapy, particularly after maximal debulking to reduce tumor burden (15, 16).

"Borderline" or "atypical proliferative" tumors lie in the middle of this spectrum, between the malignant cancers and the relatively harmless (non-neoplastic or benign) lesions. They are distinguished from carcinomas by the absence of stromal invasion and are precursors of type I cancers. In light of their potential for malignancy, the standard of care for borderline tumors is surgical excision. Following surgery, the prognosis is excellent compared to ovarian cancers, with 5-year survival rates over 85% (17). A minor but significant portion of borderline tumors recur after surgery, however, and a subset of the recurrences are found to have advanced to type I cancers (18). This progression is consistent with molecular findings: serous borderline tumors typically exhibit mutations in BRAF or KRAS, like their malignant counterparts (low-grade serous carcinoma) (19, 20). The presence of a BRAF mutation in a borderline tumor is associated with better prognosis and a low probability of progression to carcinoma (21). In contrast, KRAS mutations are associated with the progression to type I cancers (22).

The examination of fluids from pancreatic, renal, and thyroid cysts is routinely used in clinical management (23-25). The fluids have historically been studied by cytology to identify malignant cysts. Ovarian cysts share many features with these other types of cysts, in that they are common, often diagnosed incidentally, and are nearly always benign. However, aspiration of ovarian cyst fluid for cytology is not standard-of-care. From a historical perspective, the difference in diagnostic management probably lies in the fact that cytology has not proven to be very informative for ovarian cysts, particularly for distinguishing benign vs. borderline tumors (26, 27).

More recently, genetic analysis of specific types of cyst fluids has been considered as an aid to cytology, given that conventional cytology often has limited sensitivity and specificity (23). Based on the emerging success of the molecular genetic evaluation of other types of cysts, we reasoned that a similar approach could be applied to ovarian cysts. Evaluation of DNA from cells and cell fragments shed into the cyst fluid would presumably allow the identification of tumor-specific mutations. Unlike other, conventional markers of neoplasia such as CA-125, cancer gene mutations are exquisitely specific indicators of a neoplastic lesion (29). Moreover, the type of mutation can in some cases indicate the type of neoplastic lesion present (30). Yamada et al. have demonstrated that mutations can be detected in the cystic fluid of ovarian tumors by querying exons 4 to 9 of TP53, achieving sensitivities of 12.5% and 10%, for borderline and malignant tumors, respectively (31). Extremely sensitive methods for mutation detection, capable of identifying one mutant template allele among thousands of normal templates in a panel of genes, have recently been developed (32-34). In this study, we here applied one of these technologies to determine whether mutations could be identified in ovarian cyst fluids, and if so, whether they provided information that could in principle be used in diagnosis and management.

Because there is currently no reliable way to determine whether an ovarian cyst is malignant prior to surgical excision, many women undergo unnecessary, invasive surgeries for non-malignant lesions. There is a need in the art for techniques to determine whether surgery is required or unnecessary.

SUMMARY OF THE INVENTION

According to one aspect of the invention a method is provided in which ovarian cyst fluid is tested for mutations in a panel of genes frequently mutated in ovarian neoplasms, wherein the panel comprises BRAF, KRAS, and TP53.

According to another aspect of the invention a method is provided in which ovarian cyst fluid is tested for mutations in a panel of genes frequently mutated in ovarian neoplasms, wherein the panel comprises BRAF, KRAS, TP53, and one or more of AKT1, APC, BRCA1, BRCA2, CDKN2A, EGFR, FBXW7, FGFR2, MAPK1, NRAS, PIK3R1, and POLE.

According to another aspect of the invention a method is provided in which ovarian cyst fluid is tested for mutations in a panel of genes frequently mutated in ovarian neoplasms, wherein the panel comprises BRAF, KRAS, TP53, and one or more of CTNNB1, PIK3CA, PTEN, ARID1A, and PPP2R1A.

According to an additional aspect of the invention a method is provided in which ovarian cyst fluid is tested for mutations in a panel of genes frequently mutated in ovarian neoplasms, wherein the panel comprises BRAF, KRAS, TP53, AKT1, APC, BRCA1, BRCA2, CDKN2A, EGFR, FBXW7, FGFR2, MAPK1, NRAS, PIK3R1, and POLE.

According to an additional aspect of the invention a method is provided in which ovarian cyst fluid is tested for mutations in a panel of genes frequently mutated in ovarian neoplasms, wherein the panel comprises BRAF, KRAS, TP53, CTNNB1, PIK3CA, PTEN, ARID1A, and PPP2R1A.

According to an additional aspect of the invention a method is provided in which ovarian cyst fluid is tested for mutations in a panel of genes frequently mutated in ovarian neoplasms, wherein the panel comprises BRAF, KRAS, TP53, AKT1, APC, BRCA1, BRCA2, CDKN2A, EGFR, FBXW7, FGFR2, MAPK1, NRAS, PIK3R1, POLE, CTNNB1, PIK3CA, PTEN, ARID1A, and PPP2R1A.

These and other embodiments which will be apparent to those of skill in the art upon reading the specification provide the art with powerful methods for assessing ovarian cysts without recourse to unnecessary surgeries.

BRIEF DESCRIPTION OF THE DRAWINGS

(FIG. 2A) Classification by tumor type. No mutations were found in the DNA of non-neoplastic or benign cysts (red). Of the cysts that required surgery (blue), the median mutant allele fraction was higher in the cyst fluids associated with type II cancer (60.3%) than type I (7.8%) or borderline tumors (2.4%). (FIG. 2B) Classification by tumor stage. The DNA from cyst fluids of late-stage cancers had a higher median mutant allele fraction (51.2%) than those of early-stage cancers (7.4%) or borderline tumors (2.4%). Horizontal bars depict median and IQR.

FIGS. 3A-3D (Table 1.) Patient demographics. The clinical characteristics of patients in this study and their tumor characteristics are indicated.

FIGS. 4A-4E. (Table 2.) Mutations identified in tumors and cyst fluids. The mutations, mutant allele fractions, and amount of DNA recovered from cyst fluids are indicated.

FIG. 5 (Table 3.) Detection of tumor-specific mutations in cyst fluid. The fraction of samples detected and the median fraction of mutant alleles are indicated, grouped by cyst type, cancer stage, and the need for surgery.

FIG. 6 (Table 4.) Multivariate analysis for markers associated with need for surgery. The presence of a mutation, cyst DNA amount, and common serum biomarkers for ovarian cancer were analyzed for association with cysts that require surgical removal (Firth's penalized likelihood logistic regression).

(FIG. 7A) The amounts of DNA in cyst fluids was generally higher in cysts requiring surgery (blue) than those that do not (red), but no significant correlation was found (p=0.69). (FIG. 7B) CA-125 levels were significantly higher in cysts that required surgery than those that do not (p=0.01). (FIG. 7C) Serum HE4 levels was not correlated with the need for surgery (p=0.92). P-values were calculated using Firth's penalized likelihood logistic regression in a multivariate model (See Example 1).

FIGS. 8A-8I1 (Table S1) Primer sequences used in multiplex assay; Forward primers (SEQ ID NO: 1-133); Reverse primers (SEQ ID NO: 134-266).

FIG. 9A-9B Mutated genes found in the cyst fluid samples. FIG. 9A shows non-neoplastic, benign, and borderline. FIG. 9B shows malignant Type I and malignant Type II. Yellow boxes represent mutations with mutant allele frequency (MAF) between 0.1% and 1%; orange boxes represent mutations with MAF between 1 and 10%; red boxes represent mutations with MAF greater than 10% (* indicates patients with insufficient DNA for analysis; ** indicates patients with two detected mutations).

DETAILED DESCRIPTION OF THE INVENTION

Figure 1:
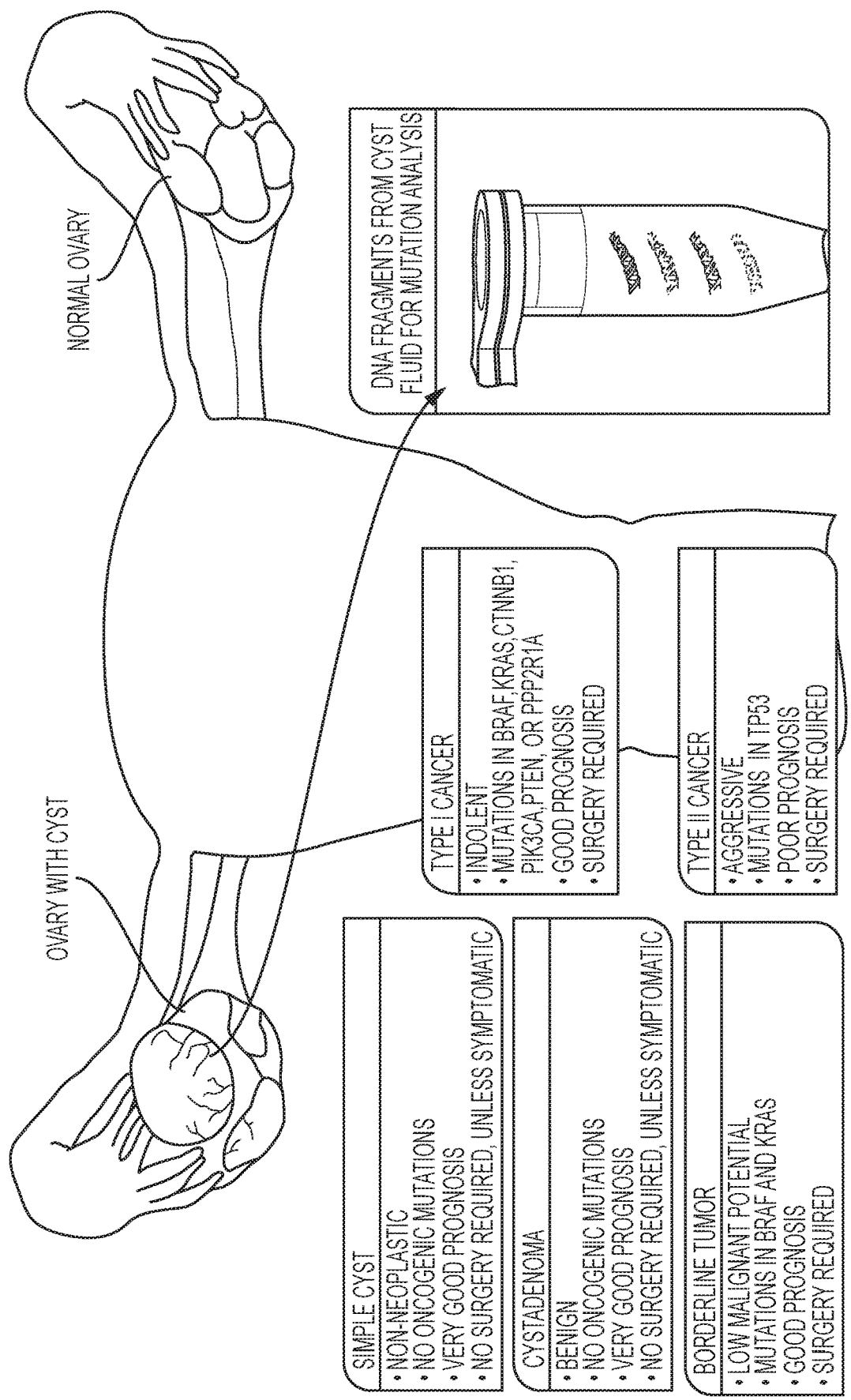
FIG. 1. Schematic showing classes of ovarian cysts and the diagnostic potential of the cyst fluid. Ovarian cysts and tumors are currently classified according to microscopic evaluation after surgical removal. The majority of ovarian cysts are non-neoplastic (often "functional" in premenopausal women). Ovarian tumors with combined cystic and solid components are either benign tumors, borderline tumors, or malignant cancers (type I or II). Only cysts associated with borderline tumors and cancers require surgical excision. We show here that the DNA purified from cyst fluid can be analyzed for somatic mutations commonly found in their associated tumors. The type of mutation detected not only indicates the type of tumor present but also could inform management.
Figure 2A:
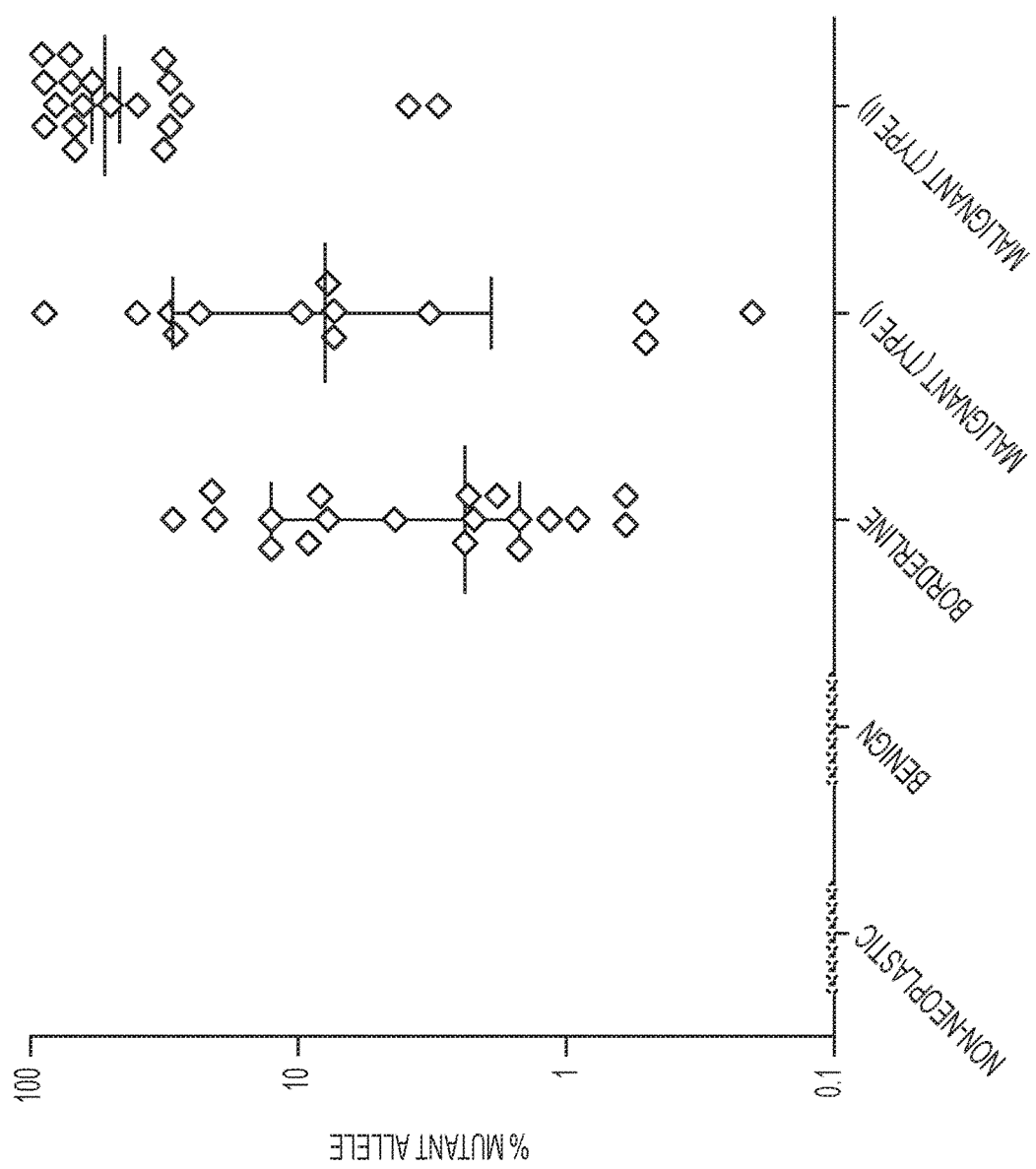
FIGS. 2A-2B. Mutant allele fractions.
Figure 2B:
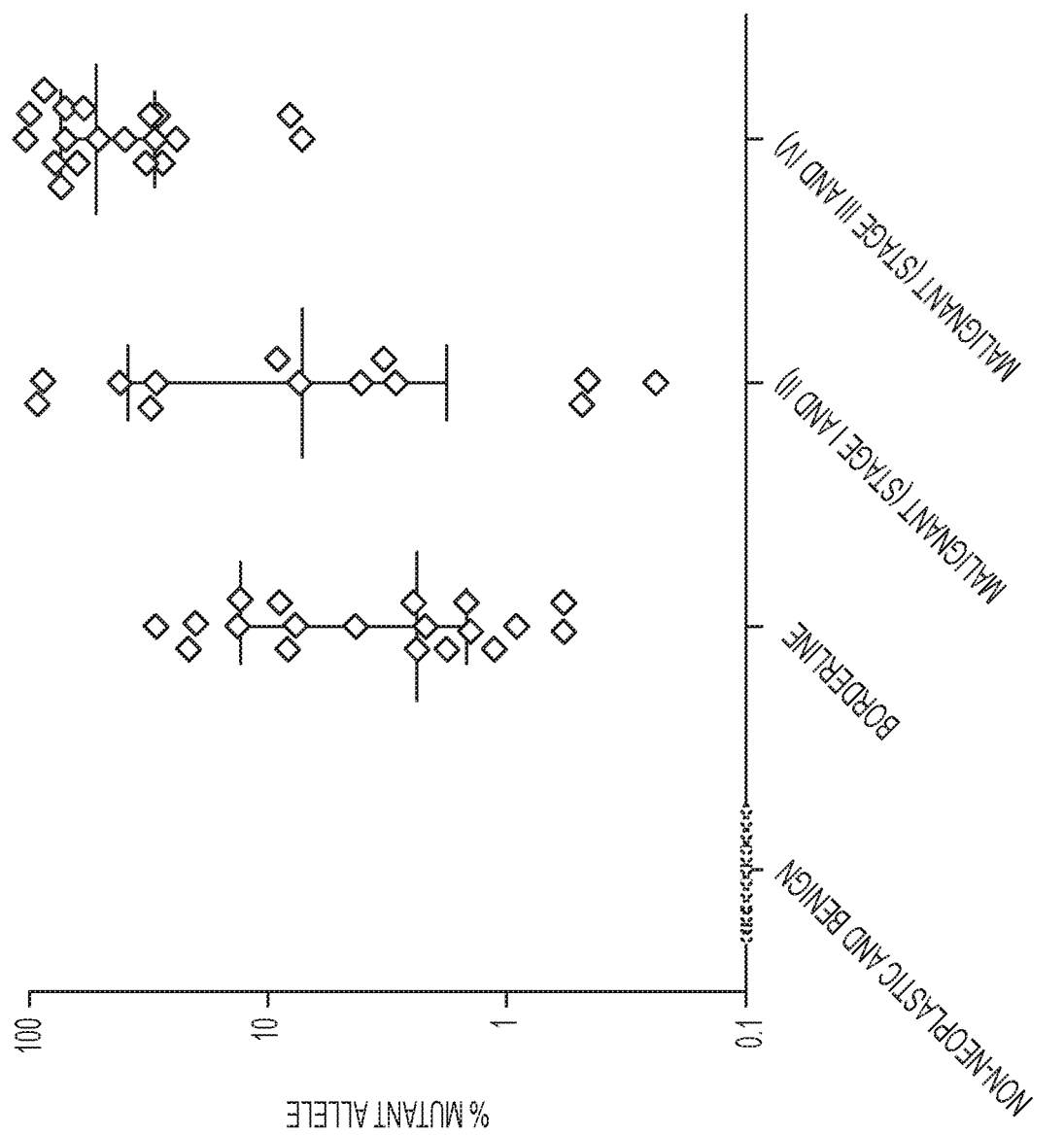
Figure 7A:
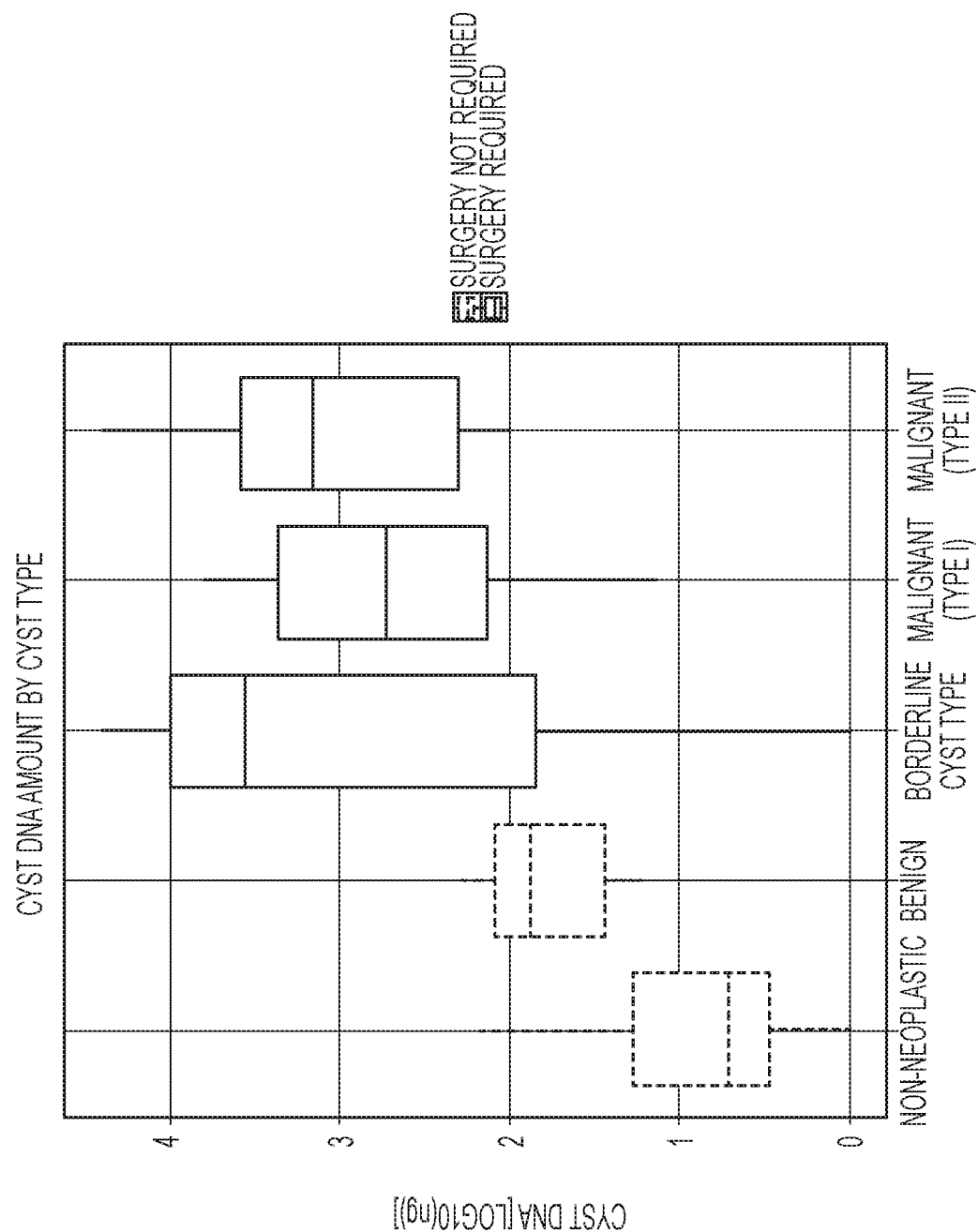
FIG. 7A-7C (FIG. S1.) Markers associated with the need for surgery. Cyst DNA amount and levels of commonly used ovarian cancer serum biomarkers are plotted according to the cyst type and need for surgery.
Figure 7B:
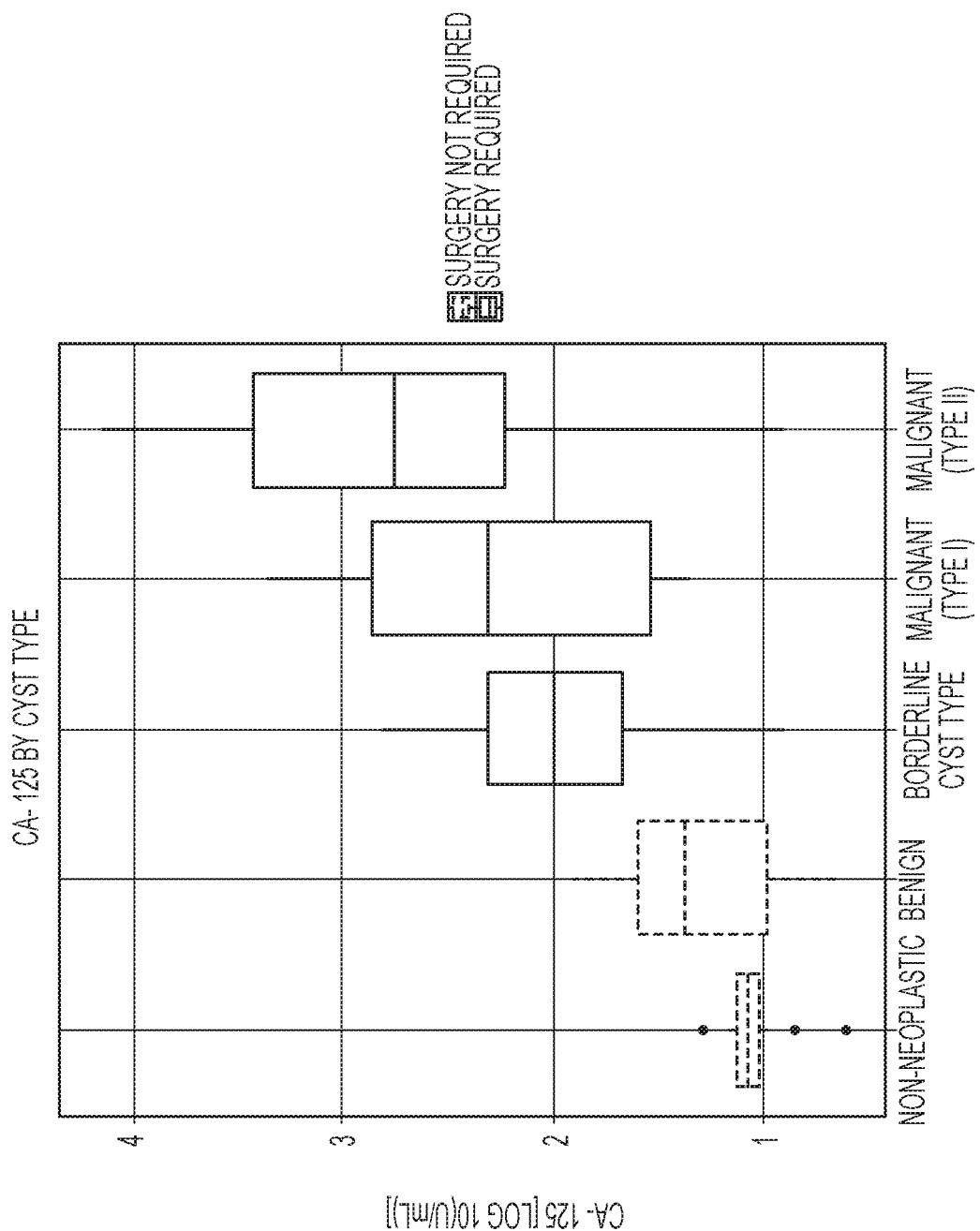
Figure 7C:
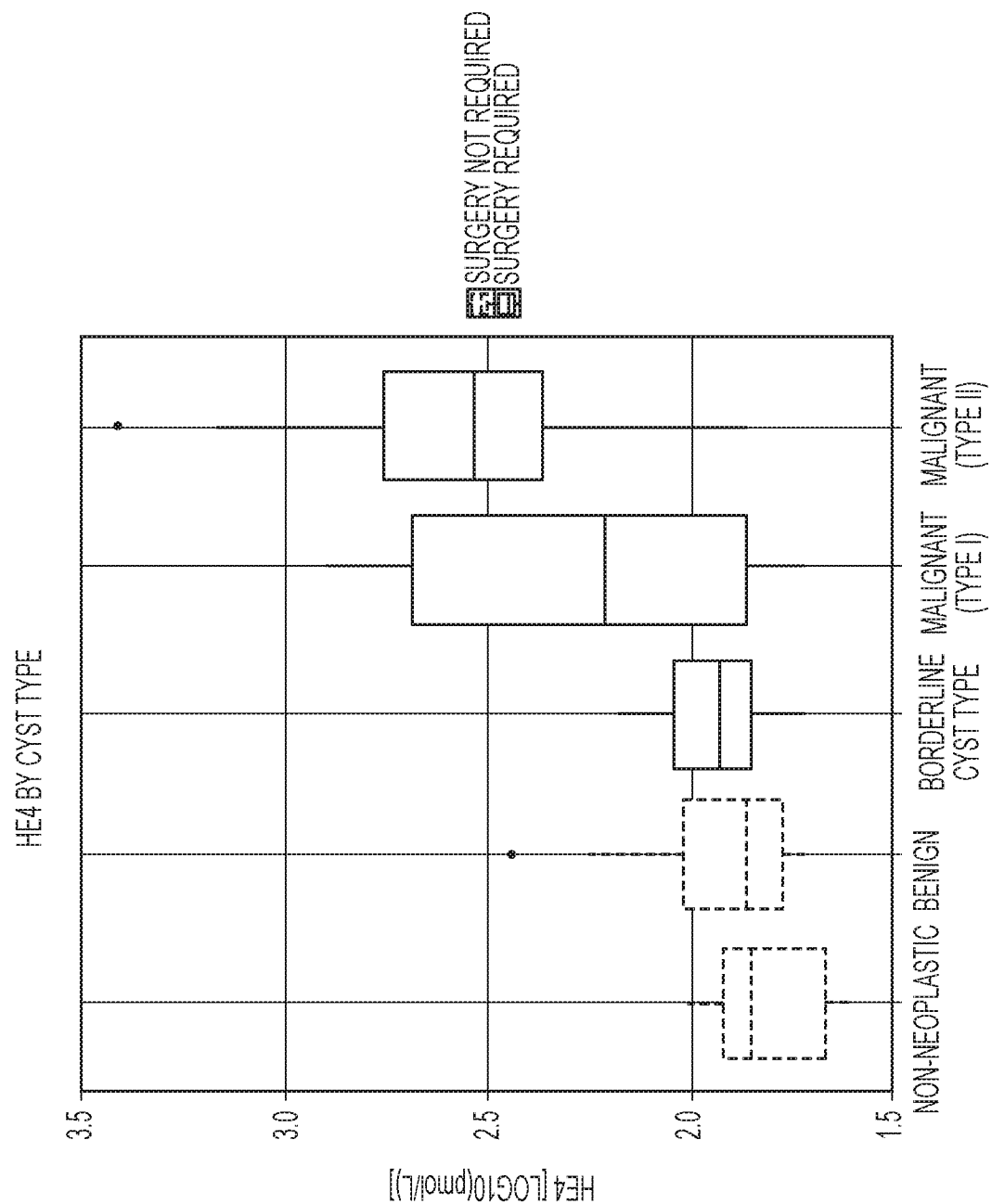

The inventors have developed an assay for testing cyst fluids. Cyst fluids are typically aspirated by a needle, preferably a fine needle. The aspiration can be performed under the guidance of a radiological technique, such as ultrasound. Other guidance techniques can be used as convenient. Cyst fluids can typically be collected from any type of ovarian cyst or cystic neoplasm, and the term "cyst" is used here to refer to all types of ovarian growths with a cystic component.

Non-neoplastic ovarian cysts typically do not require surgical removal and do not display mutations. In contrast, ovarian cysts that are associated with malignancy do require surgical removal and frequently display mutations; these mutations can further indicate the type and severity of the disease. Testing for a panel that includes markers for a broad range of ovarian cysts permits the identification of cyst type and prognosis. It also permits a clinical decision to surgically remove or not.

Other markers and clinical indication can be used in combination with the ovarian cyst fluid assay results. Plasma markers such as CA-125 and HE4 can be assessed in patient plasma. Other protein or genetic markers can be used in conjunction with the ovarian cyst fluid assay. Other clinical indicators, including radiological findings and physical findings may be used in conjunction with the ovarian cyst fluid assay.

Testing may be performed using any technique that is targeted for particular genes. These are not techniques that screen for any and all gene mutations. Rather, they are designed to detect mutations in certain predetermined genes. In some cases they are designed to detect certain mutations or mutations in certain codons. Any analytic technique can be used for detecting mutations as is convenient, efficient, and sufficiently sensitive to detect mutations in ovarian cyst fluid. The assays may be hybridization based, such as using specific probes or specific primers. The assays may employ labeled probes or primers. The assays may employ labeled secondary reagents that permit the primary reagents to be detected. Such labels include radiolabels, fluorescent labels, enzymatic labels, chromophores, and the like.

A variety of different mutation types can be detected and may be useful in providing prognosis or management decisions. Such mutations include LOH, point mutations, rearrangements, frameshifts, point mutations, and copy number variations. Specific detection techniques for these mutation types or generic detection techniques may be used. It may be desirable to use control samples from other parts of the patient's body, such as a body fluid, like plasma, saliva, urine, feces, and the like. Alternatively other control samples may include tissues such as normal tissue from a non-ovary, or cells or tissues from the ovarian cyst wall.

Cyst fluid may be obtained by any technique known in the art, including but not limited to needle aspiration. The aspiration may optionally be guided by a radiological technique such as ultrasound. Cyst fluid may be aspirated before or after initial surgical removal or subsequent surgical removal.

In some embodiments, primers will incorporate unique identification DNA sequence (UID) which are molecular barcodes. These can be randomly generated and attached to templates as a means to reduce errors arising from amplification and sequencing. Probes, primers, and UIDs can incorporate non-naturally occurring modifications to DNA sequences, by internucleotide linkage modifications, by sugar modifications, and by nucleobase modifications. For example, phosphorothioate (PS) linkages can be used in which sulfur substitutes for one nonbridging phosphate oxygen. This imparts resistance to nuclease degradation. Other modifications which can be used include N3' phosplioramidate (NP) linkages, Boranophospliate internucleotide linkages, Phosphonoacetate (PACE) linkages, Morpholino phosphoramidates, Peptide nucleic acid (PNA), 2'-O-Me nucleoside analog, 2'F-RN A modification, 2'-deoxy-2'-fluoro-β-D-arabino nucleic acid (2'F-ANA) modification and Locked nucleic acid (LNA).

Other techniques which are unbiased toward particular genes can be used as well for assessing genes of interest in cyst fluid. Such techniques include whole-genome or whole exome techniques. These may include assessments by nucleotide sequencing. The nucleotide sequencing may be redundant nucleotide sequencing. Targeted sequencing methods can be used as well.

The methods described here achieve high degrees of sensitivity and specificity. Sensitivity may be at least 15%, at least 20%, at least 25%, at least 50%, at least 60%, at least 70%, at least 80%, at least 85%, at least 90%, at least 95% for borderline and malignant tumors. Specificity may be at least 15%, at least 20%, at least 25%, at least 50%, at least 60 at least 70%, at least 80%, at least 85%, at least 90%, at least 95% for borderline and malignant tumors.

Removal of ovarian cyst fluid assay from the body can be accomplished before any surgery occurs. Thus the results of the assay can help guide the decision to perform surgery. If surgery has occurred to remove the ovarian cyst, and if it returns, a sample of ovarian cyst fluid may be obtained from the body at that time. The assays will typically be performed in a clinical laboratory on samples that have been removed by a skilled clinician, such as an interventional radiologist or a surgeon. The samples may be assayed immediately or they may suitable stored and or shipped for testing. It is possible that DNA will be extracted from the sample prior to shipping it to a laboratory for testing. Results will generally be communicated back from the assaying laboratory to the clinician for communication to a patient. Results may be recorded in paper or electronic medical records.

Ovarian cancer is the most lethal gynecologic cancer in women. However screening is not recommended by the U.S. Preventive Services Task Force using current diagnostic approaches, which too frequently lead to "important harms, including major surgical interventions in women who do not have cancer" (Moyer and Force, 2012). We have demonstrated here that driver mutations in ovarian tumors are also present in their associated cyst fluids. Moreover, the mutant allele frequencies in the cyst fluids are relatively high (median 12.6%, IQR of 2.7% to 40.2%), facilitating their detection. There were no mutations detected in the cyst fluids that were not also present in the tumors, and vice versa. Also importantly, no mutation was identified in non-neoplastic cysts or cysts associated with benign tumors. Overall, mutations were detected in a major fraction (87%) of cysts requiring surgery but not in any cyst that did not require surgery.

Our results demonstrate that mutations present in ovarian tumors are also present in their associated cyst fluids. Moreover, the mutant allele frequencies in the cyst fluids are relatively high (median 12.6%, IQR of 2.7% to 40.2%), facilitating their detection. There were no mutations detected in the cyst fluids that were not also present in the tumors, and vice versa. And most importantly, mutations were detected in a major fraction (85%) of cysts requiring surgery but not in any cyst that did not require surgery (Tables 2 and 3).

Although most (85%) of the 55 cysts requiring surgery had detectable mutations in their fluidic compartment, eight did not. All of these eight cysts occurred in borderline tumors or type I cancers, while mutations were always (100%) detectable in type II cancers (Tables 2 and 3). There are two potential explanations for our failure to detect mutations in these eight cysts. First, it is possible that the mutant DNA concentration in these cysts was below the level of technical sensitivity of our assay (~0.1% mutant allele fraction). We excluded this possibility by evaluating the tumors themselves: no mutations were detected in any of the tumors from these 8 patients. The second, and therefore more likely explanation, is that our panel of 133 amplicons, containing regions of 17 genes, was not adequate to capture the mutations that were present. Unlike type II cancers, which nearly always contain TP53 mutations (94% of the type II cancers we studied, for example), the genomic landscapes of type I cancers and borderline tumors are more heterogeneous and not as well studied (II). Further genetic evaluation of these tumors should facilitate the incorporation of additional amplicons in the panel to reach higher sensitivities. Nevertheless, the 100% sensitivity for type II cancers in our study is highly encouraging, given that these cancers account for over 90% of ovarian cancer deaths.

One limitation of our study is the number of patients evaluated. Though excision of ovarian cysts is one of the most commonly performed surgical procedures, banking of cyst fluids is not common, even in academic centers. Thus, we only had relatively small numbers (n=22) of non-neoplastic cysts and benign tumors available for study. Even so, the differences in genetic alterations among the various cyst types were striking (Tables 2 and 3). Our study will hopefully stimulate collection and analyses of ovarian cyst fluids that will be able to establish smaller confidence limits around the sensitivities and specificities reported in the current study.

A potential clinical limitation of our approach is the concern by gynecologists that needle puncture of a malignant ovarian cyst leads to seeding of the peritoneum. This concern is based on inconclusive evidence about the dangers of cyst rupture during surgery and is, at best, controversial (40). Moreover, leakage is expected to be much less likely when a tiny needle is inserted into the cyst under ultrasound-guidance than when cysts are manipulated during surgery. The idea that malignant cysts might shed cancer cells if needle-punctured also seems incongruent with the widespread practice of laparoscopic removal of ovarian cysts (41). Laparoscopic removal of a cyst carries a risk of cyst rupture, perhaps higher than needling (42). Finally, malignant pancreatic cysts are at least as dangerous as malignant ovarian cysts, yet the standard-of-care for pancreatic cysts involves repeated sampling of cyst fluid through endoscopic ultrasound over many years (43, 44). Though pancreatic cysts and ovarian cysts lie in different anatomical compartments, it is encouraging that aspiration of pancreatic cysts is not associated with an increased risk of mortality in patients with pancreatic cancer (45). Finally, recent advancements in methods to plug biopsy tracts, using materials such as absorbable gelatin slurry and torpedo, can further decrease the risk of tumor spillage associated with fine-needle aspirations (46, 47). On the basis of these observations and recent developments, we believe that ultrasound-guided aspiration of ovarian cyst fluids would likely be a safe and well-tolerated procedure.

As noted in the background of the invention section above, seven to ten patients with benign ovarian cyst lesions undergo surgery for each case of ovarian cancer found (48). In addition to the psychological impact a potential diagnosis of cancer has on patients, surgery for benign lesions entails considerable cost and morbidity. OVA-1 is the only FDA-cleared test to date that aims to distinguish benign versus malignant adnexal mass. It measures levels of five serum markers (CA-125, β-2 microglobulin, apolipoprotein A1, prealbumin, and transferrin) and is used to stratify patients who should consult a gynecologic oncologist rather than a general gynecologist for surgery. However the test has a specificity of 43% for ovarian cancer, which is even lower than that of CA-125 alone (49). While the test might encourage patients with suspected ovarian cancer to seek specialized care, it would not decrease the number of unnecessary surgeries for women with benign adnexal masses.

This study was driven by the need for a biomarker that would help distinguish malignant ovarian tumors from benign lesions and thereby reduce the number of unnecessary surgeries. Such distinction is often difficult based on symptoms and conventional diagnostic criteria. For example, in a large study of 48,053 asymptomatic post-menopausal women who underwent ultrasound examination by skilled sonographers, 8 (17%) of the 47 ovarian cancers that were identified occurred in women with persistently normal sonographic findings (Sharma et al., 2012). All eight cases were type II cancers, highlighting the potential utility of an additional assay to detect this highly lethal and aggressive type of ovarian cancer. On the other hand, of the 4367 women with abnormal sono graphic findings, less than 1% of cases proved to have malignancy upon surgery. Furthermore, of the 32 women with borderline or Type I cancers diagnosed, 22 (69%) had a serum CA-125 level within the clinically accepted normal range (≤35 units/mL). In our study, 18 of 18 (100%) type II cancers were detectable by virtue of the mutations found in cyst fluid DNA while none of the 18 benign or non-neoplastic cyst fluid contained such mutations. It is also important to note that the readout of our assay is quantitative and not dependent on the skill level of the reader (in contrast to sonography). Finally, the procedure can be performed minimally invasively in an outpatient setting. The goal of our test is not to replace clinical, radiologic, or sonographic evaluation but to augment them with molecular genetic markers.

Our study, though only proof-of-principle, illustrates one route to improve management of patients with ovarian cysts. Genetic analysis is not the only such route; proteomics could also provide clues to the correct diagnosis (50, 51). One can easily imagine how such additional information could be used to inform clinical practice in conjunction with current diagnostic methods. For example, if a cyst contained low amounts of DNA, no detectable mutations, and if the patient had low CA-125 levels, our data suggest that it is very unlikely to be a borderline tumor or malignant lesion. Either no surgery, or laparoscopic rather than open surgery, could be recommended for that patient, even if there was some solid component upon imaging. The option to avoid surgery would be particularly valuable for pre-menopausal women who generally have a low risk of ovarian cancer and might wish to preserve their fertility, as well as patients who are poor surgical candidates. However, our assay in its current format cannot completely rule out malignancy because a fraction of early-stage cancer patients did not have detectable mutations in their cysts. Therefore, patients whose clinical and functional status allows them to undergo surgery and anesthesia might still choose to have a surgical procedure. On the other hand, a minimally invasive test that provides additional, orthogonal information to patients and surgeons could inform their decision about the advisability of surgery.

Our data suggest that a cyst without any solid component upon imaging, and thereby unlikely via conventional criteria to be malignant, should be removed promptly if the cyst fluid contained a TP53 mutation. Radical, rather than conservative, surgery might be appropriate due to the high likelihood of an aggressive type II cancer. In contrast, if a BRAF mutation was identified, the lesion is presumably a borderline or low-grade tumor; thus conservative rather than radical surgery might be sufficient. Lastly, given that certain types of ovarian cancers (type II) tend to respond well to chemotherapy while others (type I) are relatively chemoresistant, knowing the type of cancer present prior to surgery based on the mutation profile could help guide decisions regarding the use of neoadjuvant chemotherapy. Validation of these data in a much larger, prospective trial will of course be required before incorporation of this approach into clinical practice.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Materials and Methods

Patient Samples

Cyst fluids were collected prospectively from 77 women presenting with a suspected ovarian tumor. Patients were diagnosed by transvaginal sonography or computed tomography and admitted for surgical removal of the cyst by gynecologic oncology surgeons at Sahlgrenska University Hospital, Gothenburg, Sweden. The study was approved by the ethical board of Gothenburg University and patients provided written consent. According to the approved protocol, ovarian cyst fluids were collected after removal of the cyst from the abdomen. All samples were immediately put in 4° C. for 15-30 minutes, centrifuged for 10 minutes at 500 g, and aliquoted into Eppendorf tubes. The fluids were transferred to −80° C., within 30-60 minutes after collection. All histology was reviewed by board-certified pathologists (Table 1).

Plasma HE4 concentrations were determined using a commercial HE4 EIA assay (Fujirebio Diagnostics) and plasma CA-125 levels were measured using the Architect CA 125 II (Abbott Diagnostics, USA). DNA was purified from tumor tissue (either freshly-frozen, or formalin-fixed and paraffin-embedded) after microdis section to remove neoplastic components. DNA was purified from tumors and from cyst fluids using an AllPrep DNA kit (Qiagen) according to the manufacturer's instructions. Purified DNA from all samples was quantified as previously described (52).

Statistical Analysis

A Wilcoxon rank-sum test was used to compare the amount of DNA in the cancers and borderline tumors with the amount of DNA in the simple cysts and benign tumors. The fraction of samples detected by tumor-specific mutations in the cyst fluid, as well as their 95% confidence intervals, was calculated for each tumor type (Table 3). When the presence of a mutation in the cyst fluid was used to predict the need for surgery, the sensitivity and specificity of the test, as well as their 95% confidence intervals, were calculated. Firth's penalized likelihood logistic regression was used to quantify the association between molecular features of cyst fluids and the need for surgery (Table 4) in a multivariate model. The model predictors included the presence of mutation, log 10(ng) of cyst DNA and indicators for normal CA-125 and HE4 values. Normal CA-125 values were defined as <35 U/mL and normal HE4 values were defined as <92 pmol/L and <121 pmol/L for pre- and post-menopausal women, respectively. Statistical analyses were performed using the R statistical package (version 3.1.2). Unless noted otherwise, all patient-related values are reported as means±SD.

Mutation Detection and Analysis

DNA from either cyst fluids or tumors was used for multiplex PCR, as previously described (34). One-hundred-and-thirty-three primer pairs were designed to amplify 110 to 142 bp segments containing regions of interest from the following 17 genes: AKT1, APC, BRAF, CDKN2A, CTNNB1, EGFR, FBXW7, FGFR2, KRAS, MAPK1, NRAS, PIK3CA, PIK3R1, POLE, PPP2R1A, PTEN, and TP53. Primer sequences are listed in Table S1. These primers were used to amplify DNA in 25 µL reactions as previously described (34). For each sample, three multiplex reactions, each containing non-overlapping amplicons, were performed. Reactions were purified with AMPure XP beads (Beckman Coulter) and eluted in 100 µL of Buffer EB (Qiagen). A fraction (2.5 µL) of purified PCR products were then amplified in a second round of PCR, as described (34). The PCR products were purified with AMPure and sequenced on an 1llumina MiSeq instrument.

We used Safe-SeqS, an error-reduction technology for detection of low frequency mutations as described to distinguish better between genuine mutations in the samples and artifactual variants arising from sequencing and sample preparation steps, (34). High quality sequence reads were selected based on quality scores, which were generated by the sequencing instrument to indicate the probability a base was called in error. The template-specific portion of the reads was matched to reference sequences. Reads from a common template molecule were then grouped based on the unique identifier sequences (UIDs) that were incorporated as molecular barcodes. Artifactual mutations introduced during the sample preparation or sequencing steps were reduced by requiring a mutation to be present in >90% of reads in each UID family (i.e., to be scored as a "supermutant"). In addition, DNA from normal individuals was used as a control to identify potential false positive mutations (see main text). Only supermutants in samples with frequencies far exceeding their frequencies in control DNA samples (i.e., >mean+5 standard deviations) were scored as positive.

Example 2—Characteristics of the Tumors and Cyst Fluid Samples

DNA was isolated from surgically excised ovarian cysts of 77 women. Ten of them had non-neoplastic cysts, 12 had benign tumors, 24 had borderline tumors, and 31 had cancers (13 Type I and 18 Type II). Age, histopathologic diagnosis, stage, and other clinical information are provided in Table 1. The median amount of DNA recovered from the cysts was 222 ng (interquartile range (IQR) of 53 to 3120 ng) (Table 2). There was no significant difference in the amounts of DNA between borderline tumors and type I or type II cancers (Table 2). However, the borderline tumors and cancers contained significantly more DNA than the non-neoplastic cysts or benign tumors (4453±6428 ng vs. 62±64 ng; p<0.001, Wilcoxon rank-sum test).

Example 3—a Multiplex PCR-Based Test to Identify Tumor-Specific Mutations in Cyst Fluid Samples We designed a multiplex PCR-based test that could simultaneously assess the regions of 17 genes frequently mutated in ovarian tumors. The amount of DNA shed from neoplastic cells was expected to be a minor fraction of the total DNA in the cyst fluid, with most DNA emanating from normal cells. We therefore used a sensitive detection method, called Safe-SeqS (Safe-Sequencing System), to identify mutations in cyst fluid samples (34). In brief, primers were designed to amplify 133 regions, covering 9054 distinct nucleotide positions within the 17 genes of interest (Table S1). Three multiplex PCR reactions, each containing non-overlapping amplicons, were then performed on each sample. One primer in each pair included a unique identifier (UID) for each template molecule, thereby drastically minimizing the error rates associated with PCR and sequencing, as described previously (34) (Table S1). Under the conditions used in the current experiments, mutations present in >0.1% of template molecules could generally be reliably determined. We could not perform sequencing on five cysts (two simple cysts, two cystadenomas, one borderline tumor) because there was insufficient DNA (<3 ng recovered), and these were scored in a conservative fashion, as "negative" for mutations. When this test was applied to the 22 cyst fluids obtained from patients with simple cysts (n=9) or benign tumors (n=13), no mutations were identified (Tables 2 and 3). This was in stark contrast to the fluids obtained from the 18 patients with type II cancers, all of which were found to contain a mutation (Tables 2 and 3). Ten (77%) of the 13 cyst fluids from patients with type I cancers and 19 (79%) of the 24 cyst fluids from patients with borderline tumors contained at least one detectable mutation. When categorized by the need for surgery (i.e., presence of a borderline tumor or a type I or type II cancer), the sensitivity of this test was 85% (47 of 55 cysts; 95% confidence interval of 73% to 94%) and the specificity was 100% (95% confidence interval of 78% to 100%; Table 3).

Ovarian cancers are generally detected only late in the course of disease, explaining the poor prognosis of patients. Accordingly, only 11 of the 31 cysts associated with cancers in our study had early (Stage I or II) disease (Table 1). As expected, most of these were type I carcinomas (n=8). Nevertheless, it was encouraging that mutant DNA could be detected in nine (82%) of these 11 patients (Table 3). Mutations could be detected in 95% of the 20 patients with Stage III or IV cancers (Table 3).

A variety of control experiments were performed to confirm the integrity of these results. One informative positive control was provided by the results of sequencing of DNA from the tumors, using the identical method used to analyze DNA from the cyst fluids. Fifty-three of the 55 borderline and malignant cases had tumor available for this purpose. Every mutation identified in a tumor was found in its cyst fluid, and vice versa. As expected, the mutant allele frequencies in the tumors were often, but not always, higher than in the cyst fluid (Table 2). As another positive control, we used an independent PCR and sequencing reaction to confirm each of the cyst fluid mutations listed in Table 2. This validated not only the presence of a mutation, but also confirmed its fractional representation. The median relative difference between the fractions of mutant alleles in replicate experiments was 7.0% (IQR of 3.5% to 8.9%). Finally, four patients were found to have two independent mutations (Table 2). For example, the cyst fluid of patient OVCYST 081, who had high-grade endometrioid carcinoma, had a missense mutation (R280K) in TP53 plus an in-frame deletion of PIK3R1 at codons 458 and 459 of PIK3R1. The TP53 mutation was found in 3.0% of alleles while the PIK3R1 mutation was found in 3.7% of the alleles analyzed. Similar mutant allele frequencies among completely different mutations in the cyst fluid of three other patients provided further indicators of reproducibility (Table 2). All genetic assays were performed in a blinded manner, with the operator unaware of the diagnoses of the patients from whom the cyst fluids were obtained.

In addition to DNA from normal individuals used as controls, additional negative controls were provided by the simple cysts and benign tumors. Using the identical assay, none of the DNA from their cyst fluids contained detectable mutations (Table 2). A final control was provided by the borderline and malignant tumors themselves. In general, only one or two of the 9054 base-pairs (bp) queried were mutated in any one tumor (Table 2). The other ~9000 bp could then be independently queried in the corresponding cyst fluid, and none of these positions were found to be mutated.

Example 4—Relationship Between the Type of Tumor Present and the Type of Mutation Found in the Associated Cyst Fluid Sample The mutant allele fractions in the cyst fluids tended to be higher in the type II cancers (median of 60.3%) than the type I cancers (median of 7.8%) or borderline tumors (median of 2.4%), though there was considerable overlap (Tables 2 and 3). On the other hand, the type of mutation varied considerably among these cysts. In type I tumors, the genes mutated were BRAF (n=1), KRAS (n=5), NRAS (n=1), PIK3R1 (n=1), PPP2R1A (n=1), PTEN (n=1), or TP53 (n=3). Two distinct mutations were found per sample in three type I cancers. One type I cancer had a BRAF mutation. This BRAF mutation (V600_S605>D) is unusual that it resulted from an in-frame deletion/insertion rather than the base substitution (V600E) characteristic of the vast majority of BRAF mutations reported in the literature. This mutation has been observed in a papillary thyroid cancer and a cutaneous melanoma (35, 36). The deletion results in loss of a phosphorylation site in the activation loop of BRAF, while the insertion of an aspartic acid has been suggested to increase BRAF kinase activity by mimicking an activating phosphorylation (37). In contrast, all but one type II cancers (94% of 18) had mutations in TP53; the only exception was OVCYST 081, a high-grade endometrioid carcinoma. The borderline tumors were distinguished by yet a different pattern from that of the either type I or type II cancers. Of the 19 mutations in borderline tumors, 12 (63%) were at BRAF V600E, never observed in type I or type II cancers, and the remainder were at KRAS 12 or 61 (Table 2).

Example 5—Markers Associated with the Need for Surgery

A multivariate analysis was used to identify the most informative molecular features of cyst fluids and to compare them to the commonly used serum biomarkers for ovarian cancer, HE4 (human epididymis protein 4) and CA-125 (38, 39) (Table 4). We defined "informative" as indicating a need for surgery (i.e., borderline tumors or type I or II cancers). The amount of DNA in cyst fluids was generally, but not significantly, higher in the cysts requiring surgery (p=0.69, Table 4), though there were many cysts not requiring surgery that had higher DNA levels than cysts requiring surgery (FIG. S1A). Similarly, the serum CA-125 levels were significantly higher in cysts requiring surgery (p=0.01, Table 4), but there were many cysts not requiring surgery that had higher levels than those requiring surgery (FIG. S1B). Serum HE4 levels were not correlated with cyst type (P=0.92, Table 4; FIG. S1C). On the other hand, the presence of a mutation was highly informative for the presence of a cyst requiring surgery in the multivariate analysis, as no mutations were found in cysts not requiring surgery (P<0.001, Table 4).

REFERENCES

The disclosure of each reference cited is expressly incorporated herein.
1. N. A. Howlader N, Krapcho M, Garshell J, Miller D, Altekruse S F, Kosary C L, Yu M, Ruhl J, Tatalovich Z, Mariotto A, Lewis D R, Chen H S, Feuer E J, Cronin K A. (Bethesda, Md., 2014).
2. E. J. Pavlik, F. R. Ueland, R. W. Miller, J. M. Ubellacker, C. P. DeSimone, J. Elder, J. Hoff, L. Baldwin, R. J. Kryscio, J. R. van Nagell, Jr., Frequency and disposition of ovarian abnormalities followed with serial transvaginal ultrasonography. *Obstetrics and gynecology* 122, 210-217 (2013).
3. S. S. Buys, E. Partridge, M. H. Greene, P. C. Prorok, D. Reding, T. L. Riley, P. Hartge, R. M. Fagerstrom, L. R. Ragard, D. Chia, G. Izmirlian, M. Fouad, C. C. Johnson, J. K. Gohagan, P. P. Team, Ovarian cancer screening in the Prostate, Lung, Colorectal and Ovarian (PLCO) cancer screening trial: findings from the initial screen of a randomized trial. *American journal of obstetrics and gynecology* 193, 1630-1639 (2005).
4. S. S. Buys, E. Partridge, A. Black, C. C. Johnson, L. Lamerato, C. Isaacs, D. J. Reding, R. T. Greenlee, L. A. Yokochi, C. Kessel, E. D. Crawford, T. R. Church, G. L. Andriole, J. L. Weissfeld, M. N. Fouad, D. Chia, B. O'Brien, L. R. Ragard, J. D. Clapp, J. M. Rathmell, T. L. Riley, P. Hartge, P. F. Pinsky, C. S. Zhu, G. Izmirlian, B. S. Kramer, A. B. Miller, J. L. Xu, P. C. Prorok, J. K. Gohagan, C. D. Berg, P. P. Team, Effect of screening on ovarian cancer mortality: the Prostate, Lung, Colorectal and Ovarian (PLCO) Cancer Screening Randomized Controlled Trial. *Jama* 305, 2295-2303 (2011).
5. A. Demirol, S. Guven, C. Baykal, T. Gurgan, Effect of endometrioma cystectomy on IVF outcome: a prospective randomized study. *Reproductive biomedicine online* 12, 639-643 (2006).
6. F. H. Loh, A. T. Tan, J. Kumar, S. C. Ng, Ovarian response after laparoscopic ovarian cystectomy for endometriotic cysts in 132 monitored cycles. *Fertility and sterility* 72, 316-321 (1999).
7. J. T. Christensen, J. L. Boldsen, J. G. Westergaard, Functional ovarian cysts in premenopausal and gynecologically healthy women. *Contraception* 66, 153-157 (2002).
8. D. Levine, D. L. Brown, R. F. Andreotti, B. Benacerraf, C. B. Benson, W. R. Brewster, B. Coleman, P. Depriest, P. M. Doubilet, S. R. Goldstein, U. M. Hamper, J. L. Hecht, M. Horrow, H. C. Hur, M. Marnach, M. D. Patel, L. D. Platt, E. Puscheck, R. Smith-Bindman, Management of asymptomatic ovarian and other adnexal cysts imaged at US: Society of Radiologists in Ultrasound Consensus Conference Statement. *Radiology* 256, 943-954 (2010).
9. E. J. Cheng, R. J. Kurman, M. Wang, R. Oldt, B. G. Wang, D. M. Berman, M. Shih Ie, Molecular genetic analysis of ovarian serous cystadenomas. *Laboratory investigation; a journal of technical methods and pathology* 84, 778-784 (2004).
10. D. Duke, J. Colville, A. Keeling, D. Broe, T. Fotheringham, M. J. Lee, Transvaginal aspiration of ovarian cysts: long-term follow-up. *Cardiovascular and interventional radiology* 29, 401-405 (2006).
11. R. J. Kurman, M. Shih Ie, The origin and pathogenesis of epithelial ovarian cancer: a proposed unifying theory. *The American journal of surgical pathology* 34, 433-443 (2010).
12. M. L. C. R. J. Kurman, C. S. Herrington, R. H. Young WHO Classification of Tumours of Female Reproductive Organs. (International Agency for Research on Cancer Lyon, France., ed. 4th, 2014).
13. Y. Lee, A. Miron, R. Drapkin, M. R. Nucci, F. Medeiros, A. Saleemuddin, J. Garber, C. Birch, H. Mou, R. W. Gordon, D. W. Cramer, F. D. McKeon, C. P. Crum, A candidate precursor to serous carcinoma that originates in the distal fallopian tube. *The Journal of pathology* 211, 26-35 (2007).
14. N. Cancer Genome Atlas Research, Integrated genomic analyses of ovarian carcinoma. *Nature* 474, 609-615 (2011).
15. K. M. Schmeler, C. C. Sun, D. C. Bodurka, M. T. Deavers, A. Malpica, R. L. Coleman, P. T. Ramirez, D. M. Gershenson, Neoadjuvant chemotherapy for low-grade serous carcinoma of the ovary or peritoneum. *Gynecologic oncology* 108, 510-514 (2008).
16. R. E. Bristow, R. S. Tomacruz, D. K. Armstrong, E. L. Trimble, F. J. Montz, Survival effect of maximal cytoreductive surgery for advanced ovarian carcinoma during the platinum era: a meta-analysis. *Journal of clinical oncology: official journal of the American Society of Clinical Oncology* 20, 1248-1259 (2002).
17. M. E. Sherman, P. J. Mink, R. Curtis, T. R. Cote, S. Brooks, P. Hartge, S. Devesa, Survival among women with borderline ovarian tumors and ovarian carcinoma: a population-based analysis. *Cancer* 100, 1045-1052 (2004).
18. K. K. Shih, Q. Zhou, J. Huh, J. C. Morgan, A. Iasonos, C. Aghajanian, D. S. Chi, R. R. Barakat, N. R. Abu-Rustum, Risk factors for recurrence of ovarian borderline tumors. *Gynecologic oncology* 120, 480-484 (2011).
19. D. Mayr, A. Hirschmann, U. Lohrs, J. Diebold, KRAS and BRAF mutations in ovarian tumors: a comprehensive study of invasive carcinomas, borderline tumors and extraovarian implants. *Gynecologic oncology* 103, 883-887 (2006).
20. S. Jones, T. L. Wang, R. J. Kurman, K. Nakayama, V. E. Velculescu, B. Vogelstein, K. W. Kinzler, N. Papadopoulos, M. Shih Ie, Low-grade serous carcinomas of the ovary contain very few point mutations. *The Journal of pathology* 226, 413-420 (2012).
21. R. N. Grisham, G. Iyer, K. Garg, D. DeLair, D. M. Hyman, Q. Zhou, A. Iasonos, M. F. Berger, F. Dao, D. R. Spriggs, D. A. Levine, C. Aghajanian, D. B. Solit, BRAF mutation is associated with early stage disease and improved outcome in patients with low-grade serous ovarian cancer. *Cancer* 119, 548-554 (2013).
22. Y. T. Tsang, M. T. Deavers, C. C. Sun, S. Y. Kwan, E. Kuo, A. Malpica, S. C. Mok, D. M. Gershenson, K. K. Wong, KRAS (but not BRAF) mutations in ovarian serous borderline tumour are associated with recurrent low-grade serous carcinoma. *The Journal of pathology* 231, 449-456 (2013).
23. J. L. Frossard, P. Amouyal, G. Amouyal, L. Palazzo, J. Amaris, M. Soldan, E. Giostra, L. Spahr, A. Hadengue, M. Fabre, Performance of endosonography-guided fine needle aspiration and biopsy in the diagnosis of pancreatic cystic lesions. *The American journal of gastroenterology* 98, 1516-1524 (2003).

24. J. D. Lin, T. C. Chao, B. Y. Huang, S. T. Chen, H. Y. Chang, C. Hsueh, Thyroid cancer in the thyroid nodules evaluated by ultrasonography and fine-needle aspiration cytology. *Thyroid: official journal of the American Thyroid Association* 15, 708-717 (2005).
25. A. Volpe, J. R. Kachura, W. R. Geddie, A. J. Evans, A. Gharajeh, A. Saravanan, M. A. Jewett, Techniques, safety and accuracy of sampling of renal tumors by fine needle aspiration and core biopsy. *The Journal of urology* 178, 379-386 (2007).
26. P. Martinez-Onsurbe, A. Ruiz Villaespesa, J. M. Sanz Anquela, P. L. Valenzuela Ruiz, Aspiration cytology of 147 adnexal cysts with histologic correlation. *Acta cytologica* 45, 941-947 (2001).
27. O. Moran, J. Menczer, G. Ben-Baruch, S. Lipitz, E. Goor, Cytologic examination of ovarian cyst fluid for the distinction between benign and malignant tumors. *Obstetrics and gynecology* 82, 444-446 (1993).
28. J. Wu, H. Matthaei, A. Maitra, M. Dal Molin, L. D. Wood, J. R. Eshleman, M. Goggins, M. I. Canto, R. D. Schulick, B. H. Edil, C. L. Wolfgang, A. P. Klein, L. A. Diaz, Jr., P. J. Allen, C. M. Schmidt, K. W. Kinzler, N. Papadopoulos, R. H. Hruban, B. Vogelstein, Recurrent GNAS mutations define an unexpected pathway for pancreatic cyst development. *Science translational medicine* 3, 92ra66 (2011).
29. B. Vogelstein, N. Papadopoulos, V. E. Velculescu, S. Zhou, L. A. Diaz, Jr., K. W. Kinzler, Cancer genome landscapes. *Science* 339, 1546-1558 (2013).
30. J. Wu, Y. Jiao, M. Dal Molin, A. Maitra, R. F. de Wilde, L. D. Wood, J. R. Eshleman, M. G. Goggins, C. L. Wolfgang, M. I. Canto, R. D. Schulick, B. H. Edil, M. A. Choti, V. Adsay, D. S. Klimstra, G. J. Offerhaus, A. P. Klein, L. Kopelovich, H. Carter, R. Karchin, P. J. Allen, C. M. Schmidt, Y. Naito, L. A. Diaz, Jr., K. W. Kinzler, N. Papadopoulos, R. H. Hruban, B. Vogelstein, Whole-exome sequencing of neoplastic cysts of the pancreas reveals recurrent mutations in components of ubiquitin-dependent pathways. *Proceedings of the National Academy of Sciences of the United States of America* 108, 21188-21193 (2011).
31. R. Yamada, N. Maeda, H. Oguri, Y. Adachi, T. Takeuchi, M. Furihata, T. Fukaya, Is it possible to diagnose malignancy from fluid in cystic ovarian tumors? *European journal of obstetrics, gynecology, and reproductive biology* 171, 96-100 (2013).
32. A. M. Newman, S. V. Bratman, J. To, J. F. Wynne, N. C. Eclov, L. A. Modlin, C. L. Liu, J. W. Neal, H. A. Wakelee, R. E. Merritt, J. B. Shrager, B. W. Loo, Jr., A. A. Alizadeh, M. Diehn, An ultrasensitive method for quantitating circulating tumor DNA with broad patient coverage. *Nature medicine* 20, 548-554 (2014).
33. M. Murtaza, S. J. Dawson, D. W. Tsui, D. Gale, T. Forshew, A. M. Piskorz, C. Parkinson, S. F. Chin, Z. Kingsbury, A. S. Wong, F. Marass, S. Humphray, J. Hadfield, D. Bentley, T. M. Chin, J. D. Brenton, C. Caldas, N. Rosenfeld, Non-invasive analysis of acquired resistance to cancer therapy by sequencing of plasma DNA. *Nature* 497, 108-112 (2013).
34. I. Kinde, J. Wu, N. Papadopoulos, K. W. Kinzler, B. Vogelstein, Detection and quantification of rare mutations with massively parallel sequencing. *Proceedings of the National Academy of Sciences of the United States of America* 108, 9530-9535 (2011).
35. S. Barollo, R. Pezzani, A. Cristiani, M. Redaelli, L. Zambonin, B. Rubin, L. Bertazza, M. Zane, C. Mucignat-Caretta, A. Bulfone, G. Pennelli, E. Casal Ide, M. R. Pelizzo, F. Mantero, S. Moro, C. Mian, Prevalence, tumorigenic role, and biochemical implications of rare BRAF alterations. *Thyroid: official journal of the American Thyroid Association* 24, 809-819 (2014).
36. F. Cruz, 3rd, B. P. Rubin, D. Wilson, A. Town, A. Schroeder, A. Haley, T. Bainbridge, M. C. Heinrich, C. L. Corless, Absence of BRAF and NRAS mutations in uveal melanoma. *Cancer research* 63, 5761-5766 (2003).
37. H. Davies, G. R. Bignell, C. Cox, P. Stephens, S. Edkins, S. Clegg, J. Teague, H. Woffendin, M. J. Garnett, W. Bottomley, N. Davis, E. Dicks, R. Ewing, Y. Floyd, K. Gray, S. Hall, R. Hawes, J. Hughes, V. Kosmidou, A. Menzies, C. Mould, A. Parker, C. Stevens, S. Watt, S. Hooper, R. Wilson, H. Jayatilake, B. A. Gusterson, C. Cooper, J. Shipley, D. Hargrave, K. Pritchard-Jones, N. Maitland, G. Chenevix-Trench, G. J. Riggins, D. D. Bigner, G. Palmieri, A. Cossu, A. Flanagan, A. Nicholson, J. W. Ho, S. Y. Leung, S. T. Yuen, B. L. Weber, H. F. Seigler, T. L. Darrow, H. Paterson, R. Marais, C. J. Marshall, R. Wooster, M. R. Stratton, P. A. Futreal, Mutations of the BRAF gene in human cancer. *Nature* 417, 949-954 (2002).
38. R. C. Bast, Jr., T. L. Klug, E. St John, E. Jenison, J. M. Niloff, H. Lazarus, R. S. Berkowitz, T. Leavitt, C. T. Griffiths, L. Parker, V. R. Zurawski, Jr., R. C. Knapp, A radioimmunoassay using a monoclonal antibody to monitor the course of epithelial ovarian cancer. *The New England journal of medicine* 309, 883-887 (1983).
39. I. Hellstrom, J. Raycraft, M. Hayden-Ledbetter, J. A. Ledbetter, M. Schummer, M. McIntosh, C. Drescher, N. Urban, K. E. Hellstrom, The HE4 (WFDC2) protein is a biomarker for ovarian carcinoma. *Cancer research* 63, 3695-3700 (2003).
40. H. S. Kim, J. H. Ahn, H. H. Chung, J. W. Kim, N. H. Park, Y. S. Song, H. P. Lee, Y. B. Kim, Impact of intraoperative rupture of the ovarian capsule on prognosis in patients with early-stage epithelial ovarian cancer: a meta-analysis. *European journal of surgical oncology: the journal of the European Society of Surgical Oncology and the British Association of Surgical Oncology* 39, 279-289 (2013).
41. W. S. Hilger, J. F. Magrina, P. M. Magtibay, Laparoscopic management of the adnexal mass. *Clinical obstetrics and gynecology* 49, 535-548 (2006).
42. L. J. Havrilesky, B. L. Peterson, D. K. Dryden, J. T. Soper, D. L. Clarke-Pearson, A. Berchuck, Predictors of clinical outcomes in the laparoscopic management of adnexal masses. *Obstetrics and gynecology* 102, 243-251 (2003).
43. K. J. Chang, P. Nguyen, R. A. Erickson, T. E. Durbin, K. D. Katz, The clinical utility of endoscopic ultrasound-guided fine-needle aspiration in the diagnosis and staging of pancreatic carcinoma. *Gastrointestinal endoscopy* 45, 387-393 (1997).
44. M. A. Eloubeidi, V. K. Chen, I. A. Eltoum, D. Jhala, D. C. Chhieng, N. Jhala, S. M. Vickers, C. M. Wilcox, Endoscopic ultrasound-guided fine needle aspiration biopsy of patients with suspected pancreatic cancer: diagnostic accuracy and acute and 30-day complications. *The American journal of gastroenterology* 98, 2663-2668 (2003).
45. S. Ngamruengphong, K. M. Swanson, N. D. Shah, M. B. Wallace, Preoperative endoscopic ultrasound-guided fine needle aspiration does not impair survival of patients with resected pancreatic cancer. *Gut*, (2015).
46. A. A. Tran, S. B. Brown, J. Rosenberg, D. M. Hovsepian, Tract embolization with gelatin sponge slurry for prevention of pneumothorax after percutaneous computed tomography-guided lung biopsy. *Cardiovascular and interventional radiology* 37, 1546-1553 (2014).
47. W. K. Tsang, W. H. Luk, A. Lo, Ultrasound-guided plugged percutaneous biopsy of solid organs in patients with bleeding tendencies. *Hong Kong medical journal=Xianggang yi xue za zhi/Hong Kong Academy of Medicine* 20, 107-112 (2014).
48. J. R. van Nagell, Jr., P. D. DePriest, F. R. Ueland, C. P. DeSimone, A. L. Cooper, J. M. McDonald, E. J. Pavlik, R. J. Kryscio, Ovarian cancer screening with annual transvaginal sonography: findings of 25,000 women screened. *Cancer* 109, 1887-1896 (2007).
49. F. R. Ueland, C. P. Desimone, L. G. Seamon, R. A. Miller, S. Goodrich, I. Podzielinski, L. Sokoll, A. Smith, J. R. van Nagell, Jr., Z. Zhang, Effectiveness of a multivariate index assay in the preoperative assessment of ovarian tumors. *Obstetrics and gynecology* 117, 1289-1297 (2011).
50. E. Bandiera, L. Zanotti, A. S. Fabricio, E. Bucca, E. Squarcina, C. Romani, R. Tassi, E. Bignotti, P. Todeschini, G. Tognon, C. Romagnolo, M. Gion, E. Sartori, T. Maggino, S. Pecorelli, A. Ravaggi, Cancer antigen 125, human epididymis 4, kallikrein 6, osteopontin and soluble mesothelin-related peptide immunocomplexed with immunoglobulin M in epithelial ovarian cancer diagnosis. *Clinical chemistry and laboratory medicine: CCLM/ FESCC* 51, 1815-1824 (2013).
51. B. Kristjansdottir, K. Levan, K. Partheen, E. Carlsohn, K. Sundfeldt, Potential tumor biomarkers identified in ovarian cyst fluid by quantitative proteomic analysis, iTRAQ. *Clinical proteomics* 10, 4 (2013).
52. C. Rago, D. L. Huso, F. Diehl, B. Karim, G. Liu, N. Papadopoulos, Y. Samuels, V. E. Velculescu, B. Vogelstein, K. W. Kinzler, L. A. Diaz, Jr., Serial assessment of human tumor burdens in mice by the analysis of circulating DNA. *Cancer research* 67, 9364-9370 (2007).

The invention claimed is:

1. A method, comprising:
testing ovarian cyst fluid for mutations in a panel of genes mutated in an ovarian neoplasm, wherein the panel comprises BRAF, KRAS, and TP53, wherein the step of testing does not employ a whole-genome or whole-exome technique, wherein the step of testing employs a step of adding a unique identifier (UID) to each template DNA in the ovarian cyst fluid, and wherein the method has a sensitivity level of at least 70%.

2. The method of claim 1 wherein the panel further comprises one or more genes selected from a first group consisting of CTNNB1, PIK3CA, PTEN, ARID1A, and PPP2R1A.

3. The method of claim 1 wherein the step of testing employs gene-specific reagents.

4. The method of claim 1 wherein the step of testing employs mutation-specific reagents.

5. The method of claim 1 wherein the testing is performed on the ovarian cyst fluid and on a sample selected from the group consisting of cyst wall and normal, non-ovarian tissue.

6. The method of claim 1 wherein BRAF600, KRAS12, KRAS13, KRAS61, or combinations thereof are tested.

7. The method of claim 2 wherein all genes of the first group are in the panel.

8. The method of claim 1 further comprising the step of assaying amount of DNA in the cyst fluid.

9. The method of claim 1 further comprising the step of assaying amount of CA-125 levels in plasma.

10. The method of claim 1 wherein the panel further comprises one or more genes selected from a second group consisting of AKT1, APC, BRCA1, BRCA2, CDKN2A, EGFR, FBXW7, FGFR2, MAPK1, NRAS, PIK3R1, and POLE.

11. The method of claim 7 wherein the panel further comprises one or more genes selected from a second group consisting of AKT1, APC, BRCA1, BRCA2, CDKN2A, EGFR, FBXW7, FGFR2, MAPK1, NRAS, PIK3R1, and POLE.

12. The method of claim 1 wherein the ovarian cyst fluid is obtained by needle aspiration of an ovarian cyst.

13. The method of claim 1 wherein the ovarian cyst fluid is obtained prior to any surgical removal of the ovarian cyst.

14. The method of claim 1 wherein the ovarian cyst fluid is obtained after surgical removal of the ovarian cyst and recurrence of the ovarian cyst.

15. The method of claim 1 wherein the ovarian cyst fluid is from a cyst selected from the group consisting of: mesothelial cyst, follicular cyst, corpus luteal cyst, mucinous cystadenoma, endometriotic cyst, serous cystadenoma, serous cystadenofibroma, atypical proliferative serous tumor, atypical proliferative endometrioid tumor, serous carcinoma, mixed epithelial tumor, endometrioid carcinoma, clear cell carcinoma, metastatic tumors to the ovary, and mucinous carcinoma.

16. The method of claim 1 wherein a copy number variation, a loss of heterozygosity, or both, is determined in at least one of the genes in the panel.

17. The method of claim 1 wherein a point mutation, a rearrangement, a frameshift, or combinations thereof, is determined in at least one gene of the panel.

18. The method of claim 1, wherein the method has a sensitivity level of at least 85%.

19. The method of claim 1, wherein the method has a specificity level of at least 90%.

20. The method of claim 1, wherein the method has a specificity level of at least 95%.

21. The method of claim 1, wherein the ovarian neoplasm needs surgery.

22. The method of claim 1, wherein the ovarian neoplasm is a borderline tumor or malignant cancer.

23. The method of claim 1, wherein the ovarian neoplasm is a type I cancer or a type II cancer.

* * * * *